US010095833B2

(12) United States Patent
Balram et al.

(10) Patent No.: US 10,095,833 B2
(45) Date of Patent: Oct. 9, 2018

(54) MOBILE INFORMATION GATEWAY FOR USE BY MEDICAL PERSONNEL

(71) Applicant: Ricoh Company, Ltd., Tokyo (JP)

(72) Inventors: Nikhil Balram, Mountain View, CA (US); Kathrin Berkner, Los Altos, CA (US); Ivana Tosic, San Francisco, CA (US); Wanmin Wu, Redwood City, CA (US)

(73) Assignee: Ricoh Co., Ltd., Tokyo (JP)

( * ) Notice: Subject to any disclaimer, the term of this patent is extended or adjusted under 35 U.S.C. 154(b) by 0 days.

(21) Appl. No.: 14/161,601

(22) Filed: Jan. 22, 2014

(65) Prior Publication Data
US 2015/0088546 A1 Mar. 26, 2015

Related U.S. Application Data

(60) Provisional application No. 61/880,971, filed on Sep. 22, 2013.

(51) Int. Cl.
*G06Q 10/00* (2012.01)
*G06Q 50/00* (2012.01)
(Continued)

(52) U.S. Cl.
CPC ....... *G06F 19/322* (2013.01); *G02B 27/0093* (2013.01); *G02B 27/017* (2013.01);
(Continued)

(58) Field of Classification Search
CPC ........ G06Q 50/22; G06Q 50/02; G16H 10/00; G16H 10/20; G16H 10/40; G16H 10/60;
(Continued)

(56) References Cited

U.S. PATENT DOCUMENTS 6,046,712 A * 4/2000 Beller ................. G02B 27/017
345/7
6,091,546 A 7/2000 Spitzer
(Continued)

FOREIGN PATENT DOCUMENTS

WO 2005066744 A1 7/2005
WO 2005094667 A2 10/2005

OTHER PUBLICATIONS

Bray, Alex, "Google Glass will Change your Branches," American Banker, http://www.americanbanker.com/bankthink/google-glass-will-change-your-branches-1057312-1 .html, pp. 1-2, retrieved on Dec. 31, 2014. Mar. 7, 2013.
(Continued)

*Primary Examiner* — Neha Patel
(74) *Attorney, Agent, or Firm* — Patent Law Works LLP

(57) ABSTRACT

A mobile information gateway comprises: a wearable human interface module having an image delivery and display mechanism for presenting information overlaid upon a wide field of view, a computing and communication module adapted to send and receive information to and from the human interface module; and a backend service server coupled for processing medical data. The present invention also includes a method comprising: capturing information with a first mobile information gateway device; processing the captured information to determine an identity of a first user and authenticate the first user; processing the captured information to determine an identity of a patient and authenticate the patient; processing the identity of the first user and the identity of the patient to retrieve information of the patient; and resenting the retrieved information of the patient overlaid on a field of view by the first mobile information gateway device.

20 Claims, 26 Drawing Sheets

(51) Int. Cl.
  *G06F 19/00* (2018.01)
  *G16H 10/60* (2018.01)
  *G06F 21/32* (2013.01)
  *G02B 27/01* (2006.01)
  *G02B 27/00* (2006.01)
  *G16H 40/63* (2018.01)
  *G02B 27/22* (2018.01)

(52) U.S. Cl.
  CPC ..... *G02B 27/0172* (2013.01); *G02B 27/0176* (2013.01); *G06F 21/32* (2013.01); *G16H 10/60* (2018.01); *G16H 40/63* (2018.01); *G02B 27/2271* (2013.01); *G02B 2027/0132* (2013.01); *G02B 2027/0138* (2013.01); *G02B 2027/0178* (2013.01)

(58) Field of Classification Search
  CPC ........ G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
  See application file for complete search history.

(56) References Cited

U.S. PATENT DOCUMENTS

| | | | |
|---|---|---|---|
| 6,166,656 A | 12/2000 | Okada et al. | |
| 6,349,001 B1 | 2/2002 | Spitzer | |
| 6,747,611 B1 | 6/2004 | Budd et al. | |
| 6,798,876 B1 | 9/2004 | Bala | |
| 8,091,778 B1 | 1/2012 | Block et al. | |
| 8,212,859 B2 | 7/2012 | Tang et al. | |
| 8,438,110 B2 | 5/2013 | Calman et al. | |
| 8,582,850 B2 | 11/2013 | Calman et al. | |
| 2004/0024616 A1 | 2/2004 | Spector | |
| 2004/0205256 A1 | 10/2004 | Hoffman et al. | |
| 2004/0232219 A1* | 11/2004 | Fowler .............. | G06F 19/323 235/380 |
| 2006/0115130 A1* | 6/2006 | Kozlay .............. | 382/117 |
| 2008/0005702 A1 | 1/2008 | Skourup et al. | |
| 2008/0218588 A1 | 9/2008 | Stetten | |
| 2008/0227429 A1 | 9/2008 | Hodgson et al. | |
| 2008/0253631 A1 | 10/2008 | Oosawa | |
| 2010/0121191 A1 | 5/2010 | Ariff et al. | |
| 2011/0153341 A1* | 6/2011 | Diaz-Cortes .............. | 705/2 |
| 2011/0239142 A1 | 9/2011 | Steeves et al. | |
| 2012/0075168 A1* | 3/2012 | Osterhout .............. | G02B 27/017 345/8 |
| 2012/0200601 A1 | 8/2012 | Osterhout et al. | |
| 2012/0230557 A1* | 9/2012 | Calman et al. ............ | 382/128 |
| 2012/0233072 A1 | 9/2012 | Calman et al. | |
| 2012/0235785 A1 | 9/2012 | Alberth et al. | |
| 2013/0005443 A1 | 1/2013 | Kosta et al. | |
| 2013/0016070 A1 | 1/2013 | Starner et al. | |
| 2013/0027411 A1 | 1/2013 | Hebler | |
| 2013/0038510 A1 | 2/2013 | Brin et al. | |
| 2013/0044042 A1 | 2/2013 | Olsson et al. | |
| 2013/0053063 A1 | 2/2013 | McSheffrey | |
| 2013/0069850 A1 | 3/2013 | Mukawa et al. | |
| 2013/0070338 A1 | 3/2013 | Gupta et al. | |
| 2013/0162944 A1 | 6/2013 | Fateh | |
| 2013/0188080 A1 | 7/2013 | Olsson et al. | |
| 2013/0190096 A1 | 7/2013 | Ronen et al. | |
| 2013/0196457 A1 | 8/2013 | Nakajima et al. | |
| 2013/0196757 A1 | 8/2013 | Latta et al. | |
| 2013/0222369 A1 | 8/2013 | Huston et al. | |
| 2013/0317753 A1* | 11/2013 | Kamen et al. .............. | 702/19 |
| 2014/0005506 A1 | 1/2014 | Elghazzawi | |
| 2014/0063055 A1 | 3/2014 | Osterhout | |
| 2014/0145915 A1* | 5/2014 | Ribble .............. | G06F 19/327 345/8 |
| 2014/0194702 A1 | 7/2014 | Tran | |

OTHER PUBLICATIONS

European Search Report for Application No. 14179114.5, dated Nov. 6, 2014, 6 pages.
European Search Report for Application No. 14179269.7, dated Nov. 6, 2014, 6 pages.
European Search Report for Application No. 14179432.1, dated Nov. 6, 2014, 5 pages.
European Search Report for Application No. 14185144.4, dated Nov. 10, 2014, 5 pages.
Notice of Allowance for U.S. Appl. No. 14/137,529, dated Nov. 20, 2015, Nikhil Balram, 25 pages.
Final Office Action for U.S. Appl. No. 14/161,609, dated Nov. 27, 2015, Nikhil Balram, 29 pages.
Final Office Action for U.S. Appl. No. 14/137,507, dated Jul. 11, 2016, 16 pages.
Non-Final Office Action for U.S. Appl. No. 14/161,613, dated Jul. 29, 2016, 20 pages.
Final Office Action for U.S. Appl. No. 14/161,609, dated Sep. 15, 2016, 32 pages.
Non-Final Office Action for U.S. Appl. No. 14/137,558, dated Sep. 22, 2016, 25 pages.
Final Office Action for U.S. Appl. No. 14/137,558 dated May 4, 2016, 26 pages.
Final Office Action for U.S. Appl. No. 14/161,613 dated Feb. 2, 2016, 18 pages.
Non-Final Office Action for U.S. Appl. No. 14/137,507 dated Feb. 11, 2016, 13 pages.
Non-Final Office Action for U.S. Appl. No. 14/161,609 dated Mar. 10, 2016, 27 pages.
Final Office Action for U.S. Appl. No. 14/161,613, dated Dec. 29, 2016, 23 pages.
Notice of Allowance for U.S. Appl. No. 14/137,558, dated Jan. 27, 2017, 21 pages.
Non-Final Office Action for U.S. Appl. No. 14/161,609 dated Apr. 3, 2017, 37 pages.
Non-Final Office Action for U.S. Appl. No. 14/137,507 dated Apr. 21, 2017, 16 pages.
Notice of Allowance for U.S. Appl. No. 14/161,613 dated May 5, 2017, 11 pages.
Final Office Action for U.S. Appl. No. 14/137,507 dated Oct. 4, 2017, 28 pages.
Notice of Allowance for U.S. Appl. No. 14/137,507, dated Mar. 9, 2018, 20 Pages.
Non-Final Office Action for U.S. Appl. No. 14/161,609, dated Mar. 14, 2018, 38 Pages.

* cited by examiner

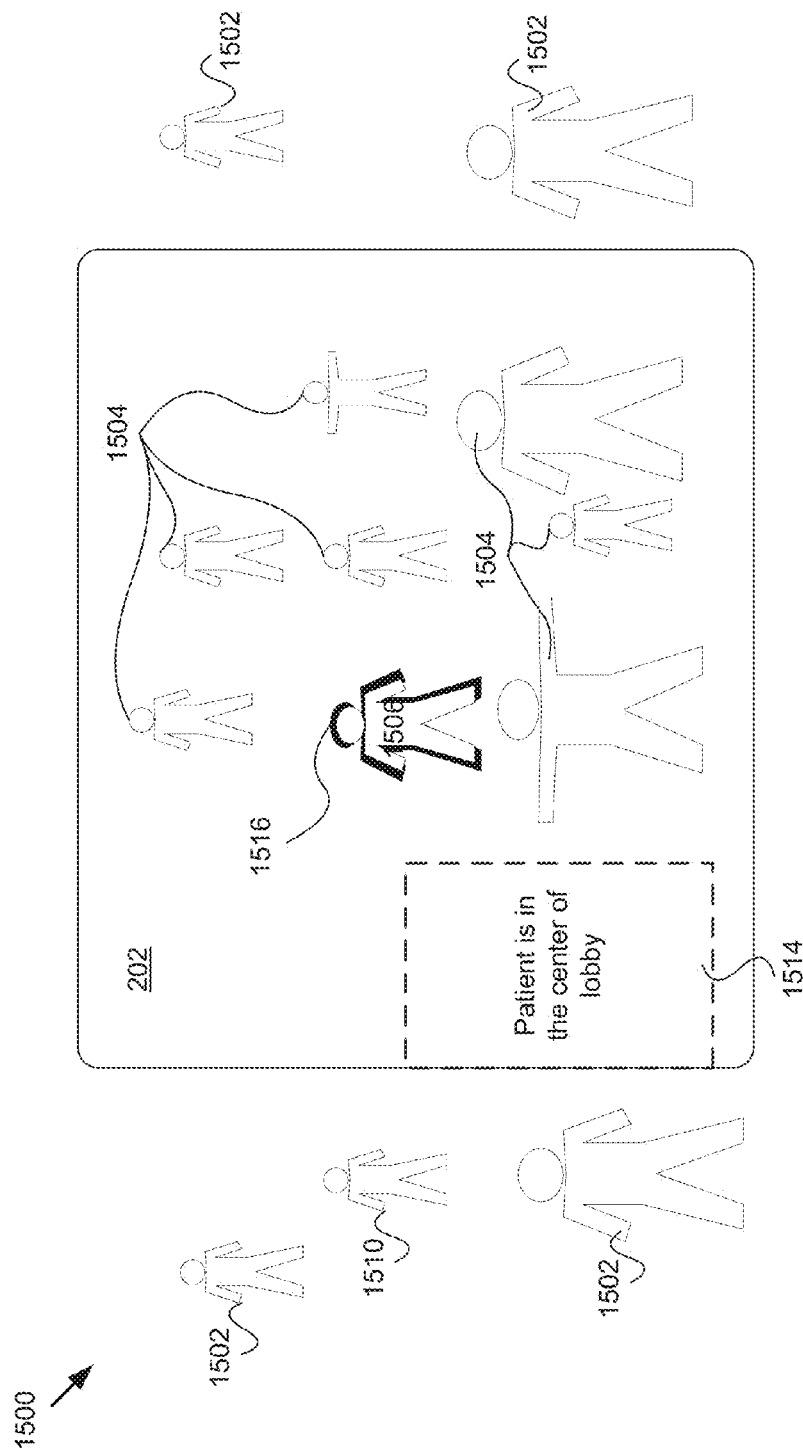

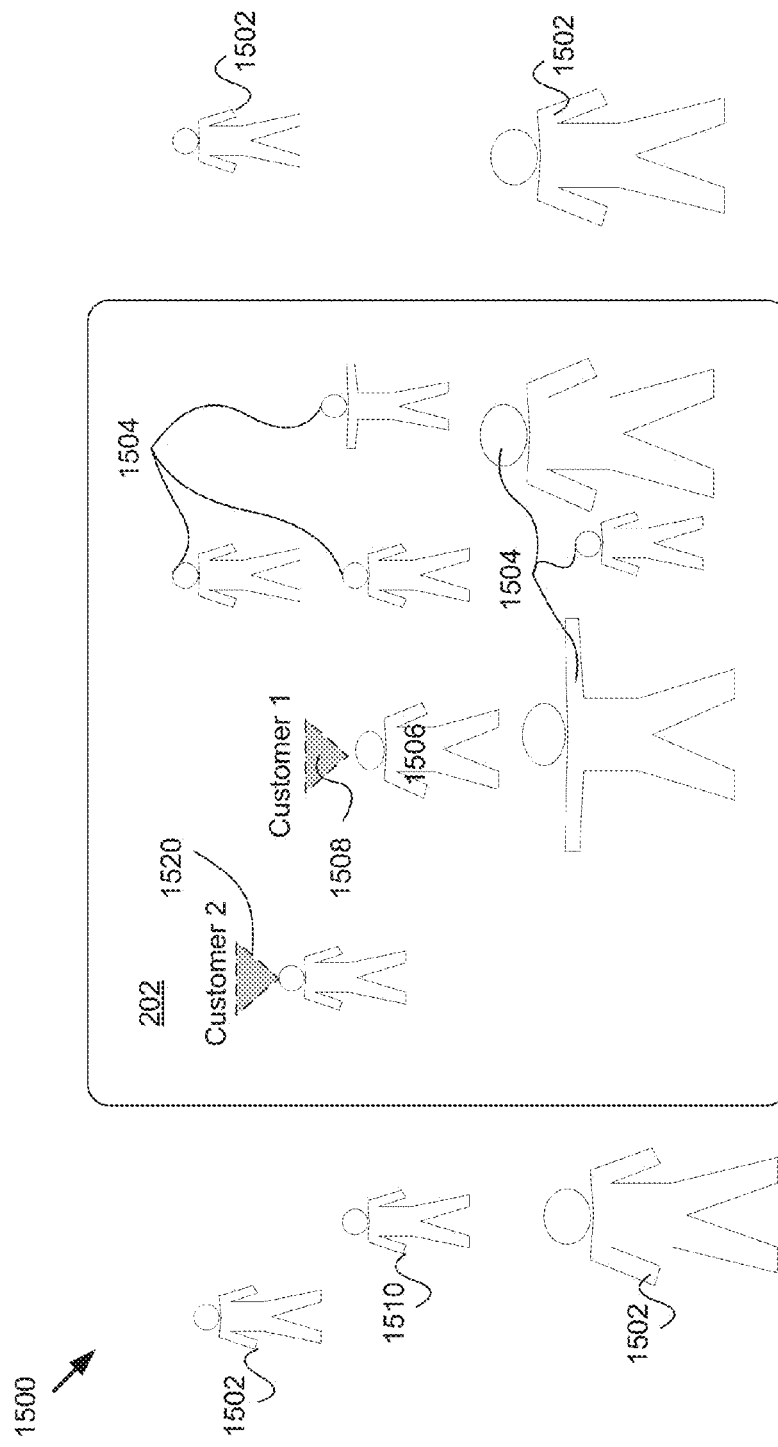

MOBILE INFORMATION GATEWAY FOR USE BY MEDICAL PERSONNEL

CROSS-REFERENCE TO RELATED APPLICATIONS

The present application claims priority, under 35 U.S.C. § 119, to U.S. Provisional Patent Application Ser. No. 61/880,971, filed Sep. 22, 2013 and entitled "Mobile Information Gateway For Health Care and Medical Uses," the entirety of which is hereby incorporated by reference.

BACKGROUND OF THE INVENTION

1. Field of the Art

The present specification generally relates to the field of mobile computing and associated devices. More particularly, the present specification relates to a mobile information gateway and methods that enable the user to continually access and use relevant information needed at any time and place. Still more particularly, the present specification relates to a mobile information gateway for use by medical personnel.

2. Description of the Related Art

In recent years, the computing capabilities as well as the functionality offered by mobile computing devices such as tablets, smart phones, and laptops have increased dramatically. The processing power provided by many present-day smart phones now exceeds the processing power that was available to desktop computers only a few years ago. However, because of their small size and form factor, inputting data and presenting information to the user have and continue to be a challenge for smart phones. Even for tablet computers, it is difficult to input information and tablets have limited display real estate to present information.

For a number of reasons, mobile computing devices have limited physical screen size that is not sufficient to provide a rich and complete experience that fully replaces what is available in a physical location. First, the existing mobile computing devices provide too narrow a field of view to see all types of information or to share information with others satisfactorily. Second, mobile computing devices do not have the capability to display information for a true 3-D experience. Third, existing mobile computing devices do not provide interfaces to input all types of material and manipulate all types of object satisfactorily.

SUMMARY OF THE INVENTION

The present invention overcomes the deficiencies and limitations of the prior art, at least in part, with a mobile information gateway. In one embodiment, the mobile information gateway comprises: a wearable human interface module (HIM) having an image delivery and display mechanism for presenting information with a wide field of view and in three dimensions, an audio input device, an audio output device, a camera, and an interface unit coupled for communication; a computing and communication module (CCM) coupled for communication with the wearable human interface module, the computing and communication module adapted to receive information from the human interface module and adapted to send commands and information to the interface module including information for presentation by the image deliver and display mechanism, the computing and communication module also adapted to communicate via a conventional network; and one or more backend service servers coupled for communication with the computing and communication module via the conventional network, the backend service server for processing data from the computing and communication module including user identification and verification.

In another embodiment, a method of using a mobile information gateway by medical personnel comprises: capturing information with a first mobile information gateway device; processing the captured information to determine an identity of a first user and authenticate the first user; processing the captured information to determine an identity of a patient and authenticate the patient; processing the identity of the first user and the identity of the patient to retrieve information of the patient; and presenting the retrieved information of the patient overlaid on a field of view by the first mobile information gateway device.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

The specification is illustrated by way of example, and not by way of limitation in the figures of the accompanying drawings in which like reference numerals are used to refer to similar elements.

FIGS. 15A-15E are graphic representations of a field of view of an area through a substrate of the human interface module with information overlaid upon the substrate.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

The present invention will now be described in the context of particular use cases of banking where the system is used by tellers, bank managers, service representatives and other employees or contractors of a bank and of healthcare where the system is used by medical professionals, physician's assistants, medical technicians and sometimes patients. It should be understood that the descriptors used herein are merely convenient labels to describe the use and operation of the system, that any person could use the human interface module 102 or other components of the system 100, and that they could be grouped together in a variety of groups other than by branch, bank or company. The present invention is useful to any number of users independent of their title or primary job responsibility. The advantages of the system are achieved by cooperation of its components and use by groups to cooperate and interact with each other as shown in the figures and described in the examples below.

System Overview

Figure 1A:
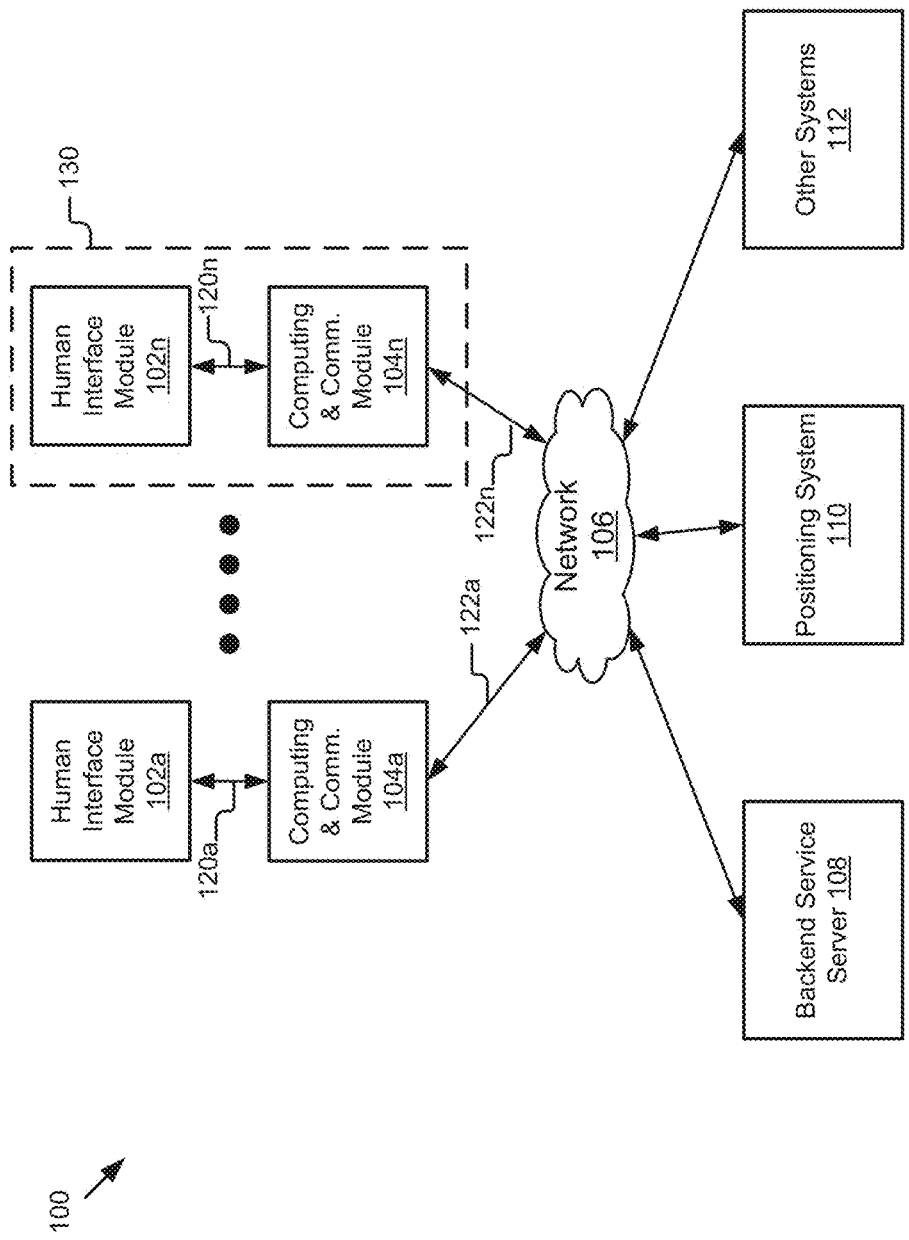
FIG. 1A is a high-level block diagram of one embodiment of a mobile information gateway.

FIG. 1A illustrates a high-level block diagram of a mobile information gateway 100 according to the present invention. In one embodiment, the illustrated description of the mobile information gateway 100 includes: a plurality of human interface modules 102a-102n (also referred to herein individually and collectively as 102), a plurality of computing and communication modules 104a-104n (also referred to herein individually and collectively as 104), a network 106, a backend service server 108, a positioning system 110 and other systems 112. The human interface module 102a is coupled for communication with a corresponding computing and communication module 104a by signal line 120a. In some embodiments, signal line 120a provides power as well as command and data signals. In some embodiments, signal line 120a may be a wired or wireless communication mechanism between a respective human interface module 102a and a computing and communication module 104a. Similarly, the human interface module 102n is coupled for communication with the corresponding computing and communication module 104 and by signal line 120n. The human interface module 102 and the computing and communication module 104 are preferably portable and used together by a single user. Each of the computing and communication modules 104a-104n is coupled for communication to the network 106 via signal lines 122a-122n, respectively. Signal lines 122a-122n represent wireless communication channels between the computing and communication modules 104 and the network 106. The network 106 is also coupled for communication with the backend service server 108, the positioning system 110 and other systems 112. Thus, the computing and communication modules 104 are able to communicate via the network 106 with any of the backend service server 108, the positioning system 110 or other systems 112. In some embodiments and in this application, the human interface module 102 and the computing and communication module 104 are collectively referred to as a mobile information gateway device 130.

The human interface module 102 is a wearable computing device including an image delivery and display mechanism, an audio delivery and speaker system, and image and audio capture capability. The human interface module 102 preferably includes an image delivery and display mechanism that is capable of providing a wide field of view to present large images or images in three dimensions. The image delivery and display mechanism seamlessly overlays a digital visualization (such as graphics, texts, images, and videos) over the real world, e.g., placing a virtual 3D chart on a physical table top. The audio delivery and speaker system includes an audio output device that provides mono or stereo sound to the user. The human interface module 102 also includes the ability to capture images, sound and various other information using different sensors. For example, the human interface module 102 processes images and recognizes gestures as one method for manipulating data presented by the human interface module 102. For another example, the human interface module 102 may capture real world scenes and deliver them to the computing and communication module 104 in real time which processes the images to generate 3D depth map of the scene and/or perform object recognition. In some embodiments, the human interface module 102 includes a portable light source. The human interface module 102 will be described in more detail below with reference to FIGS. 2 and 3.

The computing and communication module 104 provides computational support for the human interface module 102. The computing and communication module 104 is coupled by signal line 120 to the human interface module 102. In some embodiments, the signal line 120 is a combination of optical relay fibers and electronic wires for providing display data, commands and power and for receiving data and commands. The computing and communication module 104 provides general graphics and multimedia processing for any type of application. The computing and communication module 104 may operate using the conventional operating system such as android, Windows or iOS. The computing and communication module 104 also has high-bandwidth communication capabilities and is coupled for communication with the network 106. The computing and communication module 104 is described in more detail below with reference to FIGS. 2 and 3.

The network 106 may be a conventional type, wired or wireless, and may have any number of configurations, for example, a star configuration, token ring configuration or other configurations. Furthermore, the network 106 may include a local area network (LAN), a wide area network (WAN) (e.g., the Internet), and/or any other interconnected data path across which multiple devices may communicate. In some implementations, the network 106 may be a peer-to-peer network. The network 106 may also be coupled to or include portions of a telecommunications network for sending data in a variety of different communication protocols.

In some implementations, the network 106 includes Bluetooth communication networks, Wi-Fi networks, or a cellular communications network for sending and receiving data, e.g., via short messaging service (SMS), multimedia messaging service (MMS), hypertext transfer protocol (HTTP), direct data connection, WAP, email, etc.

The backend service server 108 is a system or server coupled to the network 106 capable of providing a service. The backend service server 108 may be either a hardware server or a software server. The backend service server 108 may be entirely hardware, entirely software or a combination of hardware and software. The backend service server 108 may include a processor, memory, applications, a database and other information. Although only a single backend service server 108 is shown in FIG. 1A, it should be understood that there may be any number of backend service servers 108 or a server cluster. In some embodiments, different servers offer different services. For example, different service components in the backend service servers 108 may provide services related to a particular business vertical such as banking, retail sales, transportation, food service, hotel and housing, etc. Similarly different service components in the backend service servers 108 may provide different types of computing functions such as image processing, scene analysis, facial recognition, iris detection and authentication, voice recognition, encryption, translation, format conversion, etc. In some embodiments, the backend services server 108 also includes a service recommendation engine implemented as software or routines having the functionality described below. The backend service server 108 is coupled for communication with one or more of the computing and communication modules 104 via the network 106.

The mobile information gateway may optionally include the positioning system 110. The positioning system 110 may be a series of sensors, a grid or array of sensors, or beacons for detecting the location and orientation of the human interface module 102 and/or the computing and communication module 104. For example, the positioning system 110 may also use data from the human interface module 102 and/or the computing and communications module 104 to determine their location and orientation. For example, various indoor systems may be used to get precise location and orientation information for smaller environments where the human interface module and the computing and communications module 104 will be used. The positioning system 110 may use GPS, Wi-Fi positioning, cellular positioning, MEMS sensors, Bluetooth beacons, indoor messaging systems, near field communications, RFID, and ultrasonic beacons, camera networks, etc. Moreover, in some embodiments, customers or users are given a beacon such as a wireless transmitter as they entered the branch of a bank. In other embodiments, the user's smart phone may be used to generate a beacon to locate the customer in the bank branch. This wireless transmitter can emit a fixed code which can be used to identify specific customers. The mobile information gateway 100 uses the signal from the wireless transmitter to determine the precise location within the branch of the customer. This location information can then be provided to a teller wearing a mobile information gateway device 130 so that the teller can locate the person they are supposed to service within the branch.

The other systems 112 in FIG. 1A represent other existing systems. The human interface module 102 and the computing and communications module 104 are capable of interfacing and interacting with other systems 112. The human interface module 102 and the computing and communications module 104 can send information and commands to the other systems 112 or receive information from the other systems 112. In some embodiments, the other systems 112 may include motion sensors, wall displays, coffee makers, projection systems for lighting control, temperature sensors, ambient light sensors, body health monitoring sensors, pollution sensors, radiation sensors, HVAC systems etc.

Figure 1B:
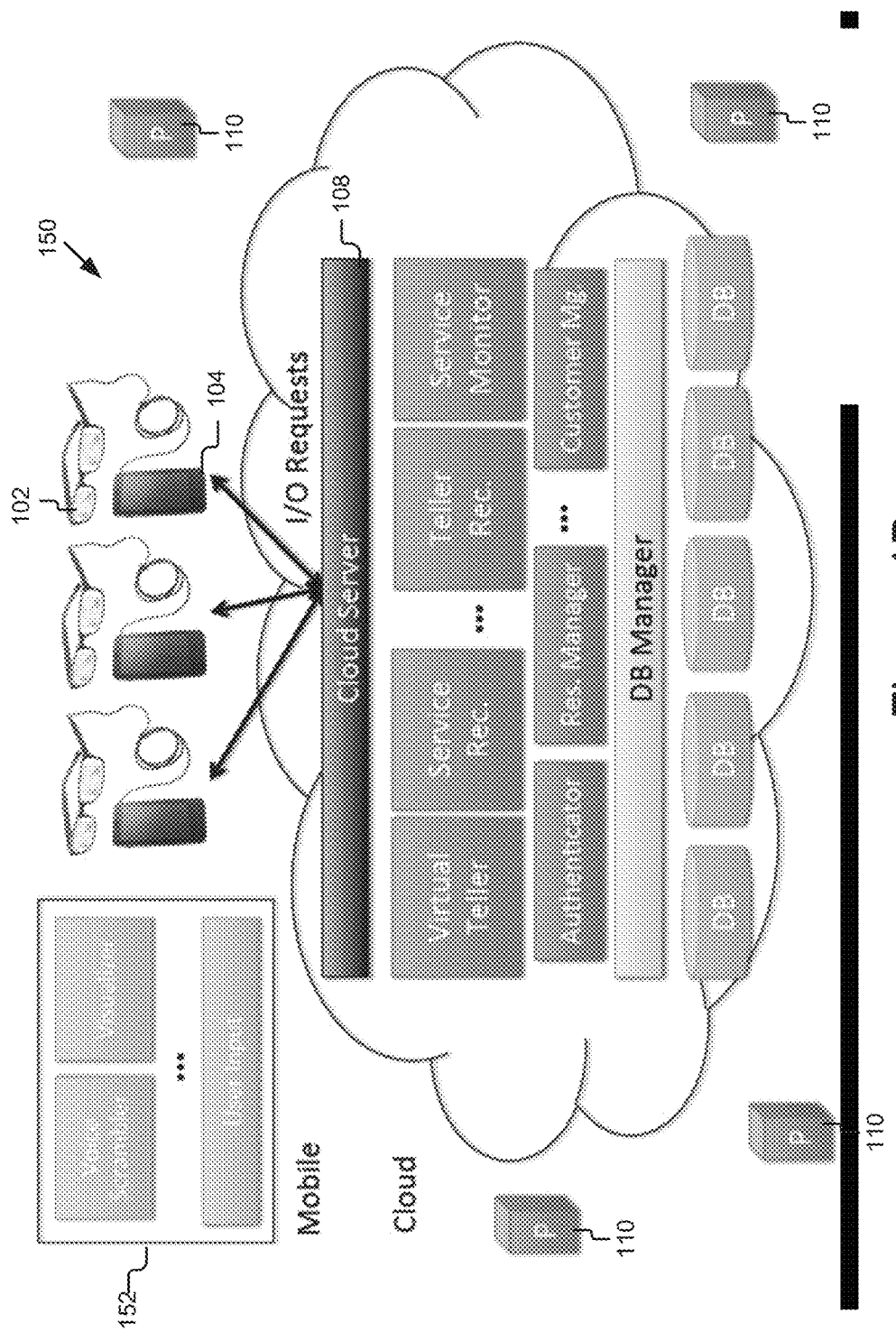
FIG. 1B is a high-level block diagram of a second embodiment of the mobile information gateway.

FIG. 1B is a high-level block diagram of a second embodiment of the mobile information gateway 150. The second embodiment of the mobile information gateway 150 provides a specific embodiment in which the human interface module 102, the computing and communications module 104 and the backend service server 108 are used to enhance the delivery of banking services. In this example, there are again a plurality of pairs of human interface modules 102 and computing and communications modules 104 (e.g., a plurality of mobile information gateway devices 130). Each human interface module 102 is coupled to a corresponding computing and communications module 104. The mobile information gateway 150 also includes the position system 110 with sensors positioned at different locations. In this embodiment, the computing and communications modules 104 communicate with the backend services server 108 that is located in the cloud. The human interface module 102 is adapted to receive user input such as gestures, to present the images via a visualizer and to scramble or encrypt the voices of the users. These functions are represented by box 152 and are operational in the human interface module 102 and/or the computing and communications module 104. In another scenario, the electronic audio signal between the two people talking is encrypted. For example, if a first user, Alice, and a second user, Bob, want to have a private conversation, they could each put on a mobile information gateway device 130a, 130b. The human interface module 102 of each mobile information gateway device 130 will have both audio input (microphone) and output (speaker and an earphone) components. When Alice talks/whispers, for example, her voice is picked up by her own microphone on mobile information gateway device 130a, and transmitted to Bob's earphones on his mobile information gateway device 130b via networks. Now suppose another person Chuck stands near them. To avoid Chuck hearing Alice's words, Alice's mobile information gateway device 130a could output some scrambling audio signals through its speaker as soon as its microphone detects Alice speaking. The scrambling signals could be designed in such a way that the mix of Alice's normal voice and the scrabbling signals is incomprehensible (and this is what Chuck hears). Alice's and Bob's earphones could have some noise-canceling capability such that the scrambling signals don't affect them.

In some embodiments, the human interface module 102 and the computing and communications modules 104 are utilized by customers of a bank. In the same or other embodiments, the human interface module 102 and the computing and communications modules 104 are utilized by employees of a bank.

The backend service server 108 in this embodiment is specifically adapted to provide various functions that are part of providing banking services. For example, the backend service server 108 includes a virtual teller, a service recommendation module, a teller recommendation module and a service monitor module. The virtual teller module interfaces with the human interface module 102 and the computing and communications module 104 to present a virtual teller when the customer uses these devices. The service recommendation module is utilized by a bank employee using the human interface module 102 and the computing and communications module 104. Based on images and other information captured by the human interface module 102 and sent to the service recommendation module, a suggested recommendation for a type of service or product will be presented on the display of the human interface module 102 so that the bank representative may offer it to the customer. The teller recommendation module may be accessed by either the employee or the customer, and information about the customer is sent to the teller recommendation module so that the customer may be identified and authenticated, and then a teller may be recommended to the customer. The recommended teller may be based on a variety of factors including which tellers are busy or have the longest wait times, teller skills for specialized services needed by the customer, personality matches between the teller and the customer, ethnographical/language specific matching between teller and customer, historical interactions (positive or negative) between the customer and the teller, expertise of the teller or bank employee, etc. Service monitor module is a module for capturing information from any one or all of the human interface modules 102 to monitor and ensure that services are delivered according to the banks guidelines. These modules in turn may call upon an authenticator module, a reservation manager module or a customer manager module as well as access data available from a database manager in a variety of databases. The databases store information about customers, financial instruments, services, security, transactions, etc. The authentication module is used to authenticate the customer, to authenticate the bank employee, and to authenticate that both are authorized to perform a particular action. Reservation manager manages the delivery of services by the bank employees and can make recommendations as to who to service next as well as what services to provide.

Figure 1C:
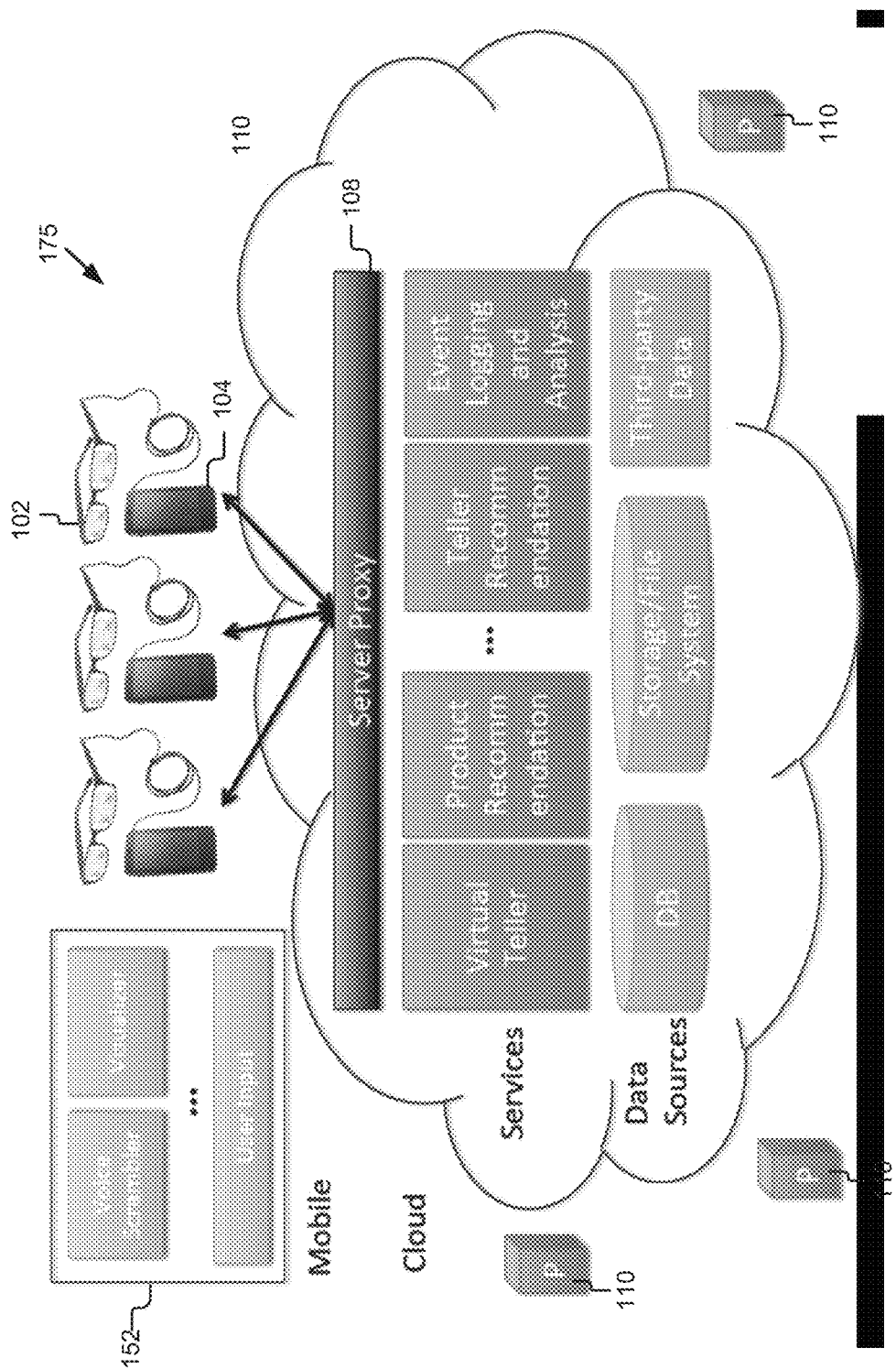
FIG. 1C is a high-level block diagram of a third embodiment of the mobile information gateway.

FIG. 1C is a high-level block diagram of a third embodiment of the mobile information gateway 175. In this third embodiment of the mobile information gateway 175, like numerals have been used to reference like components with the same or similar functionality as has been described above for the second embodiment of the mobile information gateway 150. Where the components have similar functionality, that description will not be repeated here. However, the third embodiment of the mobile information gateway 175 differs in some notable respects. First, the backend service server 108 includes three general layers: (1) Server Proxy which interacts with the computing and communications module 104 to receive and send requests and data, (2) Services which include a number of service components such as virtual teller, product recommendation, and teller recommendation. (3) Data Sources which may include databases, storage/file system, and third party data. In some embodiments, these layers are in software level and operate on a cluster of computers or servers. These computers form a distributed network to provide backend services to the computing and communications module 104 via a common interface.

It should be understood that for other use cases such as in healthcare and emergency response or specialized equipment use, the backend service server 108 may have a similar organization and structures or modules as depicted in FIGS. 1B and 1C; however, some of those modules may perform slightly different functions. For example, rather than a virtual teller module there may be a virtual physician or medical personnel module, rather than a service recommendation module there may be a triage module or a medical service recommendation module, rather than a teller recommendation module there may be a medical personnel recommendation module, and rather than the product recommendation module there may be a medical product recommendation module. It should also be understood that for some use cases the embodiment of FIG. 1C that does not include a database manager and associated authentication information may be more applicable for the emergency use case or the specialized equipment case.

Figure 2:
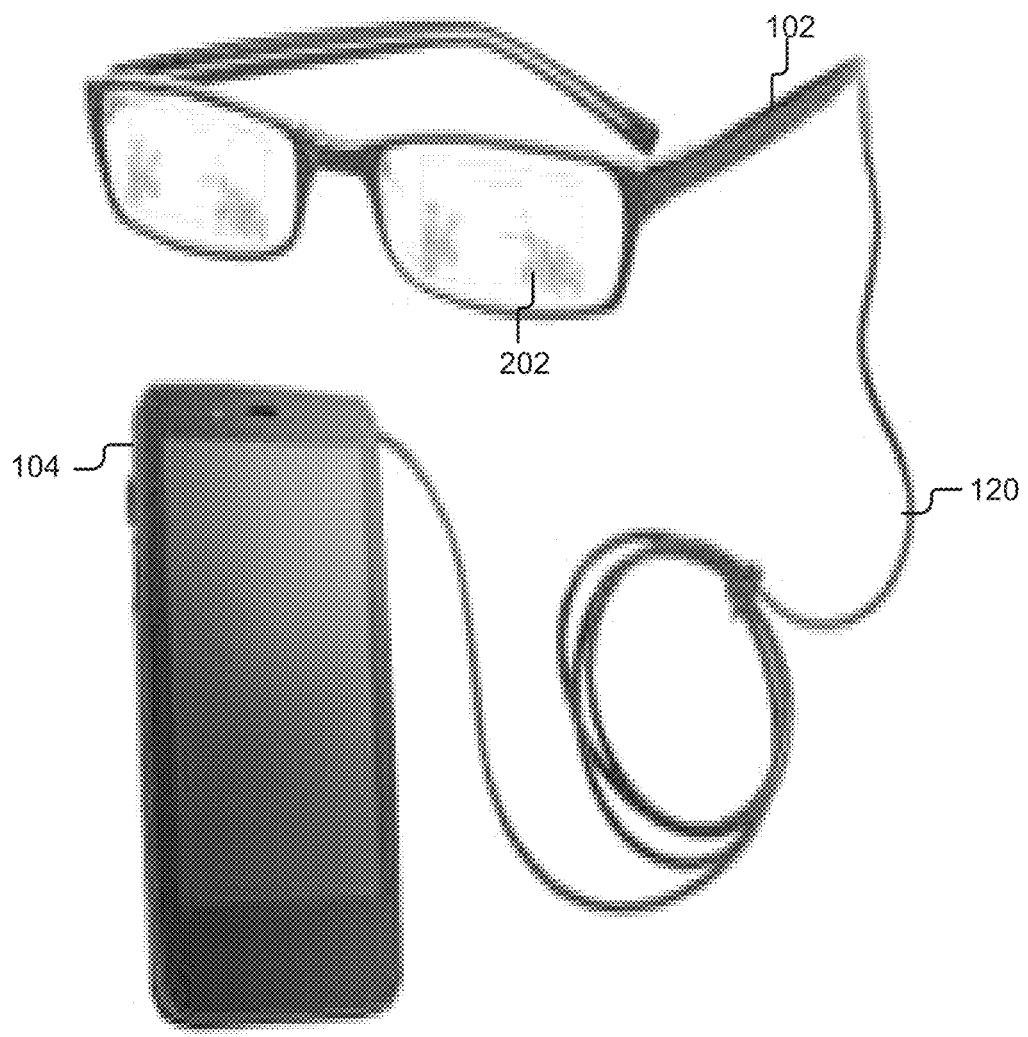
FIG. 2 is a perspective view of one embodiment of a wearable human interface module coupled to a computing and communication module.

FIG. 2 is a perspective view of one embodiment of a wearable human interface module 102 coupled to a computing and communication module 104 by signal line 120. In this embodiment, the wearable human interface module 102 has the form of eyeglasses. For example, the image delivery and display mechanism 302 may include a substrate 202 (e.g., a lens, or diffractive elements) and a projection system (not shown—See description of 302 below) for projecting information onto the substrate 202. In some embodiments, the substrate 202 is transparent or an optically transmissive substrate. Thus, when the user views an area through the substrate 202, it appears as if the projected information is overlaid over the wide field of view provided when viewing the area through eyeglasses. The wearable human interface module 102 preferably has a form, structure and weight similar to conventional eyeglasses; however, with the enhanced image delivery and display capabilities and the image, audio and environmental sensing capabilities that will be described in more detail below with reference to FIG. 3. It should be understood that FIG. 2 shows only one embodiment of the wearable human interface module 102. In other embodiments, the wearable human interface module 102 may take the form of a bracelet, a watch, a headset, etc. The signal line 120 in this embodiment includes optical relay fibers and electronic wires. The optical relay fibers provide display information to the wearable human interface module 102 from the computing and communications module 104. The electronic wires provide electronic signals and power between the human interface module 102 and the computing and communications module 104. In this embodiment, the computing and communications module 104 has the form and function similarly to a smart phone. For example, it includes a processor, memory with an operating system, the ability to communicate wirelessly using both voice and data channels, a camera, a microphone, and various other sensors. In some embodiments, the processor is a hardware processor, a controller or a microprocessor. In this embodiment, the computing and communications module 104 also has a form factor similar to that of a smart phone. However, it should be understood that the computing and communications module 104 may have other form factors similar to that of a bracelet, a pendant, watch, cell phone, or other wearable computing forms.

Figure 3:
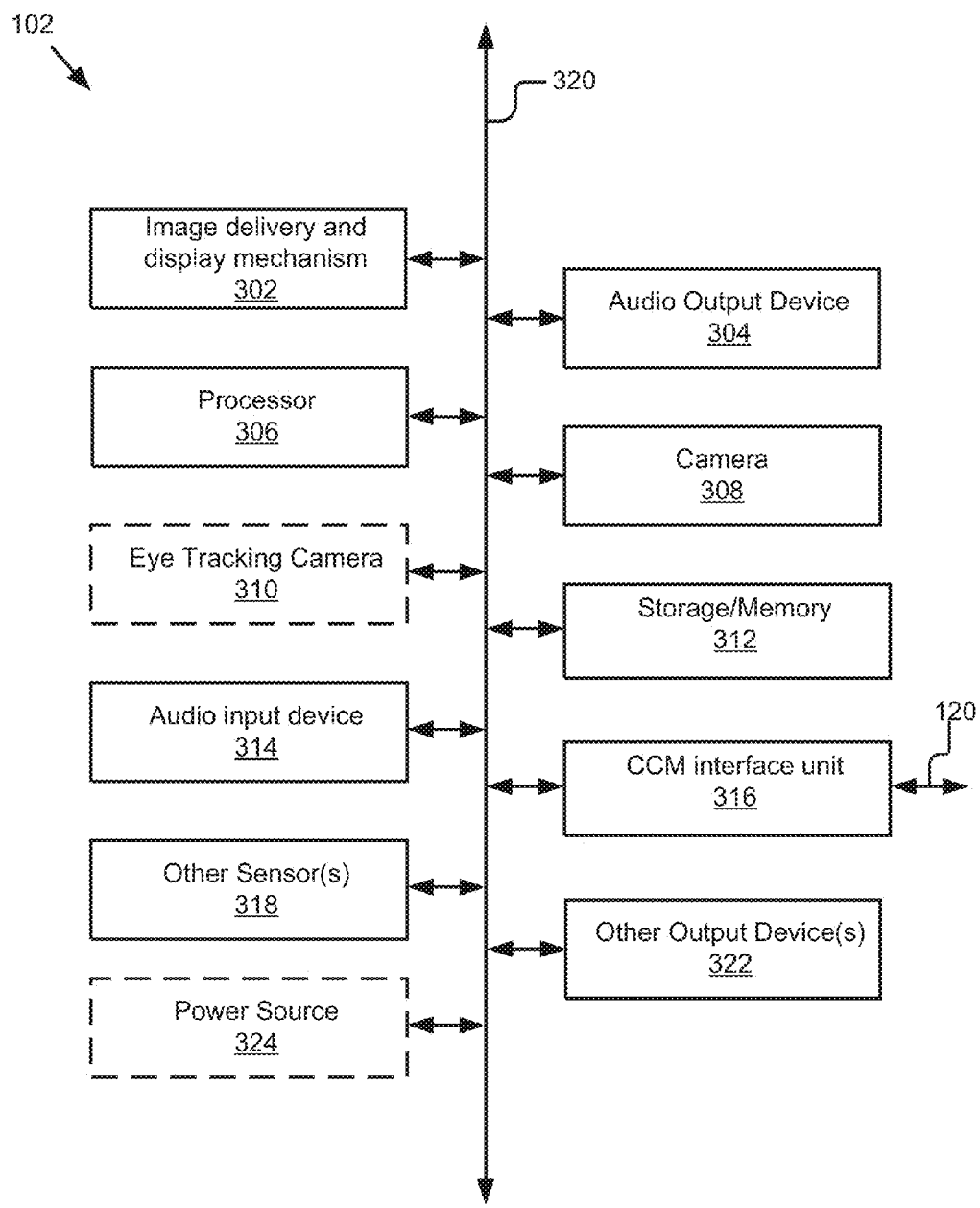
FIG. 3 is a block diagram of one embodiment of a human interface module.

FIG. 3 is a block diagram of one embodiment of the human interface module 102. In this embodiment, the human interface module 102 comprises: an image delivery and display mechanism 302, and audio output device 304, a processor 306, a camera 308, an eye tracking camera 310, storage or memory 312, and audio input device 314, a CCM interface unit 316, other sensors 318, other output devices 322 and a power source 324. These components of the human interface module 102 are communicatively coupled to a bus or software communication mechanism 320 for communication with each other.

The image delivery and display mechanism 302 is a system for providing a wide field of view to present large images, a binocular see-through (transparent) display, or display images in three dimensions. In one embodiment, the image delivery and display mechanism 302 includes a projection mechanism to display images in a virtual plane. In another embodiment, the image delivery and display mechanism 302 includes a projection system for in-eye projection of images. Example embodiments for the image delivery and display system 302 are shown and described below with reference to FIGS. 5-8B. In yet another embodiment, the images are projected onto the lenses of the glasses forming the human interface module 102. In still another embodiment, the image delivery and display mechanism 302 projects the image on the wall, desktop, tabletop or nearby surface. The image delivery and display mechanism 302 may include laser diodes, scanning fiber display, scanned light display, 3-D displays (stereoscopic, automultiscopic or volumetric), light field, substrate-guided optics, light-guided optical elements, etc. The image delivery and display mechanism 302 is coupled to receive image data for display. In one embodiment, the image delivery and display mechanism 302 receives optical signals directly from the CCM interface 316. In another embodiment, the image delivery and display mechanism 302 is coupled to the bus 320 and cooperates with the processor 306 and the CCM interface unit 316 to produce images for presentation. In some embodiments, the image delivery and display mechanism 302 includes adaptive optics to correct for the visual ability of the user so that the human interface module 102 can be used by anyone irrespective of whether they require prescription glasses. In yet another embodiment, the image delivery and display mechanism 302 cooperates with the other sensors 318 to detect the ambient light conditions and provide for control either automatically or under user control of per pixel opacity of display. It should be understood that other dimming mechanisms such as application of UV light or electrical signals to the glasses of the human interface module 102 may also be provided to make the display modulate the level of ambient light that enters the display. In particular, for medical or healthcare applications, the image and delivery mechanism 302 provides a see-through display with opacity that is selectable at the smallest display element (e.g., a pixel unit), and is fully controllable by the wearer mobile information gateway device 130.

The human interface module 102 is in general a wearable device that permits a scene adapted overlay of virtual information on the real world objects. Regardless of the specific embodiment, reference to the terms "overlays" or "overlaid" refers to scene adapted overlay. In the embodiment of the present invention, the image delivery and display mechanism 302 "overlays" information related to the first customer on a field of view or retrieved information is "overlaid" over a field of view. In other words, the user is able to see the real world that is not blocked by the overlay. In the preferred embodiment, the image delivery and display mechanism 302 is a see-through medium through which the real world can be seen by the eyes of the user and on which virtual objects can be displayed overlaid on top of or next to real objects. For example, this is overlay may be achieved with the image delivery and display mechanism 302 projecting information onto a substrate so that the projected information can be viewed on the substrate while the real world may be seen through the substrate. In a second embodiment, the image delivery and display mechanism 302 projects the information and the area behind it is made opaque occluding the real word behind it as much as possible, however, the portion of real world that is not blocked by the projected overlay can be seen by the user. Given the entire scene information, the image delivery and display mechanism 302 selects specific means of rendering, e.g. high luminance contrast, or color contrast, font style/size and type, etc., so the projected information is visible against a background of the real world. The overlaid virtual object can completely block the light reflected from the real object or can partially transmit light. In still another embodiment, the real world is capture with a camera and information is digitally overlaid over a video captured by the camera and presented to the user.

The audio output device 304 is coupled to the bus 320 to receive audio signals and generate sound. The audio output device 304 may include earphones, speakers, a bone conducted speaker or transducer, or an audio output jack for coupling to external speaker sources. The audio output device 304 generates sound and outputs it to the user of the human interface module 102. The audio output device 304 is responsive to signals from the processor 306 or the CCM interface unit 316. For example, the audio output device 304 may output scrambling audio signal that makes the voice of the customer incomprehensible to a third person other than the teller for privacy concerns.

The processor 306 may include an arithmetic logic unit, a microprocessor, a general purpose controller or some other processor array to perform computations and other operations for the human interface module 102. The processor 306 is coupled to the bus 320 for communication with the other components. Processor 306 processes data signals and may include various computing architectures including a complex instruction set computer (CISC) architecture, a reduced instruction set computer (RISC) architecture, or an architecture implementing a combination of instruction sets. Although only a single processor is shown in FIG. 3, multiple processors may be included.

The camera 308 may be an image capture device. The camera 308 is preferably forward facing having a field of view similar to the user's perspective when wearing the human interface module 102 (e.g., glasses). The camera 308 may be an HD camera, a regular 2D video camera, a multi-spectral camera, a structured light 3D camera, a time-of-flight 3D camera, or a stereo camera, etc. The camera 308 is capable of capturing images and providing those images to the processor 306 and the storage memory 312 so that the human interface module 102 can sense and recognize gestures, recognize and authenticate customers, perform facial recognition, perform face/skin tone recognition, and interpret the real world scene. The camera 308 is coupled to the bus 320 to provide images and other processed metadata to the processor 306, the storage or memory 312 or the CCM interface unit 316.

The eye tracking camera 310 is similarly an image capture device. The eye tracking camera 310 is inward facing towards the face of the user of the human interface module 102. The eye tracking camera 310 has enough resolution to capture the eye movement, gaze direction, and iris detail of the user. The eye tracking camera 310 is coupled to the bus 320 to provide information to the processor 306, the storage or memory 312, or the CCM interface unit 316. The images captured by the eye tracking camera 310 can be used to determine eye gaze direction and movement for one or both eyes and translate it into control or other inputs to the human interface module 102. The images captured by the eye tracking camera 310 can also be used to identify and authenticate the user such as by sending the images to the backend service server 108 or the computing and communications module 104 for iris detection and recognition. In some embodiments, the eye tracking camera 310 is optional.

The storage or memory 312 stores instructions and/or data that may be executed by the processor 306. The memory 206 is coupled to the bus 320 for communication with the other components. The instructions and/or data may include code for performing any and/or all of the techniques described herein. The memory 312 may be a dynamic random access memory (DRAM) device, a static random access memory (SRAM) device, flash memory or some other memory devices. The memory 312 may store and operating system, applications and other software modules executable by the processor 306.

The audio input device 314 may be a microphone or similar device for capturing audio signals in the environment in which the human interface module 102 is used. The audio input device 314 may also be used for capturing voice and other sounds near the human interface module 102. The audio input device 314 is coupled by the bus 320 to provide these signals for additional processing by the processor 306 or for storage in the memory 312. For example, the audio input device 314 can be used to capture signals that can be used for voice recognition. The signals can be used for identification or authentication of the user or to input commands or data.

The CCM interface unit 316 is electronics and other hardware to facilitate communication between the human interface module 102 and the computing and communication module 104. The CCM interface 316 is coupled to the bus 320 for communication with the other components of the human interface module 102. The CCM interface 316 is also coupled to signal line 120 for communication with the computing and communication module 104. As will be described in more detail below, the CCM interface 316 may provide power, optical signals, and electrical signals between the human interface module 102 and the computing and communications module 104. In some embodiments, the CCM interface unit 316 may include other communication devices to allow the human interface module 102 to communicate with the computing and communications module 104 or other devices such as via Bluetooth, Wi-Fi or other standard communication protocols.

The human interface module 102 also includes one or more other sensors or input devices 318. For example, the other sensors 318 may include: a finger operated touch panel, motion sensors such as a 3-axis gyroscope, a 3-axis accelerometer, a 3-axis magnetometer, an ambient light sensor, a thermal sensor, environmental sensors (for pollution or radiation), proximity sensor, RF detector, a GPS sensor, a head tracker, brainwave sensor, buttons, intelligence self-powered sensors, credit card reader, biometric sensors such as pulse rate, breathing rate, perspiration and other sensors for lie detection type identification. The one or more other sensors or input devices 318 are coupled to the bus 320 to provide the signals to the processor 306.

The other output devices 322 may be coupled to bus 320 to provide additional feedback to the user. For example, other output devices 322 to provide haptic feedback may be included as part of the human interface module 102.

In some embodiments, another output device 322 is an illumination device such as an ultraviolet light source. The illumination device may be selectively activated in conjunction with a security system to authenticate the genuineness of currency, identification cards and other documents. It should be understood that an ultraviolet light source is merely one example of another output device 322. Other output devices 322 may include various other types of output devices used for counterfeit detection. The illumination device can be used in conjunction with the camera 308 such that the camera 308 captures an image of the currency, identification card or other document in view of the human interface module 102 while the illumination device is activated. The image captured by the camera 308 while the illumination device is activated can then be image processed by the security system to determine whether the document is genuine or counterfeit. For example, many currencies have a security thread or other markings that become more visible under ultraviolet light. In other embodiments, counterfeit detection does not require the illumination device, but rather image processing may be performed by the human interface module 102, the computing and communication module 104 or the backend service server 108 upon images of documents captured by the human interface module 102. This is similar to picture analysis performed by certain high-end photocopiers. If the document is counterfeit, a signal can be generated and sent to the human interface module 102, other human interface modules, or various other systems. In some embodiments, this process happens automatically without the wearer of the human interface module 102 knowing that a counterfeit has been detected. In other embodiments, the illumination device is selectively activated while the user of the human interface module 102 is inspecting the document, so that the security features in the document are immediately identifiable by the wearer of the human interface module 102. Depending on the embodiment, the security system that interacts and controls the illumination device may be part of the human interface module 102, the computing and communication module 104, or the backend service server 108. In one embodiment, the security system is software or routines operable on any one of these or a combination of these components 102, 104 and 108.

In still other embodiments, the output device 322 is night vision mechanism or even a conventional light source such as LEDs. The night vision mechanism may be an image intensification system that provides an enhanced image of the scene through the human interface module 102 to the user. Alternatively, the night vision system may include active illumination such as a near infrared or shortwave illumination and a lowlight camera. In yet another embodiment, the night vision mechanism may be a thermal imaging system to provide a thermal image of the scene to the user via the human interface module 102.

The output device may have a NIR illuminator used for iris recognition.

The power source 324 may be a battery. In some embodiments, the battery may be rechargeable or replaceable. As noted above, in some embodiments, the CCM interface unit 316 provides power to operate the human interface module 102. In such a case, the power source 324 is optional and thus FIG. 3 with dashed lines.

It should be understood that other processors, operating systems, sensors, displays and physical configurations are possible for the human interface module 102. For example, the human interface module 102 may also include a light source (not shown).

Figure 4A:
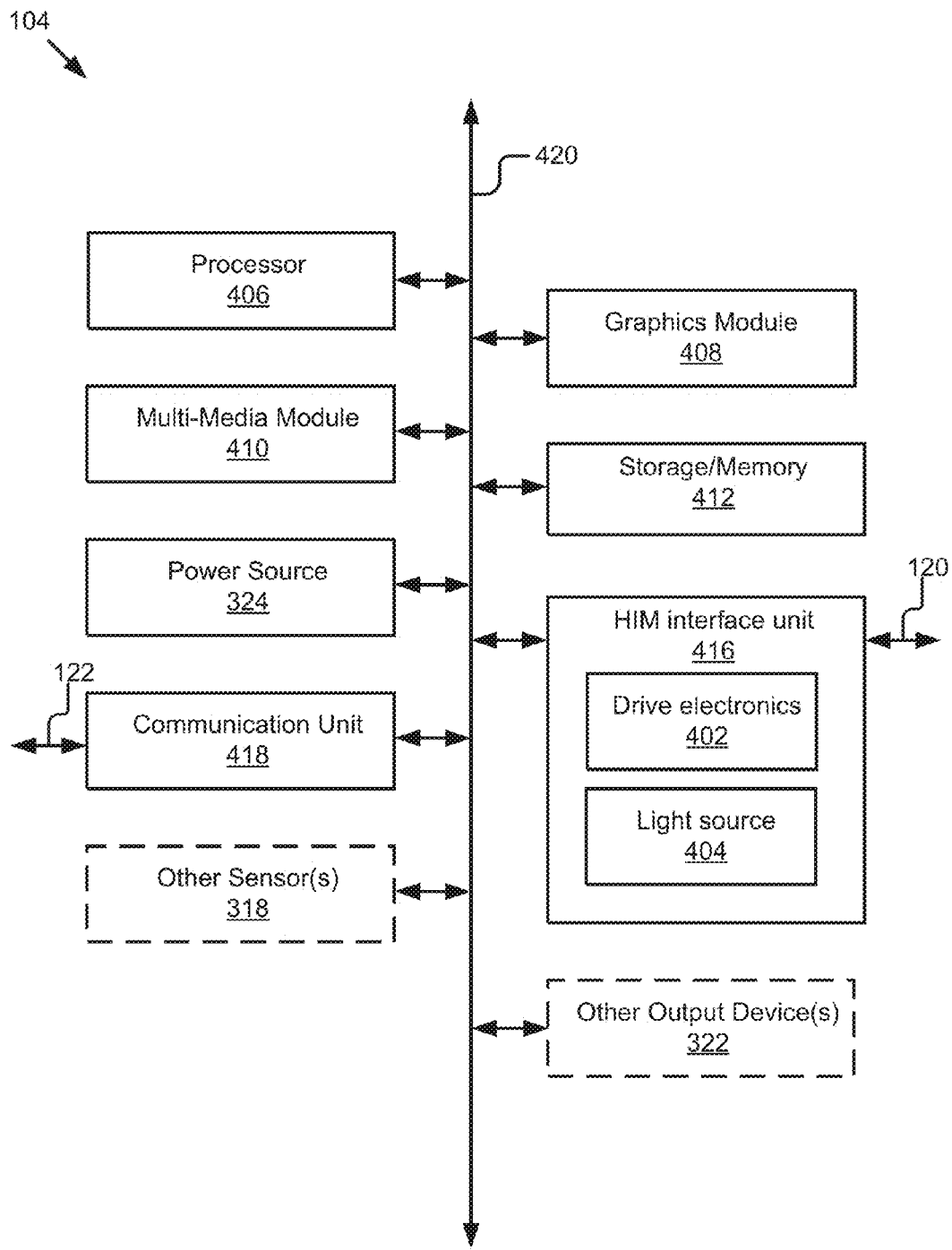
FIG. 4A is a block diagram of one embodiment of a computing and communication module.

FIG. 4 is a block diagram of one embodiment of a computing and communications module 104. In this embodiment, the computing and communications module 104 comprises: a processor 406, a graphics module 408, a multimedia module 410, storage or memory 412, a power source 324, HIM interface unit 416, a communications unit 418. The HIM interface unit 416 may include drive electronics 402 and a light source 404. These components of the computing and communications module 104 are communicatively coupled to a bus or software communication mechanism 420 for communication with each other. In some embodiments, the computing and communications module 104 may optionally include other sensors 318 and other output devices 322.

It should be understood that in general, the components of the computing and communications module 104 have greater performance and speed than the similar components of the human interface module 102. The human interface module 102 and the computing and communications module 104 are able to divide or partition processing responsibility such that the human interface module 102 is responsible primarily for creating interfaces and affordance that allow users to interact with existing information in new ways and thereby provide better and new services to the customer as well as new ways of interacting with information collectively. The computing and communications module 104 is primarily responsible for assisting the human interface module 102 with processing of information and facilitating faster communication with other resources. It should be understood that there may be a variety of other divisions of labor between the human interface module 102, the computing and communications module 104 and the backend service servers 108 other than those described herein. However, those other organizations are contemplated by the present disclosure and the specific division of labor can be adapted to the specific application or business context in which the mobile information gateway 100 is being used.

In some embodiments, the computing and communications module 104 may include a gesture interface to input controls, commands and data. Also, the computing and communications module 104 may serve as an "adapter" or interface to other devices and systems, such as probes, medical devices, bank teller equipment, light pen, pointer or any other specialized equipment for a particular business vertical. In some embodiments, the computing and communications module 104 may be responsible for rendering the visual information and the human interface module 102 may be responsible for only displaying the rendered data. In some embodiments, the computing and communications module 104 may decode, transcode, decompress or decrypt image, video or audio data before sending it to the human interface module 102.

In general, most computation should be performed on the computing and communications module 104. The human interface module 102 should perform a minimal amount of computation on its sensors and output devices. Its computation will mostly involve capturing images, audio signals, and/or other information, compressing them if necessary, and transmitting them to the computing and communications module 104 for further processing.

The processor 406 is similar to that described above with reference to FIG. 3, so that description will not be repeated here. However, the processor 406 may have greater processing capabilities and functionality.

The graphics module 408 is coupled to the bus 420 and cooperates with the processor 406 to generate graphic images that can be presented at the human interface module 102. The graphics module 408 in this embodiment is a hardware device and in alternate embodiments may be software storable in the memory 412, or a combination of hardware and software.

The multimedia module 410 is coupled to the bus 420 and cooperates with the processor 406 to produce multimedia for display at the human interface module 102. The multimedia module 410 in this embodiment is a hardware device that cooperates with the processor 406 to perform some of the computational task required in processing video. However, in other embodiments, the multimedia module may be software stored on the memory 412 executable by the processor to achieve the same functionality or maybe a combination of hardware and software. It should be understood that the processor 406, graphics module 408 and the multimedia module 410 may be integrated as a system-on-chip (SoC).

Figure 4B:
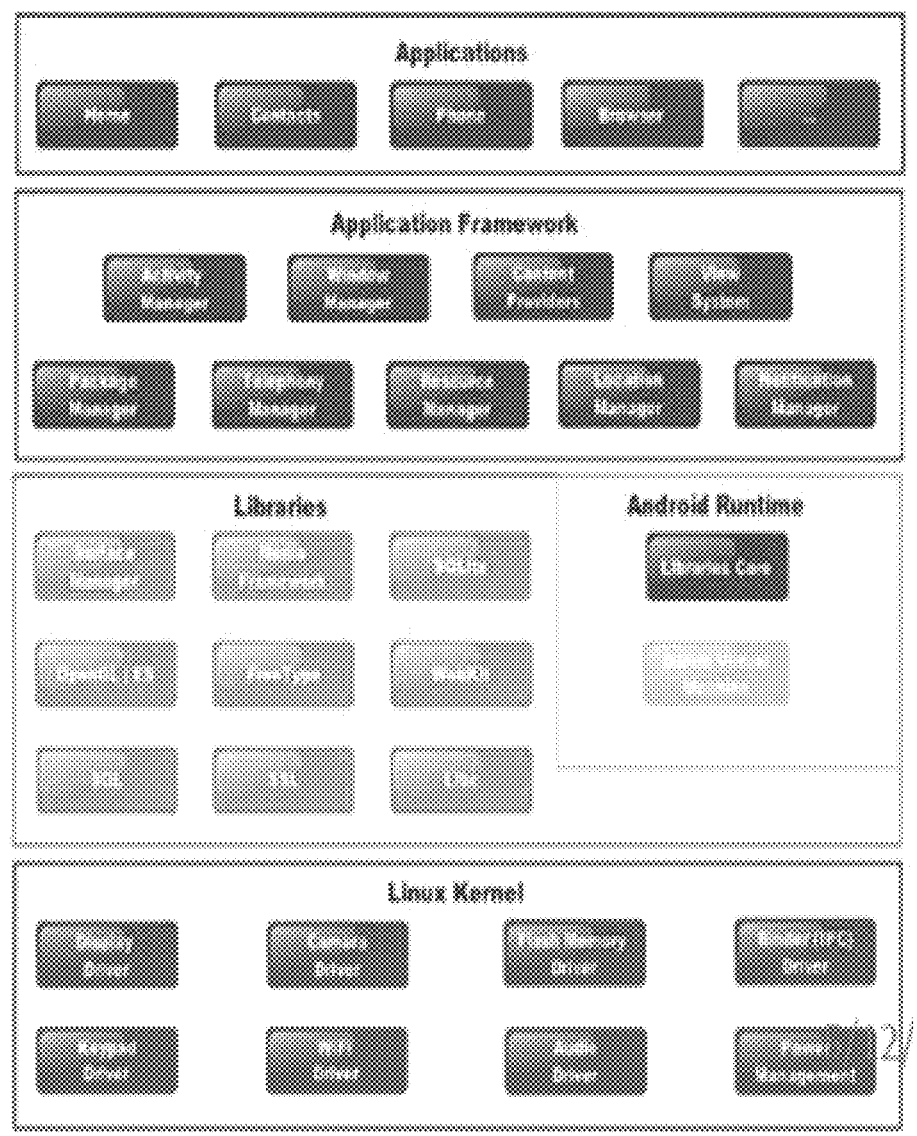
FIG. 4B is a block diagram of example software modules stored in the memory of the computing and communication module.

The storage or memory 412 is similar to that described above for the human interface module 102. However the memory 412 may also include storage since the form factor for the computing and communications module 104 provides more area. In addition to being flash memory, in some implementations, the storage or memory 412 may also include a non-volatile memory or similar permanent storage device and media, for example, a hard disk drive, or some other non-volatile storage device. The storage or memory 412 stores and operating system, applications, libraries and other information used by both the computing and communications module 104 and the human interface module 102. A diagram of example software modules (e.g., a high level operating system, specifically Android by Google Inc. of Mt View, Calif.) stored in the memory 412 is shown in FIG. 4B.

The power source 324 is preferably a battery or some other rechargeable power source capable of supplying required for the computing and communications module 104.

The HIM interface unit 416 is electronics and other hardware to facilitate communication between the computing and communication module 104 and the human interface module 102. The HIM interface unit 416 is coupled to the bus 420 for communication with the other components of the computing and communication module 104. The HIM interface unit 416 is also coupled to signal line 120 for communication with the human interface module 102. In some embodiments, the HIM interface unit 416 provides power, optical signals, and electrical signals from the computing and communication module 104 to the human interface module 102. The HIM interface unit 416 may include drive electronics 402 and the light source 404 to generate and send optical signals to the human interface module 102. The HIM interface unit 416 may also send data and commands to and receive from data and commands from the human interface module 102.

The computing and communication module 104 may include other sensors 318 and other output devices 322. These may be the same as described above for the human interface module 102 or maybe subsets of the sensors 318 and output devices 322 described above.

Figure 5:
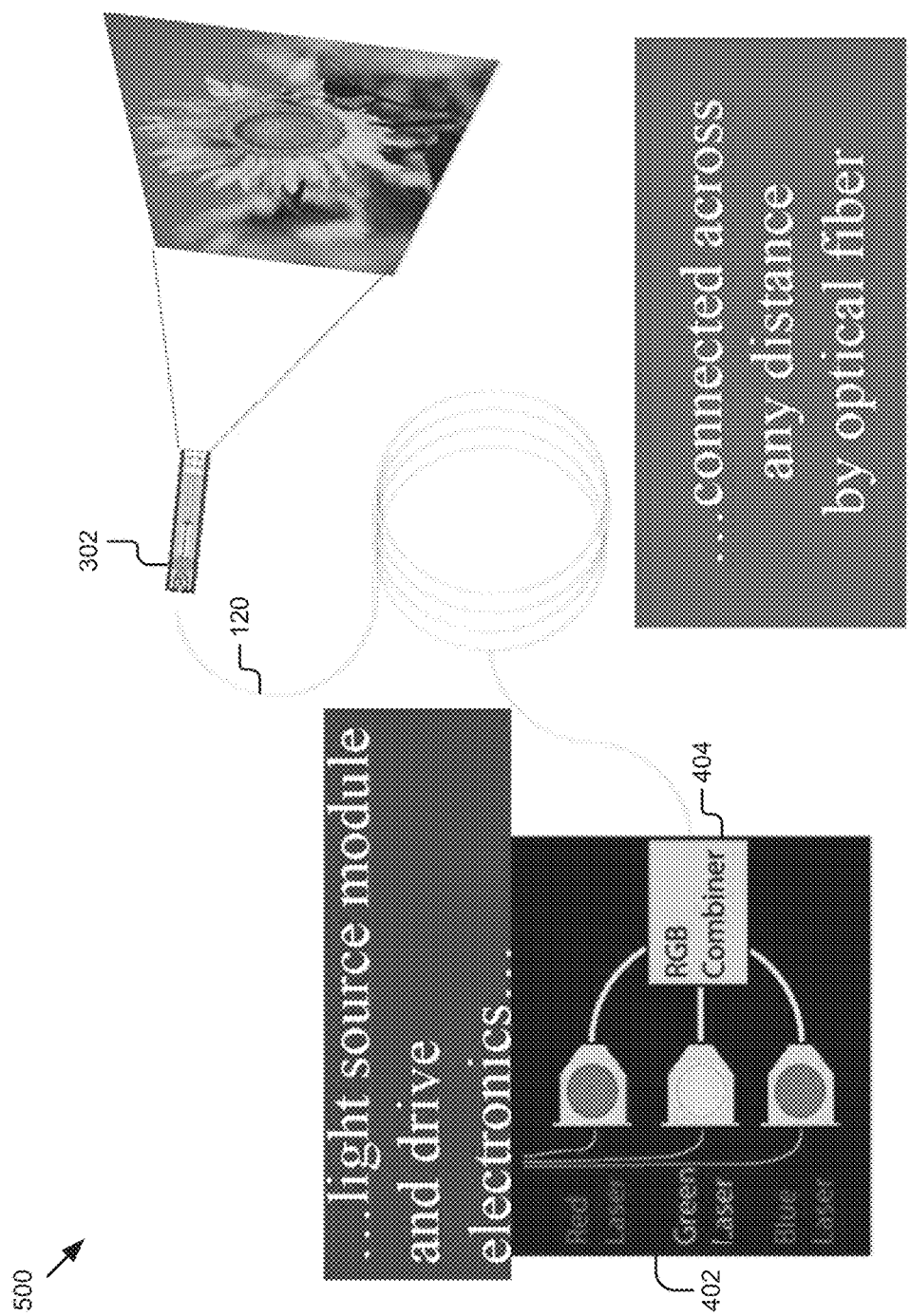
FIG. 5 is a diagram of one example for light source, drive electronics, coupling and image delivery and display mechanism.

Referring now to FIG. 5, one example for light source 402, drive electronics 404, signal line 120 and the image delivery and display mechanism 302 are shown. In this example, the light source 402 is a plurality of lasers, i.e., a red laser, a green laser, and a blue laser. The outputs of these lasers are provided to the drive electronics 404, which is an RGB combiner to generate images that are sent as light through signal line 120. In this case signal line 120 is an optical fiber that couples the RGB combiner 404 with the image delivery and display mechanism 302. The image delivery and display mechanism 302 then projects the images so that they are visible to the user of the human interface module 102.

Figure 6:
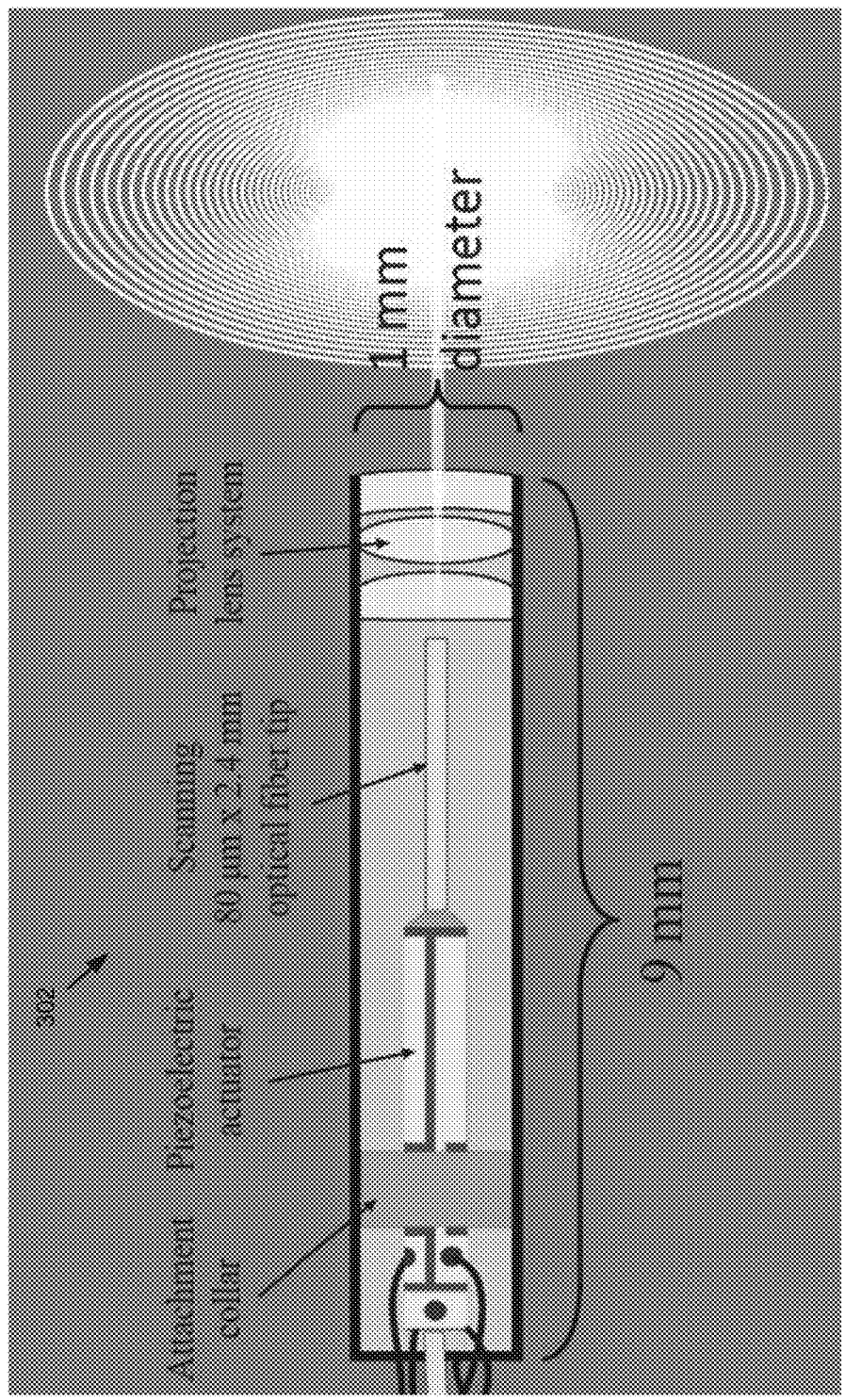
FIG. 6 is a diagram of one example of the image delivery and display mechanism.

Referring now to FIG. 6, one example of the image delivery and display mechanism 302 is shown. The image delivery and display mechanism 302 is coupled to the optical fiber 120 and includes a scanning fiber projection engine. The scanning fiber projection engine has a piezo-electric actuator coupled to an optical fiber tip directed to lens projection system to output the images received from the drive electronics onto a virtual plane. In particular, FIG. 6 illustrates how the image delivery and display mechanism 302 can be constructed at a very small scale (e.g. less than 9 mm) such that the image delivery and display mechanism 302 could be integrated into the glasses of FIG. 2.

Figure 7:
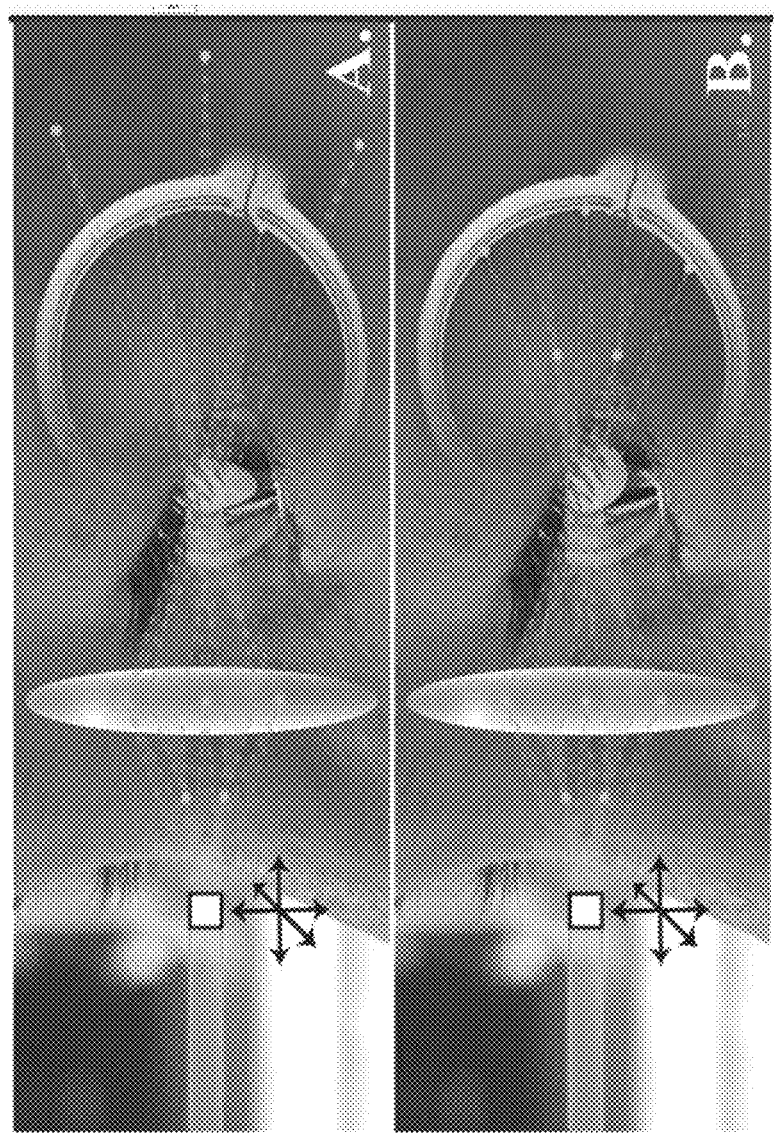
FIG. 7 is a diagram of one example of in eye projection of a 3-D display.
Figure 7:
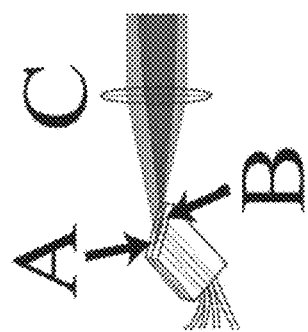

FIG. 7 is shows one example of in eye projection of a volumetric 3-D display. FIG. 7 illustrates how the image delivery and display mechanism 302 could be configured in position on an eyeglass frame to project a volumetric 3-D display onto the retina of the user. In such an example, the image delivery and display mechanism 302 scans a fiber bundle with a mirror scanner and then use the lens system to project the image to the user.

Figure 8A:
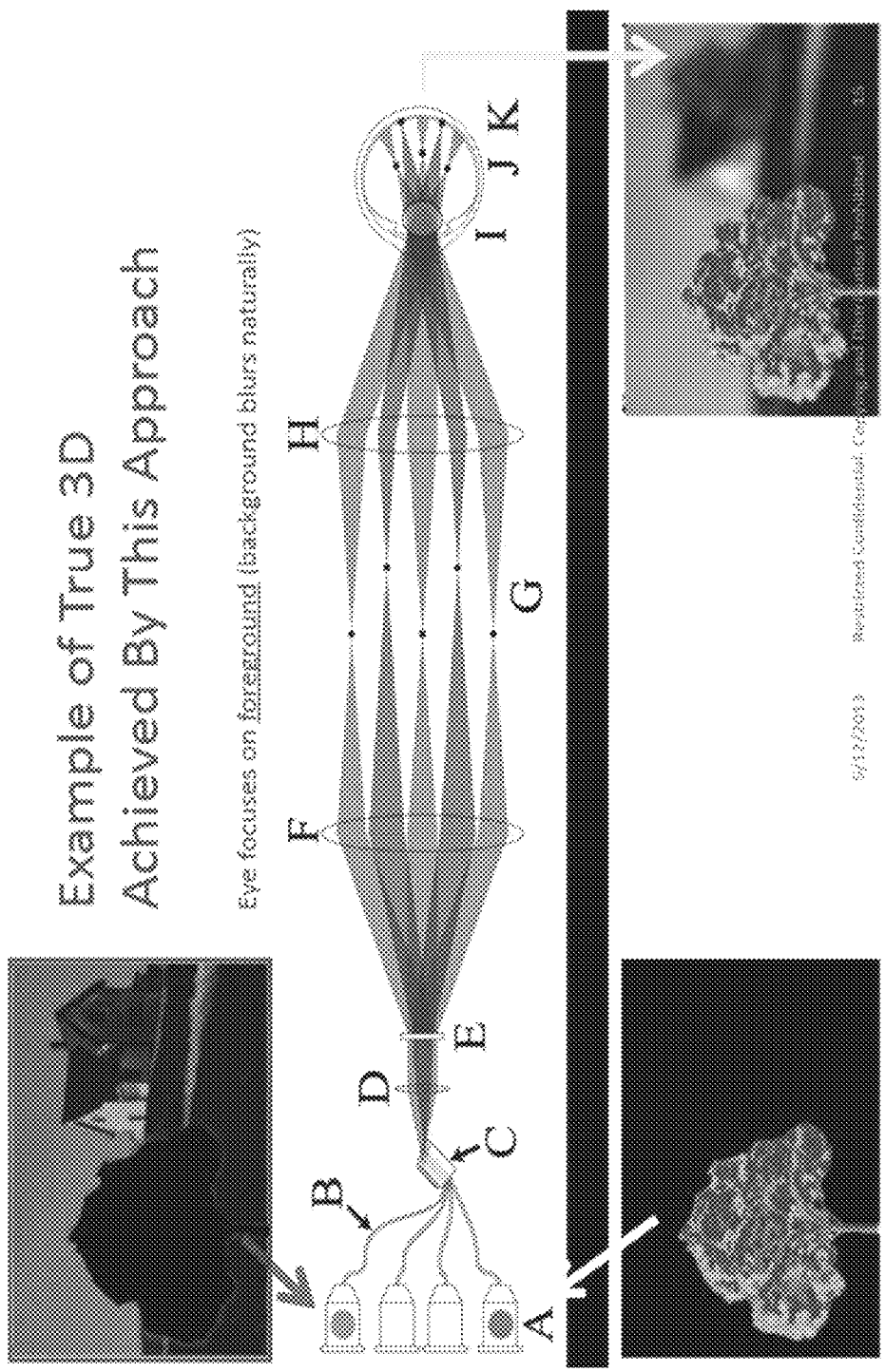
FIGS. 8A and 8B are diagrams of one example of true 3-D display provided by in eye projection.
Figure 8B:
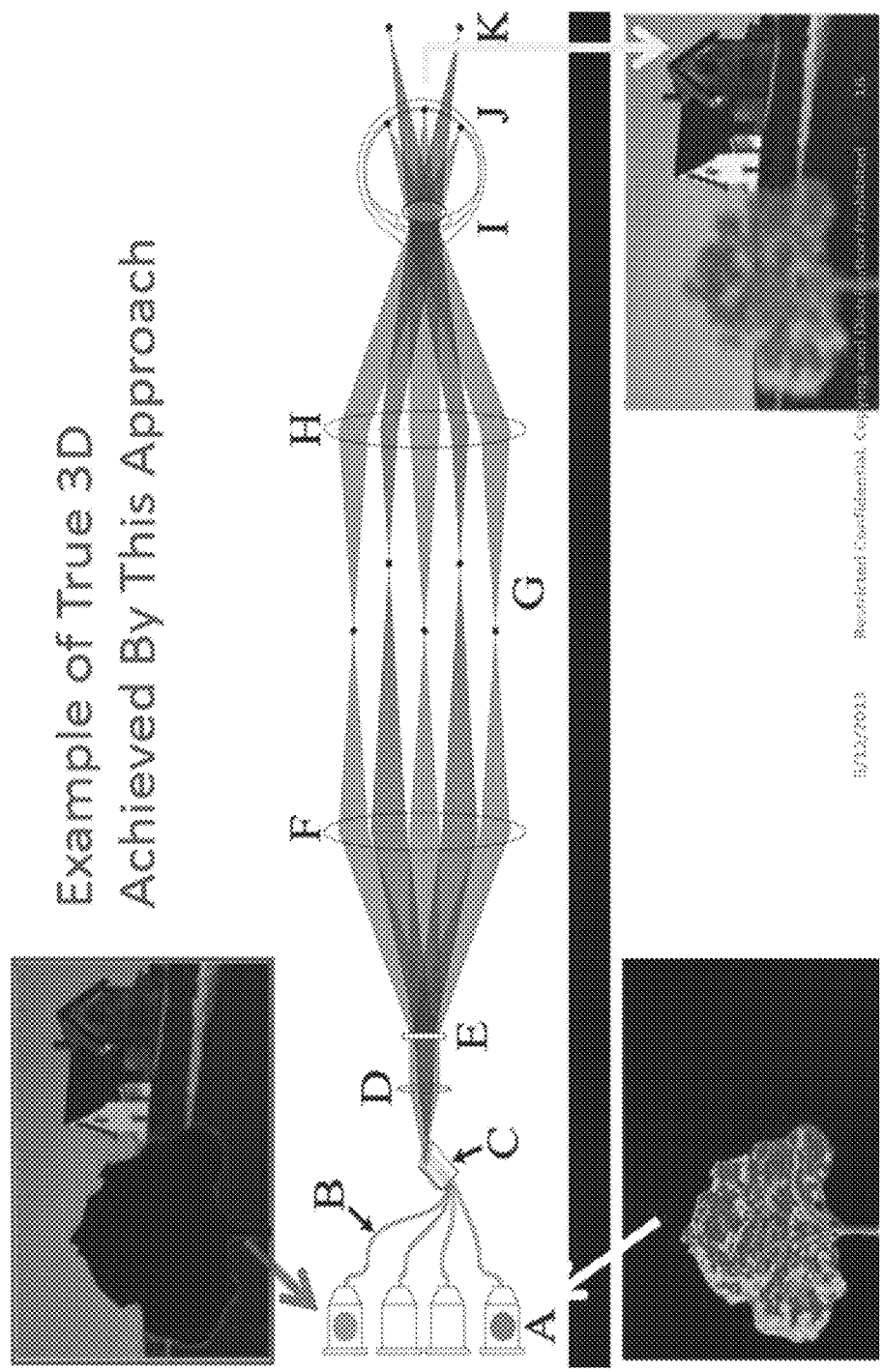

FIGS. 8A and 8B show one example of true 3D display provided by in eye projection. These figures illustrate how true 3D display may be achieved by in eye projection of images. The image delivery and display mechanism 302 includes a fiber bundle, a mirror scanner, and lens system to project images onto the retina of the user. FIG. 8A illustrates the image perceived by the user when focusing upon the foreground. FIG. 8B illustrates the image perceived by the user when focusing upon the background.

Method for Customer Interaction Using Mobile Information Gateway (e.g., for Financial Services)

Figure 9:
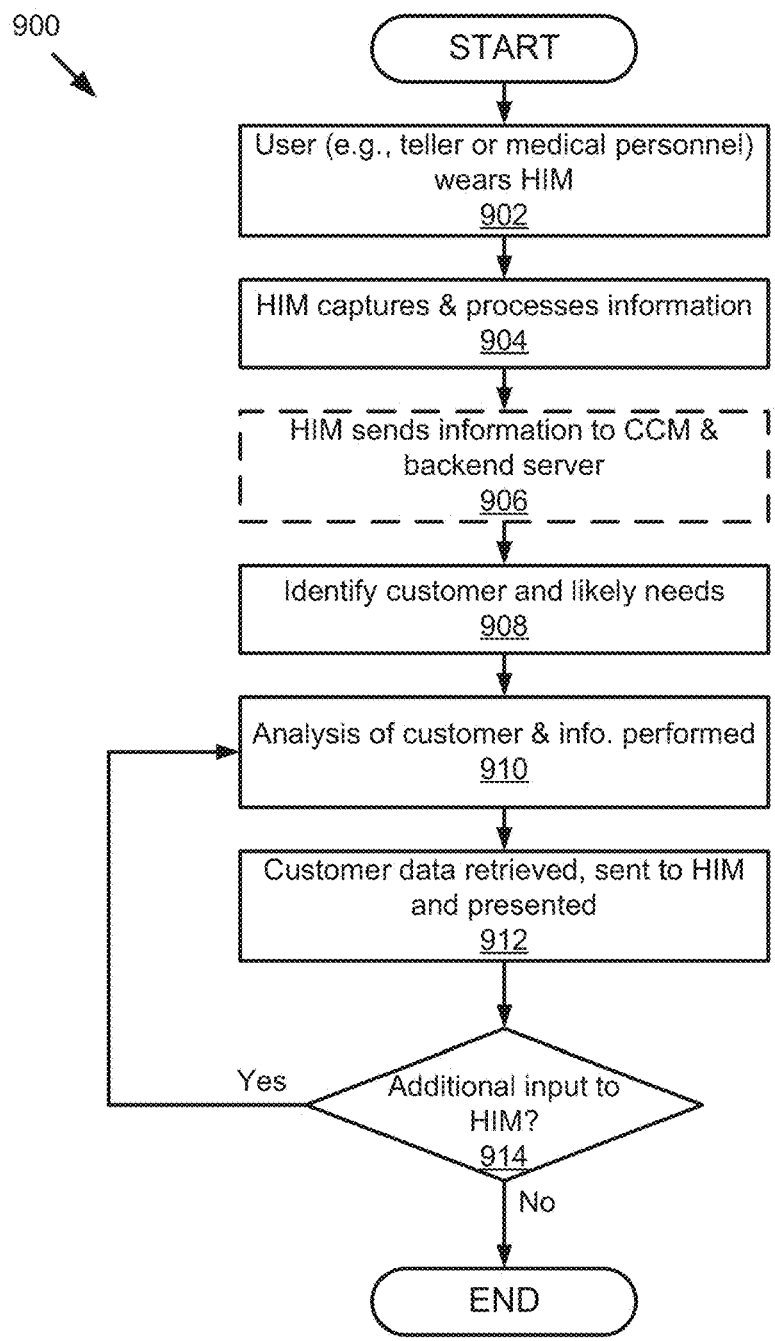
FIG. 9 is a flow chart of one embodiment of a method for asymmetrical use of the mobile information gateway.
Figure 10:
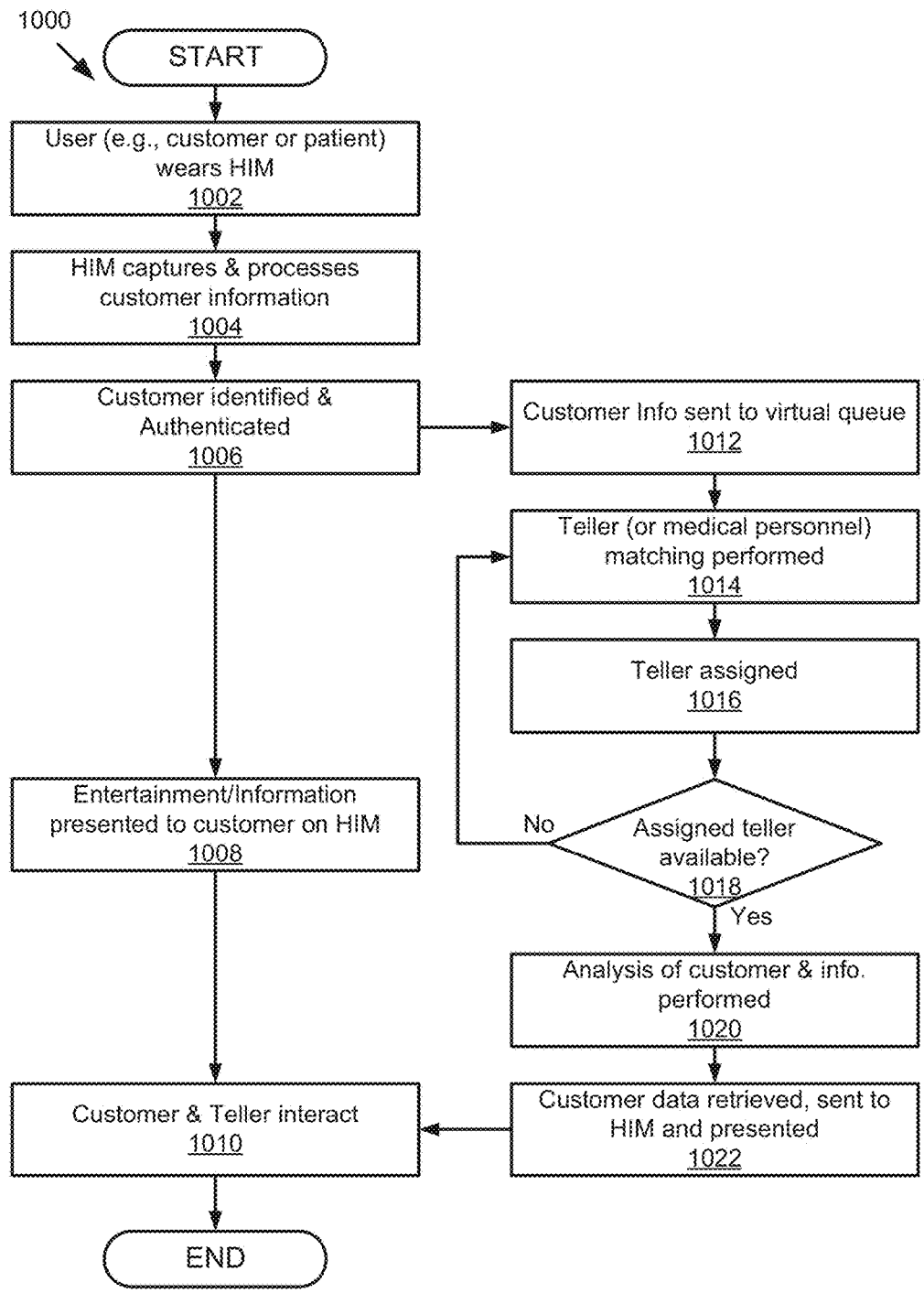
FIG. 10 is a flowchart of one embodiment of a method for symmetrical use of the mobile information gateway implementing a virtual queue.
Figure 11:
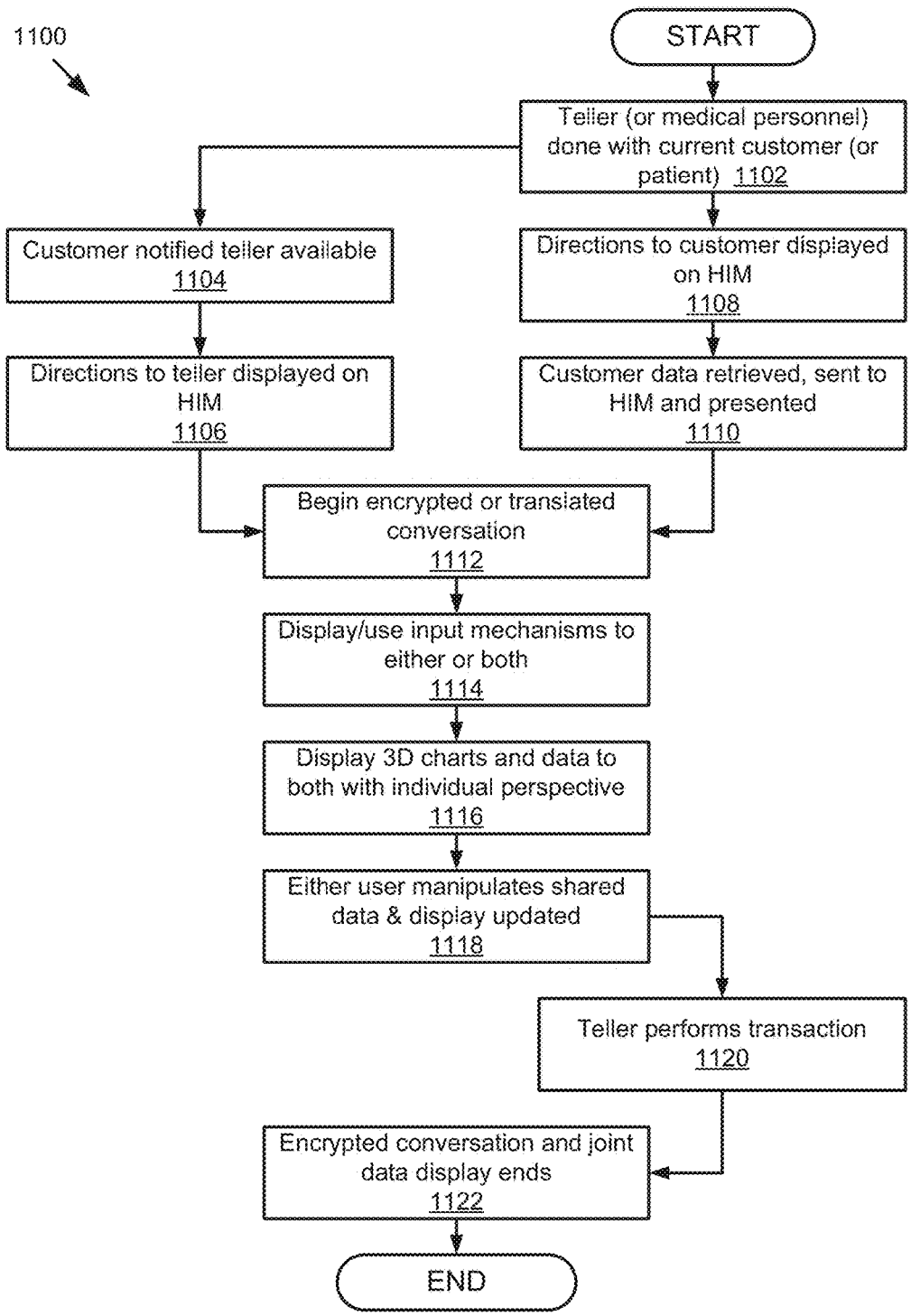
FIG. 11 is a flowchart of one embodiment of a method for symmetrical use of the mobile information gateway for servicing a customer using plurality of human interface modules.

Referring now to FIGS. 9-11, the methods of the present invention will be described in more detail. In general, there are two use cases for the present invention. First, in the asymmetrical case, a first user (e.g., a service representative or teller) is wearing the human interface module 102 and carrying the computing and communications module 104. The first user is interacting with a second user (e.g., a customer). The second user is not using or wearing a human interface module 102 or carrying the computing and communications module 104. Second, in the symmetrical case, both the first user and the second user are wearing and carrying their own respective human interface module 102 and computing and communications module 104. Other cases where more than two users each have their own human interface module 102 and the computing and communications module 104, and work together collaborative using new cooperation models and paradigms offered by the presented invention are considered extensions of the symmetrical case. FIG. 9 below describes a general method for the asymmetrical case where the first user, a teller or medical personnel, is wearing the human interface module 102 and carrying the computing and communications module 104. FIGS. 10 and 11 below describe methods for the symmetrical case where both the first user and the second user are wearing and carrying their own respective human interface module 102 and computing and communications module 104.

Furthermore, the methods of the present invention will now be described in the context of the specific vertical application of banking and financial services, in particular receiving services at the branch of a bank. This description is merely by way of example for illustration purposes and not by way of limitation. The methods of the present invention may be applied to other verticals such as medicine, law, retail, public services, etc. and the context of the operation of the methods is not intended to limit the human interface module 102 and the computing and communications module 104.

It should be understood that the method described above with reference to FIGS. 9-11 only identify some of the ways in which the human interface module 102 and the computing and communication module 104 allow the teller to provide enhanced services that are more tailored to the specific customer with which the teller is interacting. The human interface module 102 and the computing and communication module 104 may also be used to: provide any customer information and display it to the teller and/or the customer; provide a virtual teller; provide a service recommendation engine; provide customer-teller matching; provide a private communication channel between the teller in the customer; record/monitor delivery of services by tellers including active intervention to train or correct teller behavior; provide immediate feedback on service wait times and eliminate queues; and provide a new service model including a greeter/triage person and a problem solver person.

Referring now to FIG. 9, one embodiment of a method 900 for asymmetrical use of the mobile information gateway is described. As noted above, the method will be described in the context of a service representative, teller or medical personnel wearing the human interface module 102 and carrying the computing and communications module 104 interacting with a customer or patient not having or using a dedicated human interface module 102 and computing and communications module 104. Use of the human interface module 102 and the computing and communications module 104 by the teller provides a number of significant advantages. First, the teller may assist the customer anywhere and in any way inside the branch since they are not constrained to working with a desktop computer or terminal—this functionality is provided by the human interface module 102 and the computing and communications module 104. In the medical use case, this means that the medical personnel may use the mobile information gateway device 130, in a clinic, in a hospital, at the patient's home, or even at remove areas from the clinic or hospital. This completely eliminates the requirement that any customer wait in any queue to be served. Second, the teller can perform existing services every time because the human interface module 102 and the computing and communications module 104 enable identification (iris identification), authentication and retrieval of customer information in ways not possible with existing verification data systems. For example, today if you forget your ATM card or don't have any identification you can only do a subset of activities, e.g., you can deposit a check but not discuss any particulars about your account (you may not even be able to make a deposit if you do not know your account number). With the teller having the human interface module 102 and the computing and communications module 104, all customers are automatically authenticated (through iris detection) and can be served fully as they need. Third, the teller can provide enhanced level of services because the human interface module 102 and the computing and communications module 104 allow the teller to access the relevant information about the customer and the bank's services are readily available in front (virtually) of the teller. Sophisticated analytics and recommendation engines can be used to provide pertinent options and guidance to the teller in real-time while they are interfacing with the customer— e.g., "customer has just won the lottery or received a large sum of money and it might be a good time to remind him of our investment services."

The method 900 begins with the user (e.g., teller or medical personnel) wearing 902 the human interface module 102. In the embodiment shown in FIG. 2, the user would wear the glasses including the human interface module 102 and also carry the computing and communications module 104. In other embodiments, the computing and communications module 104 may be positioned proximate to the human interface module 102 and coupled for communication and cooperation. Next, the human interface module 102 captures and processes 904 information. For example, the eye tracking camera 310 captures an image that is used by the human interface module 102, the computing and communications module 104, the backend service server 108 or combinations thereof to recognize the teller, authenticate the teller, authorize her to perform particular actions, and insert her into a list of persons available to service customers. Similarly the camera 308 may capture images of customers in the branch or entering the branch. In some embodiments, the human interface module 102 may perform some processing of the images to prepare them for distribution or perform initial steps of other types of processing. In some embodiments, the human interface module 102 is capable of doing all the processing and blocks 908, 910, 912 and 914 are performed by the human interface module 102. In such cases, step 906 is optional. However, in other embodiments the processing of information is divided among the computing and communication module 104 and/or the backend server 108. In such embodiments, the human interface module 102 sends 906 the captured information to the computing and communication module 104 and/or the backend server 108 as necessary.

The method 900 continues by identifying 908 the customer and her/his likely needs. The images captured by the human interface module 102 may be processed to identify and authenticate the customers as a particular individual. In some embodiments, the computing and communication module 104 and/or the backend server 108 process the captured information to determine an identity of the customer. The recognition may be rough approximations as to which customer has a matching identity or it may be very specific identifying a particular individual by name and other attributes. For example, facial recognition, iris recognition, facial/tone recognition may be performed on the images. The images may also be processed to identify what the customer likely needs. For example, if the customer is holding a check, information suggesting that the customer wants to make a deposit may be sent and displayed on the human interface module 102. The analysis of what the customer likely needs may also be determined from information about the customer's accounts, recent transactions, information about the customer generally available on the Internet or information about the customer available in social networks. Furthermore, identifying 908 the customer may include determining the location of the customer within the bank branch. The backend service server 108 may be in communication with the location server or access to location services that can be used to provide a specific location of the customer within the bank branch. This information may be retrieved by the backend service server 108 and transmitted for display on the human interface module 102. The identification of the customer and her needs based on an image captured by the human interface module 102 may be performed entirely on the human interface module 102, entirely on the backend service server 108, entirely on the computing and communications module 104 or cooperatively amount two or more them.

The method 900 continues to perform analysis 910 of the customer and the information received. For example, the customer and her likely needs may be provided to a service recommendation engine. The service recommendation engine can generate a recommendation for product or service based upon the detected state of the customer via the human interface module 102 and/or data about the user in the computing and communications module 104 or the backend service server 108. The service recommendation engine advantageously generates recommendations and provides up selling opportunities for additional or related service that are specifically adapted to the customer based upon the information captured and processed by the mobile information gateway 100. For example, refinance, mortgages, student loans, insurance, investment services, other banking services, accounting services, tax services, legal services, travel and rental car services, accommodations, donations to charities are just a few ancillary services that may be recommended to banking customer. In some embodiments, the computing and communication module 104 and/or the backend server 108 determines a service preference of the first customer; determines a service capability of a plurality of tellers; selects one of the plurality of tellers that has a service capability similar to the service preference of the first customer; and then sends information for the customer to the human interface module of the selected one of the plurality of tellers for display (see also block 912 below). Other forms of teller matching as described below with reference to FIG. 10 may also be performed as part of the analysis 910. The analysis 910 of the customer based on an image captured by the human interface module 102 may be performed entirely on the human interface module 102, entirely on the backend service server 108, entirely on the computing and communications module 104 or cooperatively amount two or more them.

Next, the method 900 retrieves 912 customer data and information and sends it to the human interface module 102 for presentation. For example, account information about the customer may be retrieved and sent to the human interface module 102. In this manner, the teller is immediately presented with information that is related to the customer such as whether their account is overdrawn or whether an account has a high balance and another account or different type of account should be open. Depending on the bank's policies, a picture of the customer could also be retrieved and sent for presentation to the human interface module 102 so that the teller can be assured that they are interacting with the correct customer. The retrieval of customer data may be performed entirely on the backend service server 108, entirely on the computing and communications module 104 or cooperatively on both of them. The delivery of the data is performed by the computing and communications module 104. The data is received by the human interface module 102 and then presented using the image delivery and display mechanism 302. Examples of the presentation of information related to a particular customer by the human interface module 102 transparently overlaid upon a field of view are described in more detail below in FIGS. 15A-15E and 16A-16B.

Once the information is presented to the teller via the human interface module 102, the teller can interact with the customer in a normal fashion. The teller can use the human interface module 102 to input additional information such as requesting a transaction or an activity for the customer, requesting additional information, updating records, etc. The teller can input such requests via gestures, eye movement, voice commands, or other input mechanisms provided by the human interface module 102. The method determines 914 whether the teller has input any additional information or commands to the human interface module 102. If so, the information request is processed by the human interface module 102 and the method continues returns to step 910 to analyze and process the new information requests. If no additional commands are input are provided to the human interface module, the method is complete and ends.

FIG. 10 is a flowchart of one embodiment of a method 1000 for symmetrical use of the mobile information gateway 100 implementing a virtual queue. The symmetric case represents an entirely new set of activities and interactions that become possible with this unprecedented mode of engagement. In addition to the advantages described above for the symmetrical case and FIG. 9, each teller can dive into any service scenario with the customer, whether it is showing them how to fill out some form, or the benefits of some new service or investment (with 3D models of how your assets grow in each situation), or cross-selling of other products ("dream vacations from sister travel company"). In particular, the symmetric case allows the teller and customer to: have private communications, have communication in different languages using an automated translation engine, work collaboratively on the same data; and eliminate queues for services.

It should be understood that the method 1000 of FIG. 10 assumes that the teller wears a first human interface module 102a sometime before interaction with the customer wearing a second human interface module 102b. Further, it is assumed that the teller wearing the first human interface module 102a has also been identified or authenticated in a process similar to that described below used to identify and authenticate the customer. Each of the first human interface module 102a and the second human interface module 102b has an associated first computing and communications module 104a and a second computing and communications module 104b, respectively. The method 1000 begins with the customer entering a bank branch, picking up or being given the second human interface module 102b and wearing 1002 the second human interface module 102b. In some embodiments, the second human interface module 102b may adapt the display for prescription eye glass wearers. As noted above, in some embodiments, the second human interface module 102b includes a substrate 202 onto which the image delivery and display mechanism 302, projects information overlaid on the field of view. The second human interface module 102b captures and processes 1004 captured information or customer information. For example, the eye tracking camera 310 of the second human interface module 102b captures an image of the customer's face for facial recognition or an image of the customer's iris for iris recognition. The audio input device 314 of the second human interface module 102b may capture an audio clip of the customer speaking for use in voice recognition. Additionally, the camera 308 of the second human interface module 102b may capture an image of the item in the customer's hand (e.g., cash, check, debit card, etc.) for use in determining the purpose of the customer's visit. The other input devices of the second human interface module 102b may collect other information such as voice commands or information, user gestures, or selection of menus that are captured and processed. The method 1000 continues by verifying the identity and authenticating 1006 the customer. In some embodiments, the captured information is processed to determine an identity of the user. The captured information may also be used to authenticate the user. The identity and authentication of the customer can be performed using any of the methods described above. The identification of the customer, the authentication of the customer and the analysis of her needs may be performed entirely on the second human interface module 102b, entirely on the backend service server 108, entirely on the second computing and communications module 104b associated with the second human interface module 102b or cooperatively on two or more of them.

After the customer has been identified and authenticated in block 1006, the method 1000 continues with two different processes in parallel. For the customer, entertainment or information is sent from the backend service server 108 or the second computing and communications module 104b to the second human interface module 102b and displayed 1008 for the customer. This information can be any variety of entertainment in which the customer is interested, a variety of offers available to the customer, information about policy changes, or other information that may be of interest to the customer. Furthermore, the customer may use the second human interface module 102b to surf the Internet, place audio or video calls, or perform various other computing functions enabled by the mobile information gateway 100. In some embodiments, the customer may use the second human interface module 102b to perform any number of conventional banking transactions (e.g., balance inquiries, transfers, deposits, etc.) such as those currently available through an automated teller machine. For example, the camera can capture images of checks or other documents and then the images can be used to process the corresponding transaction such as depositing a check. Payments can be made to a mortgage or other transactions like credit card payments can be processed in a similar fashion. Various other ATM transactions, such as transferring funds, requesting checks, making payment or balance inquiries could also be performed in this manner. In other embodiments, other advanced functions may be performed by using the second human interface module 102b interacting and communicating with the backend service server 108 to provide a virtual teller functionality. In some embodiments, the second human interface module 102b can be updated so that when the customer looks at their preferred teller, the teller's information (name, picture wait time etc.,) can be overlaid on the display of the second human interface module 102b. Thus the mobile information gateway 100 is particularly advantageous because it changes the way in which customers are serviced and allows customers to be entertained, informed or productive while waiting to be serviced. It should be noted that the present invention is particularly advantageous because the customer need not move and can remain in a single location to receive his or her services. Moreover, the same space can be used by one customer for different purposes as different times, and even used by multiple customers at the same time. For example, a designated space may be used by the customer to be entertained while waiting as described above, as well as later interact with the teller. Additionally, that same designated space maybe used by multiple customers at the same time since the mobile information gateway device 130 will present the information of each user privately so it is not viewable other customers. Thus, a white wall or background could be used as the background field of view by a single user for entertainment, conducting a transaction, interacting with a virtual teller at different times during their visit at the bank branch. That same a white wall or background could also be used by two or more customer as the background field of view as they are entertained or conduct financial transactions.

Another example is if the customer is looking at some special bank display screens (e.g. table, wall displays or signatures) and is interacting with it, e.g. flipping through some announcements, performing some visual-search related activities. Those bank-specific activities can be logged at the server and can be provided to the teller so the teller knows the interaction history of the customer prior to the official banking interaction.

In parallel, with block 1008, the steps of blocks 1012 to 1022 are performed. While the steps of blocks 1012 to 1022 are described below as being performed by the backend service server 108, it should be understood that they could alternatively be performed by the first computing and communications module 104a, the second computing and communications module 104b, the backend service server 108, or a combination of the three devices. It should also be understood that in different embodiments, some steps of blocks 1012 to 1022 are optional.

The method 1000 sends 1012 customer information including the customer ID and the requested/task to the backend server 108. The backend service server 108 performs 1014 teller-customer matching, and a teller is assigned 1016 to service the customer. A particular teller may be assigned to the customer based on a variety of factors including fit of teller's professional skills to customer's needs, professional skill level, experience level, personality match, age, gender, language preferences, prior experiences (positive or negative), etc. In the simplest of embodiments, tellers may merely be assigned based on expected or actual availability. Next the method 1000 determines 1018 whether the assigned teller is available. The availability of the assigned teller may be determined by the backend service server 108 polling the current activities being performed by the human interface module 102 of the assigned teller. If the assigned teller is not available, the method 1000 returns and re-performs steps 1014 and 1016 to find another teller. On the other hand, if the assigned teller is available, the method 1000 continues to step 1020. In some embodiments, the method 1000 may perform additional steps such as identifying a list of alternate tellers, ranking the tellers in order of popularity to the customer and providing the information about the tellers to the second human interface module 102b with information such as names, pictures waiting times etc. The method 1000 then can offer the customer the option of waiting for the assigned teller or selecting a different teller from the list of alternates using the second human interface module 102b. In block 1020, an analysis of the customer and information is performed. The analysis can identify the customer, important information about the customer, preferences about the customer, the request/task the customer is there to perform, opportunities for selling additional services or products to the customer or any other information that will allow the teller to provide an enhanced experience. The customer data is then retrieved 1022 and sent to the first human interface module 102a of the teller and presented for use by the teller. For example, the customer may be identified in the field of view provided by the first human interface module 102a and arrows or other direction indicators guiding the teller to the customer may be presented on the first human interface module 102a. Similarly, the backend service server 108 may signal the second human interface module 102b of the customer to present arrows or other direction indicators to guide the customer towards the teller. Finally, the customer and the assigned teller interact 1010 to perform any type of transaction. The process for the customer and the assigned teller to interact is described in more detail below with reference to FIG. 11. Examples of the information presented on the respective human interface modules 102a, 102b and their corresponding transparent substrates 202a, 202b are also described below with reference to FIGS. 15A-16B. The positioning system 110 is used to determine the positions between the customer and teller and to provide signals on how to move through the physical space to meet face-to-face. The disclosed method 1000 is particularly advantageous in a number of respects. First, it eliminates the need for customers to wait in line for services. Second, there is no need for a customer to take a number for service because the process described is virtual and automatic, eliminating the need for the customer to make a request. Third, it allows the bank to use and the design the space in any number of ways to optimize customer service and efficiency. Finally, it eliminates lines so the bank can feel more like a destination that is desirable like certain stores.

Both parties, customer and teller, might want to go to a physical location, like a desk or counter, to type some text on a virtual keyboard. The positioning system assists on navigating to the physical location. Then the 3D camera captures the physical space, and the captured data enables accurate projection of a virtual keyboard on the display overlaying the physical space where the user is typing.

FIG. 11 is a flowchart of a method 1100 for symmetrical use of the mobile information gateway 100 for servicing a customer using plurality of human interface modules. Servicing of the customer begins when the teller completes 1102 an interaction with a customer. The customer is notified 1104 that the teller is available. For example, a message may be displayed on the second human interface module 102b used by the customer. The second human interface module 102b may also display 1106 directions to the assigned teller. In parallel, directions to the customer are displayed 1108 on the first human interface module 102a used by the teller. Customer data is also retrieved 1110, sent to the first human interface module 102a and presented to the teller. When the teller approaches the customer, the first human interface module 102a may display the customers information, her preferences, and services/products to recommend and why.

Once the teller and the customer meet, they begin an encrypted conversation. The conversation and information may be passed between the teller and the customer with the teller and customer using their respective human interface module 102a, 102b, respective computing and communications module 104a, 104b and the backend service server 108. The encrypted conversation may use a real-time voice changer/scrambler in the human interface modules 102a, 102b. In some embodiments, the respective computing and communications modules 104a, 104b compute a scrambling/changing signal, possibly based on the captured input voice and the human interface modules 102a, 102b output the scrambling/changing signal. This is particularly advantageous because it ensures that the conversation between the customer and the teller will be private. Furthermore, respective human interface modules 102a, 102b, respective computing and communications modules 104a, 104b and the backend service server 108 may provide language translation services so that both the teller and the customer may speak in the language which they are most comfortable. This also enables a teller who only speaks a single language, such as English, to service any number of clients that speak other languages. Both the teller and the customer can use their respective human interface module 102a, 102b to input commands 1114 or information, or select information for display. It should be understood that the information provided to the respective human interface modules 102a, 102b may be the same or different based upon the user. For example, a first set of data which includes the financial data of the customer may be displayed both on the human interface module 102a of the teller and the human interface module 102b of the customer. In another example, the first human interface module 102a may show a second set of data such as bank use only information that is not visible or presented on the second human interface module 102b of the customer. The method 1100 continues by presenting or displaying 1116 3D charts (e.g., displaying how savings would look like in a number of years, etc.), 3D models (e.g., displaying a new housing complex the bank is trying to sell) or data to both the first human interface modules 102a and the second human interface modules 102b. Other examples include 3D charts, pie charts and models of retirement accounts, expected performance, loan amortization, effect of extra payments beyond interest, mortgage calculations, credit card transactions and effects, etc. This is particularly advantageous because each user views the 3D charts from their own perspective. While the data is the same, each user's perspective on the 3-D charts is different depending on their location relative to the chart. Moreover, each user can interact 1118 with their respective human interface module 102a, 102b to manipulate the charts, see changes, input changes, etc. This provides a type of interaction heretofore not available in the banking context. It should be understood that in blocks 1114, 1116, 1118 any type of information may be presented to the teller and/or the customer such as special offers, notifications, limited promotions, recommendations, etc. The method 1100 completes with the teller performing 1120 a transaction using the first human interface module 102a, and the encrypted conversation and joint display ending 1122.

In some embodiments, the human interface module 102a, 102b could also display "shared screens," where one part is the common display that both parties see, and another one is a "private" part. That way the user can look up special account information while looking at the common charts. The teller can also have a shared and a private display area.

FIGS. 15A-15E are graphic representations of a field of view of an area through a substrate 202 of the human interface module 102 with information overlaid upon the substrate 202.

Figure 15A:
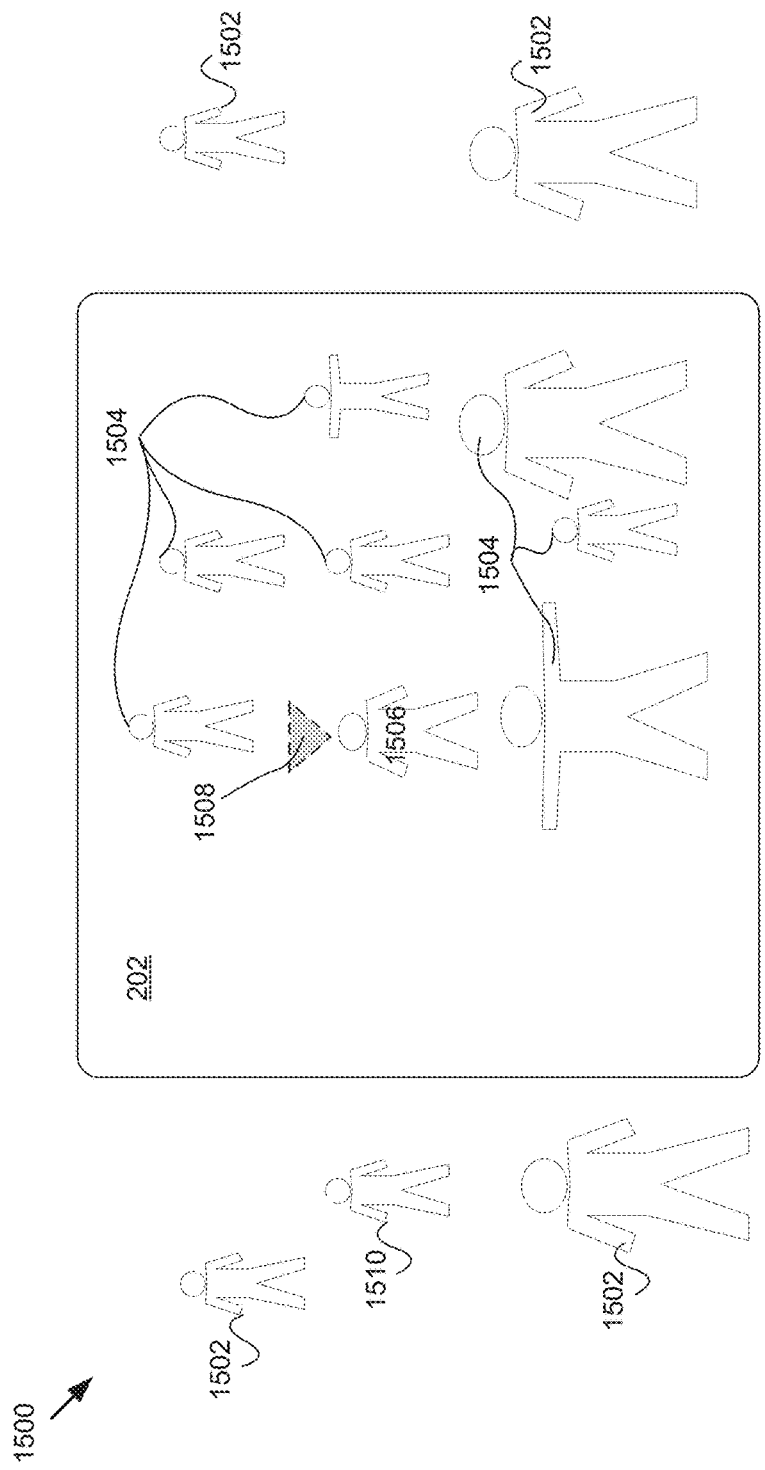

Referring now to FIG. 15A, a graphical representation of a service area 1500, for example a bank lobby or a waiting area for a hospital or doctor's office, is shown. In the bank lobby or waiting areas, there are a plurality of customers or patients 1502, 1504, 1506 and 1510. Throughout the description above and that follows the terms customers and patients are used interchangeably to mean the person receiving services. Similarly, throughout the description above and that follows the terms teller and medical personnel (doctor, physician, or other similar terms) are used interchangeably to mean the person providing services. The field of view is defined by the substrate 202 through which the user of the human interface module 102 views portions of the area 1500. As shown, some of the customers or patients 1502, 1510 are outside of that field of view while others 1504, 2006 are within the field of view. For convenience and ease of understanding, only a single substrate 202 is shown in FIG. 15A; however, it will be recognized that using the embodiment of the human interface module 102 of FIG. 2, there would be a pair of substrates 202 for binocular viewing. In such embodiments, different or the same information may be presented on the different substrates 202.

FIG. 15A illustrates an example where the field of view provided by the substrate 202 includes an image of a portion of the service area 1500 having a plurality of customers or patients 1504, 1506. The human interface module 102, in particular the image delivery and display mechanism 302, projects a call out 1508 onto the substrate 202. FIG. 15A illustrates this projected information about an identified customer 1506 with dashed lines to indicate that is not part of the background scene that includes the customers 1504, 1506. It should be understood that while the call out 1508 is a triangle above the head of the identified customer 1506, the call out 1508 could take any number of other forms with different shapes, colors, sizes, and positions. For example, the call out 1508 in other embodiments could be a square around the identified customer 1506. The present invention advantageously performs the steps of the method described above with reference to FIG. 9, and then once a customer has been identified, projects the call out 1508 to indicate which customer the teller or medical personnel wearing the human interface module 102 should approach and with which begin to interact.

Figure 15B:
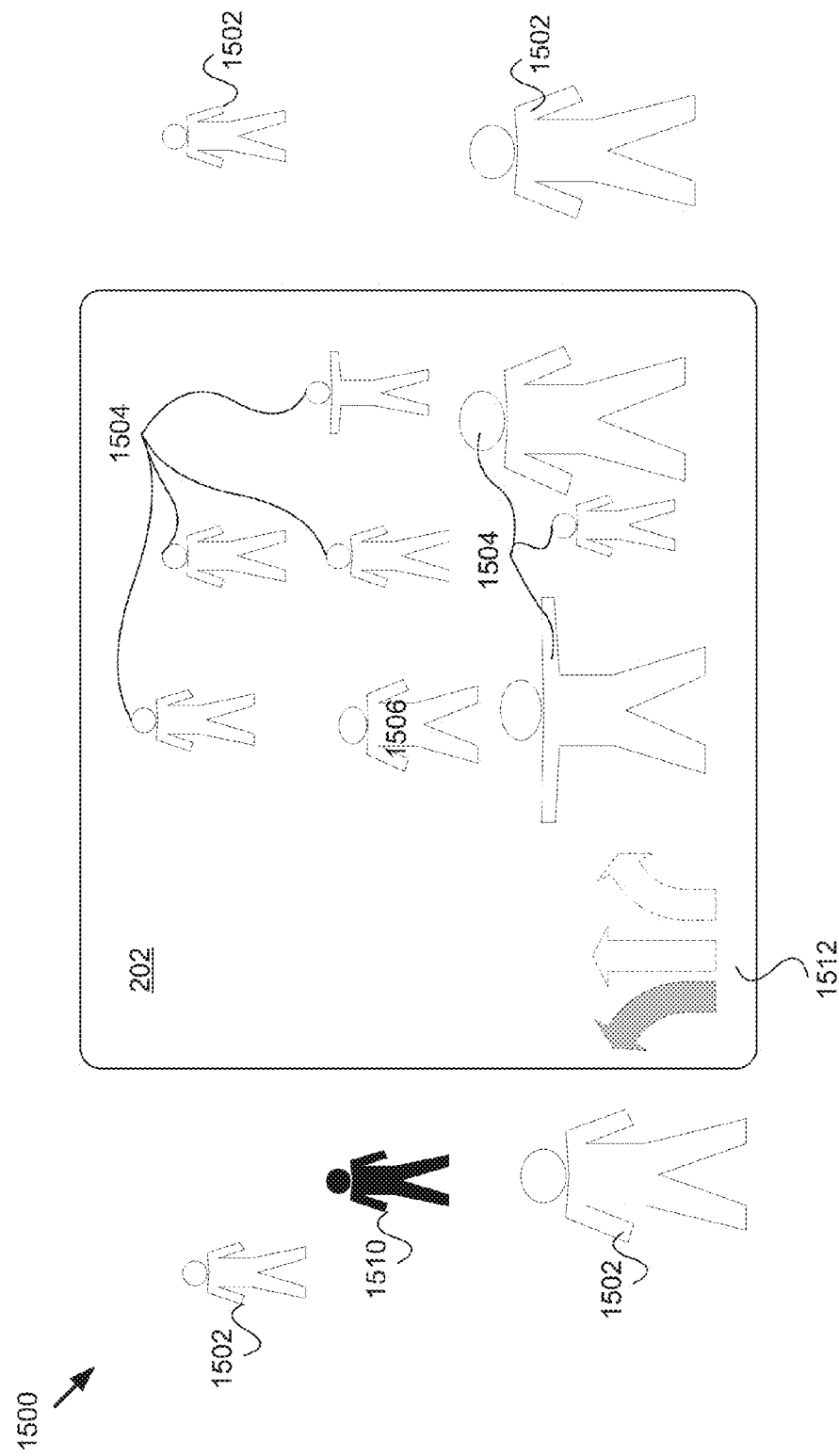

FIG. 15B illustrates an example where the human interface module 102 has been used to capture images of the service area 1500 and provides a directional indicator 1512 to travel to meet the customer 1510. The process described above with reference to FIG. 9 has been performed and has identified a particular customer 1510 with which the teller or medical personnel wearing the human interface module 102 needs to service. In this example, a directional indicator 1512 is projected onto the transparent substrate by the image delivery and display mechanism 302. For example, the directional indicator 1512 can be a symbol such as an arrow indicating which direction that the wearer of the human interface module needs to travel to meet the customer 1510. The directional indicator 1512 could be a series of arrows as shown with one of the arrows highlighted. In other embodiments, only a single arrow indicating which direction the user should move can be provided. It should be understood that the directional indicator could have a variety of other formats, positions, and colors other than that shown in FIG. 15B. For example, the directional indicator 1512 may be simply an arrow on the left side, top side or right side of the substrate 202.

FIG. 15C illustrates an example where the human interface module 102 has been used to capture images of the service area 1500 and provides a location 1514 or 1516 of the customer or patient 1506. In this example, an area 1514 is provided in which the image delivery and display mechanism search 302 can display the location of the customer 1506. For example, the location information can merely be a description such as "Patient is in the center of the lobby" that is displayed in area 1514. In addition to or in the alternative, the location information may be highlighting 1516 such as a border about the identified customer. This is particularly advantageous because it allows the teller to quickly and easily identify the customer 1506 with which they are supposed to meet and interact. It should be understood that in other embodiments, the area 1514 may also be used to present other information including but not limited to a service or offer to recommend to the customer 1506, or an identification that a particular teller should or should not attempt to interact with the customer 1506. The highlighting 1516 also could be replaced by an image or other information but nothing the less illustrates how the information is displayed transparently overlaid upon the field of view of the first customer sized relatively similar to the field of view and positioned proximate the first customer in the field of view.

Figure 15D:
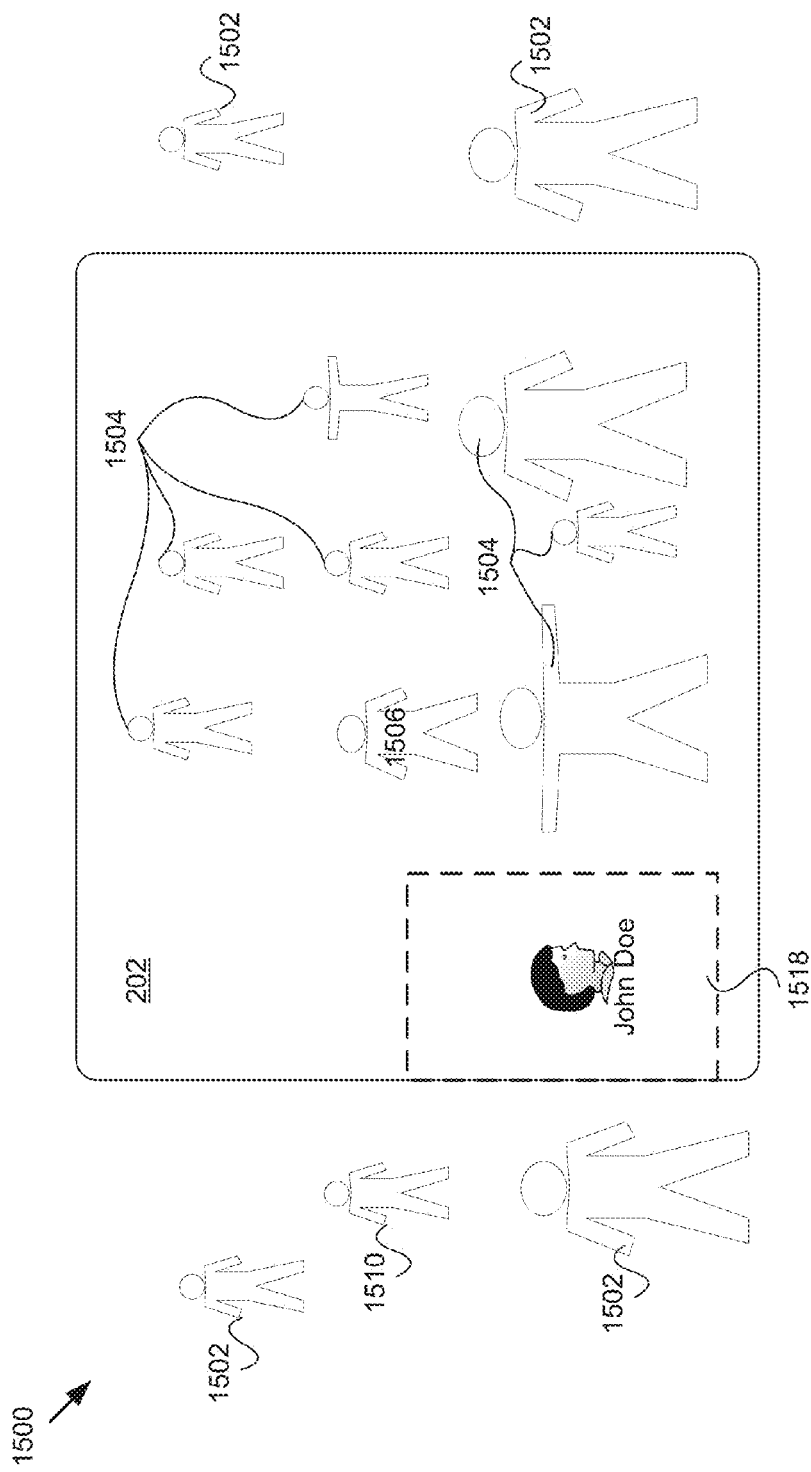

FIG. 15D illustrates an example where the human interface module 102 has been used to capture images of the service area 1500 and the area 1514 provides an image 1518 of the customer 1506. This is advantageous because it allows the teller to double check and easily recognize the customer which they are supposed to be servicing.

FIG. 15E illustrates an example where the human interface module 102 has been used to capture images of the service area 1500 and a plurality of customers have been identified. Each of the identified customers has an associated call out 1508, 1520. FIG. 15E is used to illustrate that the system of the present invention may be used to identify any number of customers. Further, while only two customers are identified, all the customers viewable within the field of view provided by the substrate 202 could also be identified. Furthermore, the system might assign priorities in which customers should be serviced in such an embodiment where all the customers are identified. Those identifications and priorities could be projected onto the substrate 202 for use by the teller in a similar manner to the call outs 1508 and 1520 shown.

Figure 16A:
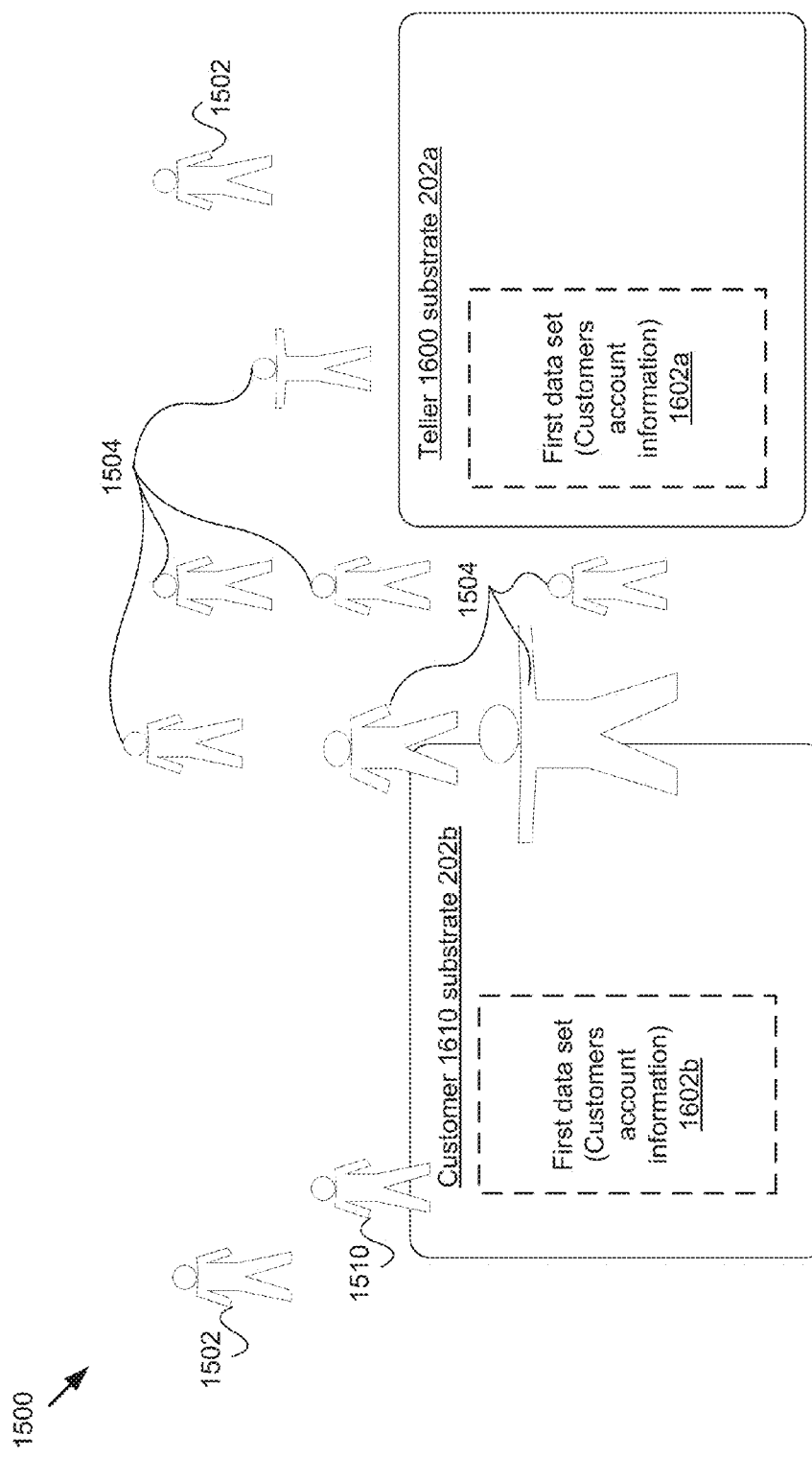
FIGS. 16A-16B are graphic representations of a field of view of an area through a first substrate of a first human interface module and a second substrate of a second human interface module with information overlaid upon each substrate.
Figure 16B:
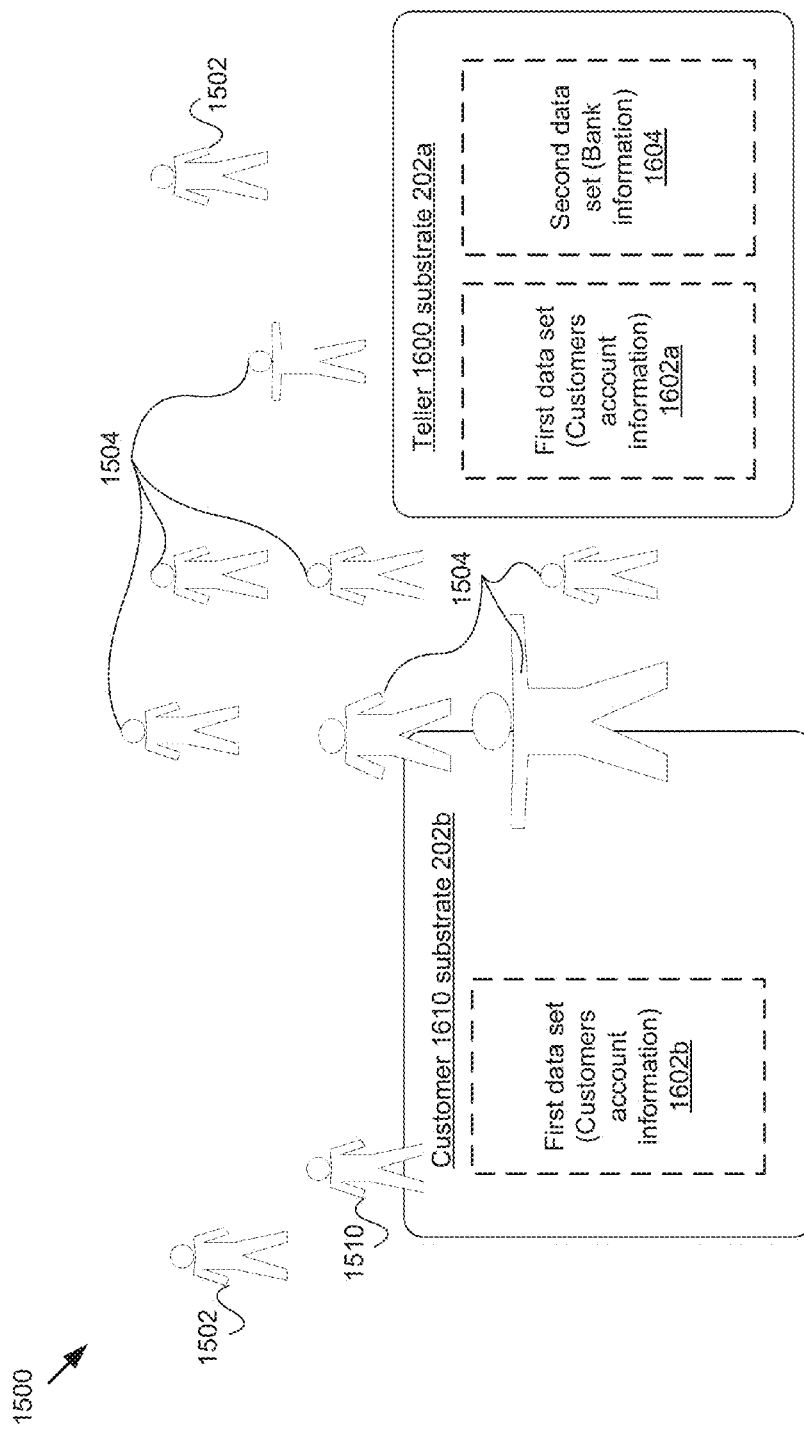

FIGS. 16A and 16B are graphic representations of a field of view of a service area 1500 through a first substrate 202a of a first human interface module 102a for a teller or medical personnel 1600 and a second substrate 202b of a second human interface module 102b for a customer or patient 1610 with information transparently overlaid upon each substrate 202a, 202b. As illustrated by FIG. 16A, both users (the teller 1600 and the customer 1610) use their corresponding human interface module 102A, 102B to view a service area 1500 such as the lobby of a bank, or a patient waiting area. The patient waiting area may include any number of other customers 1502, 1504 and 1510. Each of their respective human interface modules 102a, 102b includes a substrate 202a, 202b. For example, both the teller 1600 and the customer 1610 wearing a pair of mobile information gateway glasses, and the lenses of the glasses provide the substrates 202a, 202b. Each of the human interface modules 102a, 102b is able to display a first set of data 1602a, 1602b upon their respective substrates 202a, 202b as depicted in FIG. 16A. This is advantageous in a number of respects. First, as with the other use cases described above with reference to FIG. 15, the information is advantageously overlaid upon the field of view provided by the substrate 202a, 202b so that the user 1600, 1610 may see both the other customers 1502, 1504 and 1510 as well as the information presented on the substrate 202a, 202b. Second, the information presented to each user 1600, 1610 is private in that only the teller or medical personnel 1600 using the first substrate 202a is able to view the first data set 1602a. Similarly, only the customer or patient 1610 using the second substrate 202b is able to view the first data set 1602b. In this example, the first data set is the same for the customer or patient 1610 and the teller or medical personnel 1600 and represents the customer's account information. While each user 1600, 1610 is only able to view the data presented on his or her respective substrate 202a, 202b, the same data can be sent to both substrates 202a, 202b, thereby allowing both individuals to interact with the same data or share the same data. It should be noted that this information is visible only to the customer 1610 and the teller 1600. The other customers 1202, 1204 and 1210 are unable to view either substrate 202a, 202b, and thus have no access to the information being presented.

Referring now to FIG. 16B, another example of information presented on the first substrate 202a to the teller or medical personnel 1600 and the information presented on the second substrate 202b to the customer or patient 1610 are shown. This example illustrates projection or display onto the first substrate 202a of a second data set 1604 such as bank information or medical information or records. The bank information could be confidential bank information used by tellers when interacting with customers, for example the customer's credit history, loan status, credit card status, etc., or specific test results and procedures used by a doctor. The bank information could also be offers or promotions specifically for this customer 1610. The medical information could be lab test results or other more technical medical information useful for physician. The medical information could also be offers or promotions specifically for this customer such a coupon for trial pharmaceuticals, medical devices, tests, etc. As illustrated in FIG. 16B, the second data set 1604 is only projected on the first substrate 202 and therefore is only visible by the teller or doctor 1600, and not the customer 1610 or the other customers 1502, 1504 and 1510. It should also be noted that the second data set 1604 is displayed on the first substrate 202a in addition to the first data set 1602a.

Methods for Using Mobile Information Gateway in Healthcare and Medicine

Referring now to FIGS. 9, 12, 13 and 17 the mobile information gateway 100 will be described in the context of healthcare and medicine. In one embodiment, the doctor or other medical professional is in the same room as a patient in a medical facility having face-to-face interaction. This is similar to the in-branch use of the mobile information gateway 100 described above for the financial services context. In another embodiment, the mobile information gateway device 130 is used in a portable scenario outside of a medical facility. For example, the mobile information gateway device 130 may be packaged as part of medical equipment such as a defibrillator installed in offices or public locations. In yet another embodiment, the mobile information gateway 100 is used in operating rooms either with the patient and doctor being in the same room, or during remote surgery or medical consultation. In the latter two scenarios the patient might be non-responsive (e.g., being under anesthesia). The mobile information gateway device 130 can be used to provide additional information about the patient or procedure to the doctor, or for capturing the procedure and transmitting it to other people for teaching purposes While the healthcare and medical applications of the mobile information gateway 100 are generally described below with a doctor using the mobile information gateway device 130, it should be understood that the mobile information gateway device 130 can also be used by any medical professional, medical staff, home care giver or other person in the medical facility or working remotely.

The application of the mobile information gateway 100 to the health care or medical context will now be described. More specifically, the mobile information gateway 100 will be described as being used in a reception area where the patient and doctor are present together in one location, for example, to provide triage, an immediate medical evaluation or discussion. The method and steps performed by the mobile information gateway 100 are similar to those described above with reference to FIG. 9. In a similar manner, a medical staff or professional in the reception area for medical facility can use the mobile information gateway 100 to perform patient identification and authentication. For example, the medical staff may be wearing a mobile information gateway device 130. The human interface module 102 of the medical staff member captures an image of the patient or her eyes and either performs facial recognition or iris recognition. This can be done by sending the captured image to computing and communication module 104 for further processing and delivery to the server 108. The recognized person or information about them can then be sent back to the human interface module 102 from the backend service server 108. It should be understood that in some embodiments the identification, verification and retrieval of information about the patient may be distributed across the human interface module 102, the computing and communication module 104 and backend service server 108 in a variety of proportions. Once the information about the patient has been retrieved and provided to the human interface module 102, it can be displayed privately on the human interface module 102 to the medical staff member. In another embodiment, a person entering the medical facility is asked to wear a mobile information gateway device 130.

The operations for identification, authentication and presentation of the patient information are the same as described above, except that the steps are performed by the mobile information gateway device 130 worn by the patient. There are a number of other uses of the mobile information gateway device 130 by the patient that are described in more detail below. Either of these configurations is advantageous because either the patient or a receptionist wearing the mobile information gateway device 130 can check the patient in, and perform other administrative functions thereby allowing initial intake of patients to be done more efficiently. Furthermore, once the patient has been identified, information about that patient's medical history, recent conditions, and any other helpful information can be provided to medical personnel utilizing a mobile information gateway device 130. The mobile information gateway device 130 can also be used to retrieve any additional information about the patient. For example, a type of "ER dashboard" can be presented on the image delivery and display mechanism 302 of the human interface module 102. The ER dashboard may display information including but not limited to: vital signs, allergies to medications, alerts, reminders, any information that requires memorization like lifesaving CPR instructions, basic first aid, etc. It should be understood that a receptionist or greeter in any context wearing the mobile information gateway device 130 can provide better and customized service to persons entering any type of business by performing the identification, authentication and information retrieval specific to the person as has been described above. For example, a receptionist at a high-end restaurant, a high-end hotel, spas, and other service industries could use the mobile information gateway device 130 to identify returning customers and provide information so that the returning customers have an improved experience.

It is important to note that the entire MOBILE (in the field) health care experience can be significantly enhanced with the mobile information gateway system 100 because (a) the health care provider (nurse, technician, doctor, care giver, etc.) can identify the patient immediately (if she has a prior record) and immediately access all her information while the health care provider is treating her thus saving time (and cost) and enhancing the treatment of her current ailment. This applies to any form of health care provided in the field (outside a clinic); and (b) any form of medical equipment that has been sub-optimal to use in portable or mobile form because of smaller display size can now be used with same level of efficacy as in the clinic. One example of this is the portable ultrasound where in current systems the image is displayed on a small mobile display screen that is much smaller than the larger display available at the clinic. A much lower cost and higher capability configuration could be enabled by having the ultrasound probe connect directly to mobile information gateway device 130 (or indirectly through an adapter if the ultrasound probe uses proprietary hardware interface that needs to be transformed to standard interface (like USB, HDMI, Wi-Fi, etc.). All this is enabled by the health care provider using the image delivery and display mechanism 302 of the mobile information gateway device 130 to view images and the image delivery and display mechanism 302 providing a wide-field-of-view, whereas current systems do not have such capability.

The health care interaction (anywhere—in hospital/clinic or mobile) between any type of health care provider (starting with the receptionist or first person who interacts with new patient) and a patient is enhanced by the use of the mobile information gateway system 100 because it enables the health care provider to spend most of their time looking at the patient, even while accessing information as needed. It is well known that making patients feel comfortable is an important part of healing them and making direct eye contact with them instead of looking away a lot of the time to look at various screens helps significantly in this regard. This is enabled by the image delivery and display mechanism 302 of the human interface module 102 providing a wide-field-of-view that can be overlaid on the real world view of the patient and interacting with body parts of the patient, whereas current medical display systems do not provide such a capability.

In some embodiments, the mobile information gateway device 130 is used in other contexts such as the emergency room or for admittance to emergency. In addition to performing identification, authentication and provision of information, the mobile information gateway device 130 can be used to capture additional information about the patient and send that information to the backend service server 108 for processing. For example, the mobile information gateway device 130 may be used as a tool to assist in immediate triage and assess the patient's physical condition. In some embodiments, the human interface module 102 may also include inputs to receive signals from various medical tools and devices so that the mobile information gateway device 130 captures other information such as vital signs, infrared images, ultrasonic images etc. Once the information has been processed, it can be sent back to the mobile information gateway device 130 so that it can be used in diagnosis. In some embodiments, multiple mobile information gateway devices 130 can be used so that an intake person or receptionist can pull up information about the patient very quickly such as the medical history and whether they have insurance. That first mobile information gateway device 130 can be communicatively coupled to a second mobile information gateway device 130 used by a physician or nurse to triage and diagnose the patient's condition. Once the patient's identity has been established and authentication has been performed, relevant information can then be sent to the second mobile information gateway device 130. The second mobile information gateway device 130 can then use the information specific to the patient they are about to see. This would allow the physician or nurse to have a combination of digital and real world information and thereby improve the accuracy and speed at which the patient's condition can be established and treatment can begin.

Figure 12:
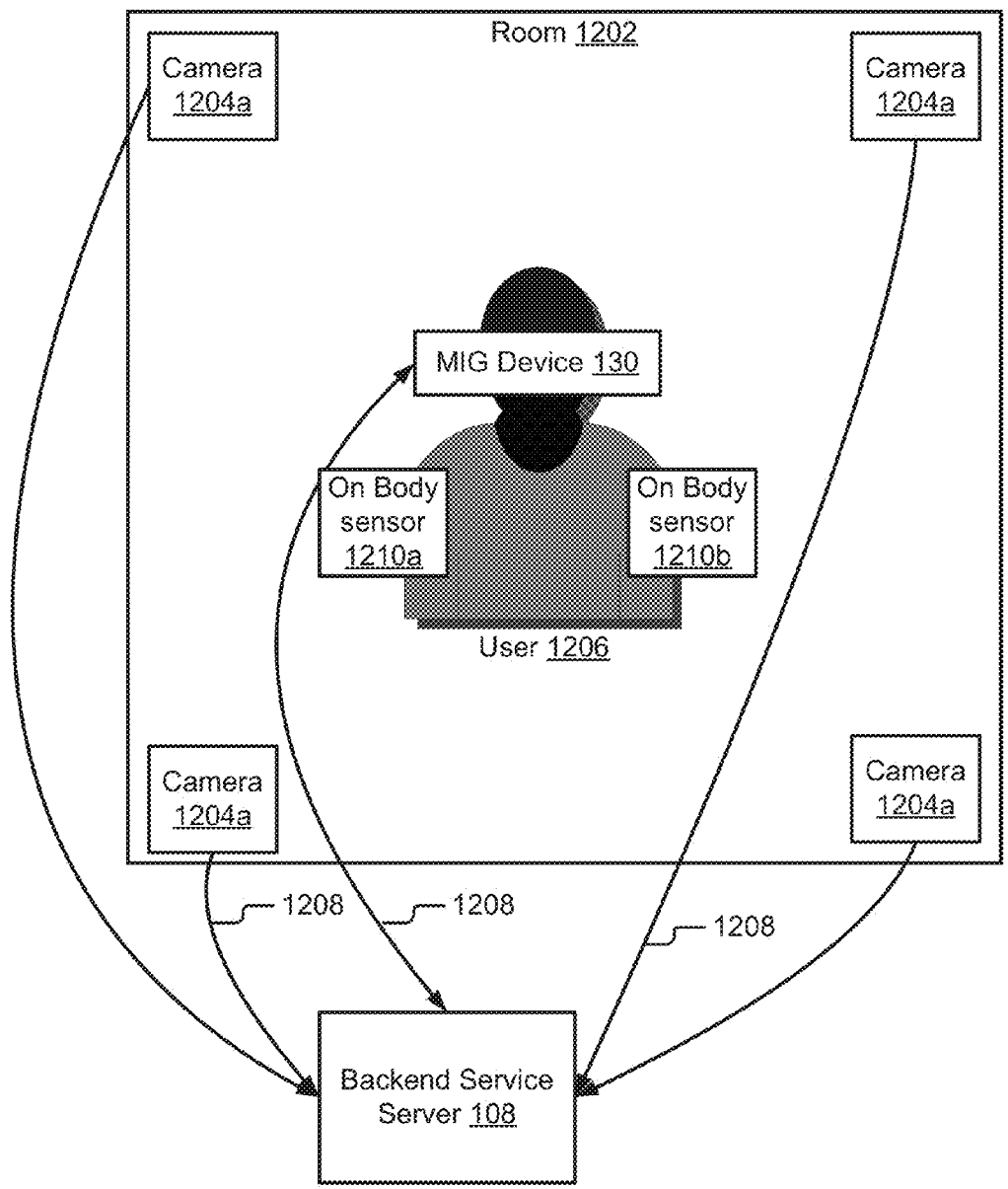
FIG. 12 is a block diagram of one embodiment of an intelligent room for use in conjunction with the mobile information gateway system.

Referring now to FIG. 12, one embodiment of an intelligent room 1202 for use in conjunction with the mobile information gateway system 100 is shown. The intelligent room 1202 has one or more sensors 1204a, 1204b, 1204c, and 1204d to capture information about a user 1206. In this example, the one or more sensors 1204a, 1204b, 1204c, and 1204d are cameras to capture the movement of the user 1206. The patient may also be wearing one or more on body sensors 1210a, 1210b. While this example shows four cameras, other embodiments could include as few as a single camera or many more than four cameras. Furthermore, while the intelligent room 1202 will be described in the context of cameras, the sensors 1204a, 1204b, 1204c, and 1204d could also be IR cameras, heat sensors, motion sensors, position sensors, pressure/force sensors, heart rate monitors, 3D sensors, etc. or any combination thereof. Moreover, the sensors 1204a, 1204b, 1204c, and 1204d could be any medical equipment or patient monitoring equipment (not shown) that generates and provides information about the status of the patient. For example, the patient monitoring device may monitor any one of blood pressure, blood flow, blood glucose, heart rate, temperature, electrocardiography, pulse oximetry, capnography, respiratory rate, intracranial pressure, etc. The sensors 1204a, 1204b, 1204c, and 1204d are used to capture the movement and motion of the user 1206. The sensors 1204a, 1204b, 1204c, and 1204d may also be used to monitor patient condition such as during surgery or other procedure. In one embodiment, each of the sensors 1204a, 1204b, 1204c and 1204d is coupled to provide the capture images or other information to the backend service server 108 as depicted by lines 1208. The sensors 1204a, 1204b, 1204c, and 1204d advantageously provide greater information about activity inside the intelligent room 1202. For example, the sensors 1204a, 1204b, 1204c, and 1204d can capture the patient in physical therapy such that his/her pose can be digitally analyzed. The patient is wearing the mobile information gateway device 130 which provides additional information about movements, positions, workout statistics, etc. which are transmitted to the backend service server 108 as depicted by line 1210. Continuing with the example physical therapy, the user 1206 may be required to perform certain exercises as part of their physical therapy regime. Patients often perform these exercises improperly and thereby do not receive the full rehabilitative value of the exercises. The additional information provided by the sensors 1204a, 1204b, 1204c, and 1204d in the intelligent room 1202 may be processed along with the information from the mobile information gateway device 130 to measure and record performance information and sent back to the patient so that it can be viewed on the mobile information gateway device 130. For example, images of how the patient is performing physical therapy exercises may be overlaid on top of images of the ideal way to perform the same physical therapy exercises (ideal behavior). This blended image can then be presented to the user on the mobile information gateway device 130 so that he/she has immediate feedback about the way in which he/she is performing the physical therapy exercises. Additionally, a corrective instruction based on the comparison of the performance information to the ideal behavior may be sent to and presented by the human interface module 102. In this manner, the feedback and information is immediate and the user 1206 can modify the way in which they are performing the physical therapy exercises so that they match the idea. Similarly, a waiting room, patient examination room, or an operation room (OR) maybe equipped with sensors 1204a, 1204b, 1204c and 1204d, on body sensors 1210a, 1210b or patient monitoring devices (not shown) as has been described above. The sensors 1204a, 1204b, 1204c and 1204d and on body sensors 1210a, 1210b may be coupled to provide the information to the backend service server 108 or communication may be established with the mobile information gateway device 130 directly. In either case, signals indicating the condition of the patient are generated by the sensors 1204a, 1204b, 1204c, and 1204d on body sensors 1210a, 1210b and sent directly or via the backend service server 108 to the mobile information gateway device 130. The mobile information gateway device 130 receives these signals and present the information on its human interface module 102.

Figure 14:
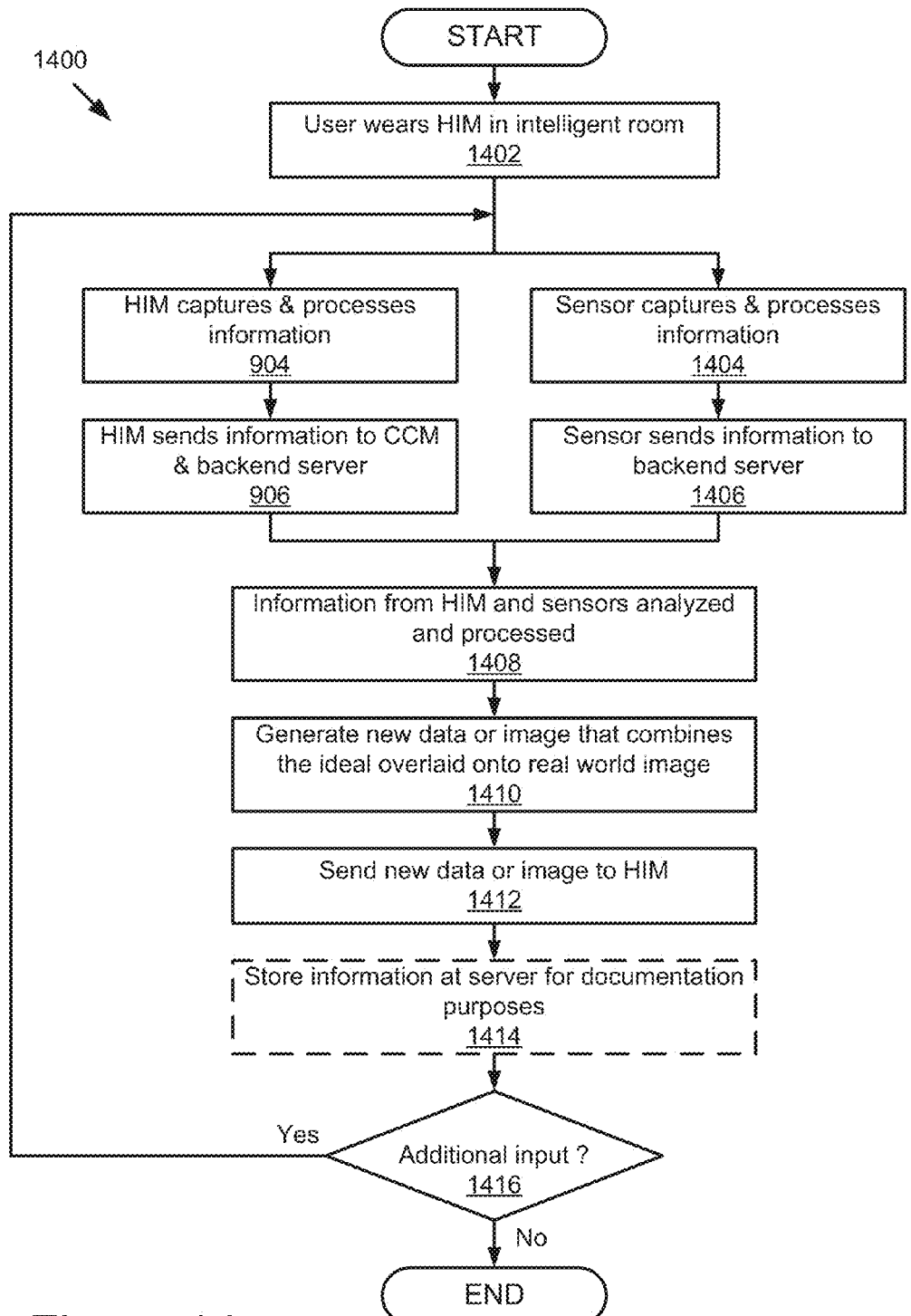
FIG. 14 is a flowchart of one embodiment of a method for providing real-time feedback using the intelligent room.

Referring now to FIG. 14, a method 1400 for providing real-time feedback using the intelligent room 1202 and the mobile information gateway system 100 will be described. The method 1400 begins with the user wearing the human interface module 102 in the intelligent room 1202. This allows the mobile information gateway device 130 to capture a variety of different types of information about the user and her movement or condition. It also allows the sensors 1204, whatever type they may be, to also capture information about the user and her movement or condition. Next, the human interface module 102 captures 904 and process information, and sends 904 the information to the communication and computing module 104 and the backend services server 108, as has been described above with reference to FIG. 9. The sensors 1204 of the intelligent room 1202 also capture 1404 and process information, and send 1406 that information to the backend services server 108. It should be understood that in some embodiments the sensors 1204 may capture information with the same absolute clock used by the human interface module 102 so that the information they both capture can be synchronized. In some embodiments, the sensors 1204 include some amount of processing capability and pre-process the information before to sending to the backend services server 108. The backend services server 108 receives the information from the human interface module 102 and the sensors 1204, then processes 1408 and analyzes the information. The method 1400 continues by generating 1410 new data or a new image. For example the new data could be raw data or a comparison of past data to current or new data. The new image may combines an ideal image (such as a preferred position for performing a physical therapy exercise) overlaid onto a real world image (such as an image of the user captured by the sensors 1204 performing the physical therapy exercise). In order to generate the image in block 1410, the information captured by the human interface module 102, for example, position information, audio information, image information etc. may be processed in addition to the information received by the sensors 1204. This processing necessary to generate the image in block 1410 is performed in block 1408. In one example, overlay applications, like in ultrasound or dermatology, require taking imagery of the object with the mobile information gateway device 130 to get positioning information (perhaps through 3D camera or depth ranging sensing technology), then additional information (images from previous visits or different image modalities, such as ultrasound) are overlaid onto the real world object. The newly generated data or image is then sent 1412 to the human interface module 102 for display to the user. Optionally, the image sent to the human interface module 102 may also be stored 1414 at the backend services server 108 for documentation purposes. The method 1400 then continues to determine 1416 whether additional input is being sent by the human interface module 102 and the sensors 1402. If so, the method 400 returns to blocks 904 and 1404 to repeat the process. In such a manner, the mobile information gateway system 100 may provide real-time feedback to the user or to the medical professional to significantly enhance performance of tasks or presentation of information about a medical condition. If no additional input is received in block 1416, the method is complete and ends.

In another embodiment, the mobile information gateway device 130 is used in a portable scenario outside of a medical facility. In certain cases, the mobile information gateway device 130 has a more general purpose use and may be used to augment the use of numerous types is special equipment. In such a case, the mobile information gateway device 130 is used to capture information, to process the information captured to determine whether a second specialty device is present, to analyze the information captured to identify a type of the second device, to retrieve instructional information corresponding to the type of the second device and to present the instructional information on the mobile information gateway device 130 so that the user can operate the specialty equipment with little or no experience. In this example, the mobile information gateway device 130 may be used to provide instruction on how to use several different types of special devices. For example, the mobile information gateway device 130 may be part of a first aid kit and provide instruction on how to use all the supplies and equipment in such a first aid kit. In other cases, the mobile information gateway device 130 is prepared for use with a specific medical device or emergency device. In these cases, the mobile information gateway device 130 may be largely self-contained and include the instructional information necessary to operate the specific medical or emergency device. For example, the mobile information gateway device 130 may be packaged as part of medical equipment such as a defibrillator installed in offices or public locations. The mobile information gateway device 130 may be packaged inside the glass container that also houses the defibrillator. As the user begins to use the medical equipment, they also wear the mobile information gateway device 130. The mobile information gateway device 130 stores instructions that can be interactive so that as the user is operating the medical equipment, the mobile information gateway device 130 can present step-by-step instructions on how to use the medical equipment or other emergency equipment. Since the mobile information gateway device 130 is capturing an image of the scene as well as other information, if the user forgets to perform a step or is performing a step improperly, the mobile information gateway device 130 can present warning messages or present the proper procedure as well as audio signals to capture the attention of the user. More specifically, the mobile information gateway device 130 advantageously presents the instructional information overlaid on the field of view that includes the medical or emergency equipment. In addition to providing feedback to the user via presentation, the mobile information gateway device 130 can capture additional information about use of the medical equipment such as by capturing images of the current scene that includes the medical device. The mobile information gateway device 130 processes the additional information to detect incorrect use of the metal call equipment and if incorrect use of the medical equipment is detected, the mobile information gateway device 130 presents corrective instructions. The mobile information gateway device 130 may communicate and cooperate with the backend service server 108 to process the additional information, detect incorrect use and provide corrective instruction. In some cases, mere use of the mobile information gateway device 130 that has been packaged with emergency equipment, may initiate the mobile information gateway device 130 to capture additional information, to process the additional information, to notify an emergency dispatcher that the mobile information gateway device 130 has been used and to provide the captured and process information. In some embodiments, the computing and communication module 104 of the mobile information gateway device 130 communicates with the medical equipment so that information provided by the medical equipment is displayed by the mobile information gateway device 130. This use of the mobile information gateway device 130 is particularly advantageous for situations where the medical equipment is likely to be used by people with little or no training on that medical equipment. In a similar manner, the mobile information gateway device 130 could be used to provide first aid instructions or CPR instructions to the untrained user in emergency situations. There are various other emergency situations in which the mobile information gateway device 130 can be valuable. For example passengers sitting in emergency exit rows on airplanes could be required to wear the mobile information gateway device 130 during the flight. If an emergency circumstance were to occur, the mobile information gateway device 130 could communicate with a server on the airplane for updates as to the status of the situation, to receive and present instructions on how to perform emergency procedures, to receive and present information from the flight crew, to access and operate emergency equipment, etc. This use case is applicable to various different transportation vehicles where the instructional information provided by the mobile information gateway device 130 includes step-by-step instructions for operating safety equipment built into the transportation vehicle. For example, a mobile information gateway device 130 could be included in a lifeboat on a ship, emergency equipment for a passenger bus, emergency procedures for a train, etc.

One particular advantage of using the mobile information gateway device 130 in the medical and healthcare environment is the ability to provide instant documentation. For example, all the information captured by the human interface module 102 of the mobile information gateway device 130 can be transferred and stored on the backend service server 108. Furthermore, the information that is stored can also be time coded or stored with an absolute reference clock. In some embodiments, the capture of information and the presentation of information by the mobile information gateway device 130 are synchronized with an absolute clock that may be on the backend services server 108 or the computing and communication module 104. The absolute clock, the captured information and the presented information, then later be used to replay of the entire session or interaction with the patient. In other words, a precise time line of everything can be on that clock absolute clock, for re-assembly later on a screen, or played back to you on the mobile information gateway glasses. This is particularly advantageous for storing records of how surgical procedures were performed, audio notes, and a complete record of the patient encounter. Once this information has been stored on the backend service server 108, it can be reviewed and processed for a variety of additional uses such as training, archiving, quality enhancement, and legal purposes.

Figure 13:
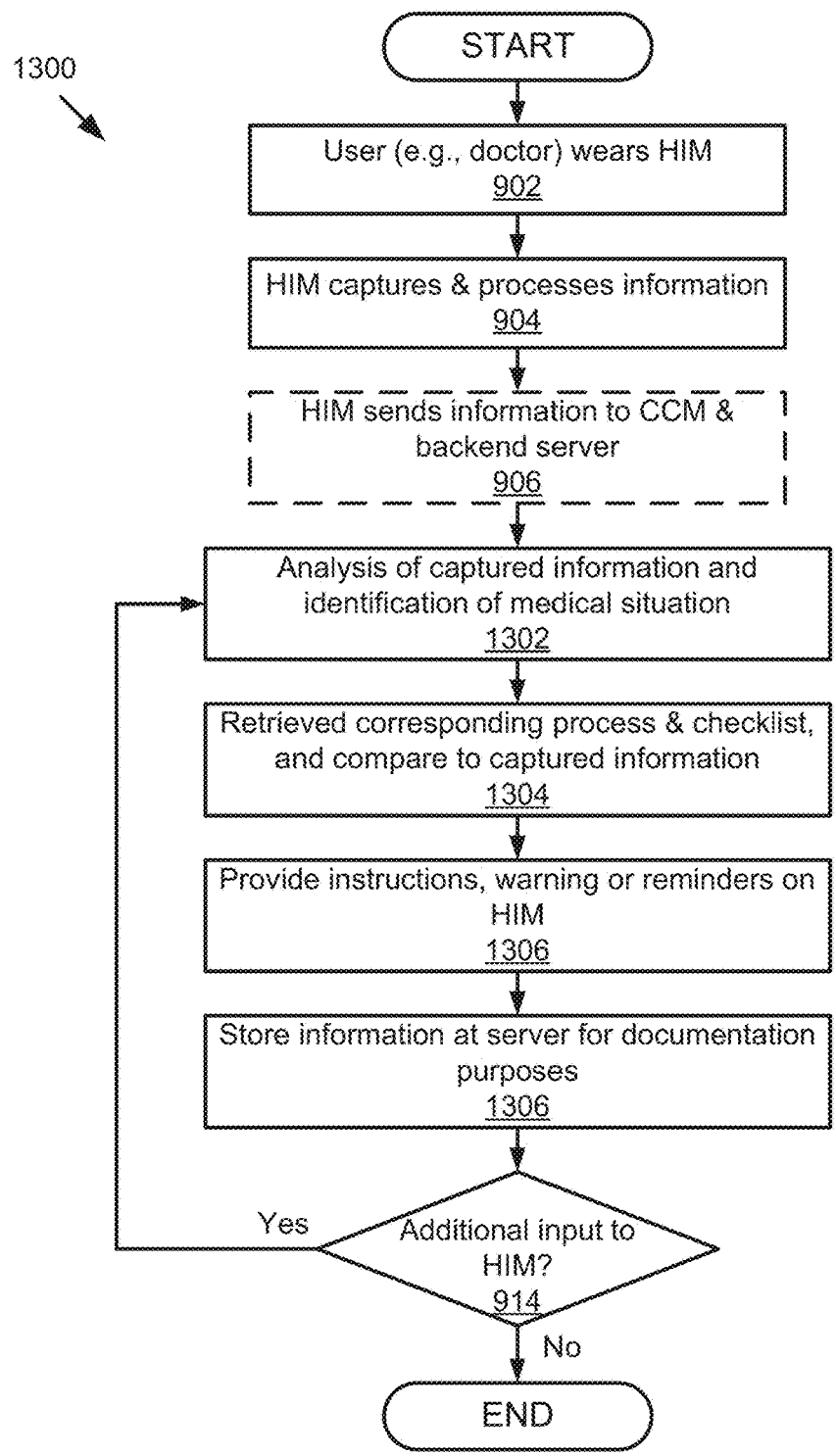
FIG. 13 is a flowchart of one embodiment of a method for using the mobile information gateway system in a medical or healthcare context.

Referring now to FIG. 13, a method 1300 for using the mobile information gateway system 100 in a medical or healthcare context will be described. The method begins with the same first three steps as has been described above with reference to FIG. 9. It should be understood that the captured information is processed to determine an identity of a first user, for example medical personnel, and authenticate the first user. The same captured information or additional captured information can be used to determine the identity and authenticate the patient. The identification and authentication can be done using facial recognition or iris recognition. In the simplest example, the identity of the medical personnel and the identity of the patient are used to retrieve information about the patient. That information is then presented using the mobile information gateway device 130 overlaid on a field of view of the medical personnel. Next the method 1300 continues by analyzing 1302 the captured information and identifying 1302 the medical situation. Based on the information captured by the human interface module 102, the backend services server 108 processes that information to identify the medical situation. In other embodiments, the processing could be done by a component of the mobile information gateway system 100 other than the backend services server 108. The corresponding process or check list suitable for the medical situation is then retrieved 1304 and compared to the captured information. In most embodiments, this will be performed by the backend services server 108, but it could be performed by the medical information gateway device 130. For example, the patient may be at a doctor's office merely for a standard annual physical. In such a case, the information presented on the mobile information gateway device 130 are the vital signs for the patient. For example, vital signs may be presented in a dashboard that includes the current vital signs as well as historical levels for the vital signs retrieved from the patient's records. In some embodiments, the mobile information gateway device 130 may capture additional information such as spectral images that can be used to determine the vital signs of the user. The additional information captured may be analyzed for a contemporaneous measurement of a particular vital sign and then that measurement may be presented to the medical personnel on the mobile information gateway device 130. It should be understood that the mobile information gateway device 130 may also be coupled for communication with various patient monitoring devices. These signals from those patient monitoring devices may also be received by the mobile information gateway device 130 and presented to the medical personnel during examination of the patient. As the process continues, the backend services server 108 sends 1306 instructions, warnings or reminders to the human interface module 102 for display to the user. For example, information about the patient's allergies to drugs, steps in medical procedures, usage of the correct drugs, the proper procedures etc. may be presented to the medical professional wearing the mobile information gateway device 130. Additionally or alternatively, medical imagery data may be provided in block 1306 such as ultrasounds, x-ray, MRI images, etc. The method 1300 continues by storing 1308 the information that was captured by the human interface module 102 as well as the information that was sent back for presentation by the human interface module 102 at the backend service server 108 (or other location) as a record of the interaction with the patient. Then the method 1300 determines 914 whether additional input is being received from the human interface module 102. If so, the method 1300 returns to block 1302 and repeats steps 1304, 1306 and 1308. If not the method 1300 is complete and ends.

The process described above with reference to FIG. 13 is particularly advantageous in performing triage. In one embodiment, the captured information includes images of a service area having a plurality of patients. The plurality of patients are available in the service area (e.g., a doctor's office, waiting room or emergency area of the hospital). The mobile information gateway device 130 can be used to capture images and other information about the service area, the patients in the service area and the condition of those patients. The mobile information gateway device 130 may be equipped with a camera, a microphone, imaging equipment, coupling to medical devices, coupling to other sensors (similar to the intelligent room described herein), etc. The information captured by the mobile information gateway device 130 is analyzed to determine a medical condition associated with each of the plurality of patients. The mobile information gateway device 130 processes the captured information to determine a severity of each medical condition for each patient, then ranks the patients based on the severity of associated medical condition and selects the patient with the highest rank of severity of condition to service. For example, the mobile information gateway device 130 can identify patients within the scene, identify their injuries, and then rank order them for treatment based upon an scale or index such the Emergency Severity Index (ESI) http://www.ahrq.gov/professionals/systems/hospital/esi/esi3.html. In some embodiments, the information gateway device 130 can capture and assess the surroundings such as taking pictures of the scene, heat sensing, gas/odor sensing, etc. The captured information can then be combined and analyzes other information, for example, matching it against an existing database. The mobile information gateway device 130 can also be used to capture vital signs for people identified within the scene. Along with the image information, potential patients and victims can be assessed and/or identified. For example, patient/victims without identification or unconscious can be identified and their health history retrieved. The mobile information gateway device 130 can process the scene in images to identify first responders and their interaction with patients/victims. Patients/victims that are mobile can be moved to secondary areas for later treatment. In some embodiments, the mobile information gateway device 130 cooperates with the backend services server 108 to analyze the scene information and determine the severity of the patient's/victim's injuries. Merely by analyzing the captured information for patients/victim mobility, the mobile information gateway device 130 can be used for a basic type of triage to identify likely candidates who are injured more severely and therefore unconscious or immobile. For example, the mobile information gateway device 130 may color code victims according to the urgency of need for medical attention. First, red tagged victims are cared for, the mobile information gateway device 130 can assist in ensuring that all red tagged victims are taken care of before continuing to service victims color coded with less severe injuries. In one embodiment, the color coding is displayed on the human interface module 102 overlaid over particular persons in the scene. This would be similar to the call outs described herein with reference to FIG. 15. The mobile information gateway device 130 is particularly advantageous to assist the wearer in keeping track of different colored tags, identifying the location of victims with particular colored tags, and communicating with other first responders wearing the mobile information gateway devices 130. The mobile information gateway device 130 can also establish communication with the backend service server 108 or other patient monitoring devices in the service area. In such a case, the mobile information gateway device 130 receives information from those devices and uses that information as well as the captured information to determine the severity of the medical condition for each patient. In another embodiment, the mobile information gateway device 130 can be used by medical personnel to assist in triaging the medical condition of a particular patient. For example, if the medical personnel is wearing the mobile information gateway device 130 including a human interface module 102, and meeting with the patient, the human interface module 102 can capture additional information about the patient, that information can be analyzed to determine a medical condition of the patient, the mobile information gateway device 130 can retrieve possible treatments for the identified medical condition, and the treatment information can be presented on the mobile information gateway device. For example, images of the patient may be captured and analyzed to determine physical signs of injury, symptoms of diseases, or other indications of other medical conditions. The image of the patient can be compared to other images of the patient that are part of their medical records. Furthermore triage questions can be presented on the mobile information Gateway device 130, and the answers to those questions can be recorded, converted to text, and compared to lists of symptoms or conditions associated with different medical conditions. Based on elimination and matches, the triage performed by the medical personnel can be augmented, verified, double checked, or otherwise enhanced.

The process described above with reference to FIG. 13 is particularly advantageous because according to some reports[1] there are over 200,000 medical mistakes in hospitals, operating rooms and doctors' offices every year. The use of the mobile information gateway device 130 by medical personnel as a complement to their existing procedures can help reduce some of these types of these errors. First, the mobile information gateway device 130 can provide warnings about drug allergies, drug interactions, and other unique characteristics about the patient. Second, the mobile information gateway device 130 can provide step by step instructions for best practice and proper performance of any medical procedure. Third, the mobile information gateway device 130 can monitor how procedures are being performed and provide immediate feedback to the medical personnel regarding performance of all required steps, identification of the proper use and order of use of drugs, identification of the proper medical tools for the situation, etc. The mobile information gateway device 130 can be used in surgery, during rounds at a hospital or clinic, during an inpatient visit, etc. For example, the mobile information gateway device 130 can provide a surgical checklist and thereby be another layer of authentication that the surgery was properly performed.

[1] See James, John T., "A New, Evidenced-Based Estimate of Patient Harms Associated With Hospital Care," JOURNAL OF PATIENT SAFETY, Vol. 00, No. 00, 2013

One particularly advantageous use of the mobile information gateway device 130 is for medical personnel while they are performing the procedure. During performance of that procedure, the mobile information gateway device 130 can be coupled through the network to various types of medical equipment that generate images such as ultrasounds, x-rays, and other medical imaging devices. The key advantage of the mobile information gateway device 130 is that it can be used to present the images captured by those medical devices onto the patient, and thereby allow the doctor to keep their focus on the patient and not have to look away to view the image on the screen of the medical imaging devices. For example, currently the surgeon needs to perform surgery while looking at a monitor or some other display. By using the mobile information gateway device 130, the images needed by the surgeon are displayed on the image delivery and display mechanism 302 of the human interface module 102. This helps keep surgeon's eyes on the patient rather than to a side monitor or display device. Use of the mobile information gateway device 130 also enables viewing and talking directly to the patient, rather than a screen. The natural 3-D imaging provided by the mobile information gateway device 130 can also be used to enhance the surgeon's ability to view the patient. In essence, the mobile information gateway device 130 allows the surgeon or doctor to interact more naturally with the patient. Merely by way of example, a few types of medical processes or equipment that would benefit greatly from combination with the mobile information gateway device 130 as described above include: ultrasound-guided procedures; ear imaging; fundography/retinal imaging; endoscopy surgery-aid in drilling a hole into the skull for brain surgery; performing a needle biopsy of a tumor; laryngoscope-throat surgery; or microscope surgery. More specifically, the mobile information gateway device 130 can be used to help the surgeon visualize the patient's medical condition by overlaying information from different stages of that condition or from prior visits of the user. For example, the mobile information gateway device 130 can create an image that overlay lesions on patient for comparison purposes across multiple patient visits, e.g., tumor shapes or sizes, moles appearances, etc. and how the patient healing, how the size changed because of scaled overlay.

In another embodiment, the mobile information gateway device 130 can be used in telemedicine. For example, an expert medical professional perform in particular procedure can wear the mobile information gateway device 130 during the procedure as well as augment the procedure with an audio narrative. The mobile information gateway device 130 can capture images of how the procedure is performed as well as the audio narrative. Both of these types of information can be sent from the mobile information gateway device 130 to the backend service center 108. The backend service server 108 could stream this information in real time for teaching of students or other professionals with less expertise. One advantage of using the mobile information gateway device 130 is that people can participate remotely and they receive an unobstructed view of the procedure from the same vantage point as the person performing the procedure. The information can also be stored on the backend service center 108 and archived so that others may view it at any time if they are not able to view it in real time. In addition to being recorded and stored on the backend server 108, the recording of the procedure may be augmented by overlaying other information such as graphics, audio, highlights or callouts to identify key aspects of a procedure or areas that require extra special detail. It may be useful to record what is being seen through an image delivery and display mechanism 302 (e.g., scene information) including the overlay. The scene information and the overlay can be stored jointly or separately for later recreation.

The mobile information gateway device 130 can also be used to allow an experienced doctor to work with and communicate with less experienced doctors, or even non-medical personnel. For example, the mobile information gateway device 130 could allow the world's expert in a particular area to communicate with a general physician in a very remote area and assist with triage, diagnosis, or actual performance of the procedure. With the person in the field wearing the mobile information gateway device 130, a remote instructor or teacher can be provided with the same view as the person in the field. The remote instructor can then provide instructions or aid to the person out in the field and moreover, the entire session can be recorded. This allows telepresence where the patient can be assessed by a doctor virtually and remotely.

The above description of the medical information gateway system 100 as used in healthcare has primarily been described with the user of the medical information gateway device 130 being the medical professional or their staff. However, it should be noted that in the healthcare context, the medical information gateway device 130 may also be used by the patient. For example, a patient may wear the medical information gateway device 130 while he/she is in the waiting room and can be privately shown customized education or entertainment materials. These materials may be specific to the procedure that he/she is about to go through. The medical information gateway 130 can be used by both the doctor and the patient to visualize medical procedure including 3-D modeling of the procedure, discussion of the treatment plan, graphs and timelines for treatment, expectations of treatment etc. For example, a cancer treatment plan could include the procedures that are going to happen such as chemotherapy and what the impact on the patient may be. This may be shown over images of the patient or remodeling that may happen because of the procedure or treatment. In such an embodiment, the patient and the medical personnel each have a corresponding medical information gateway device 130. Each user is identified and authenticated in a manner similar to that described above with reference to FIG. 9. Information can then be presented on each respective medical information gateway device 130 overlaid over each respective user's field of view. This is similar to the example described above with reference to FIGS. 16A and 16B, but for presenting medical information. For example, retrieved information of the patient is overlaid on the field of view by the first mobile information gateway device for the patient while the same information is overlaid on the second field of view by the second mobile information gateway device for the medical personnel. The mobile information gateway devices 130 of the patient and the doctor may also present private sets of data only to the patient and doctor, respectively. For example, a first set of data may be presented only on the first mobile information gateway device 130 to the patient while a second set of data may be presented only on the second mobile information gateway 130 to the doctor. As noted above, the information presented on the mobile information gateway devices 130 can include providing a three dimensional image of data from a first perspective of the first user (e.g., a doctor) based on a position of the first mobile information gateway device 130. The same information may be presented to the patient using a second mobile information gateway device 130 but with a different three dimensional image of the same data from a second perspective of the patient based on a position of the second mobile information gateway device 130. Furthermore, a private encrypted communication channel between a first mobile information gateway device 130 used by the patient and the second mobile information gateway device 130 used by medical personnel can ensure the privacy of communication between the patient and doctor.

In another embodiment, the medical information gateway device 130 may be used by the patient alone to view their own medical information so that they may discuss it with their physician. If the physician is also wearing a mobile information gateway device 130, both devices can be used by each individual to aid in communication during the consultation, walk through procedures, show procedures or 3-D modeling, show how the process will affect the body, show before and after images, etc. This could also include language translation where the patient and medical personnel speak different languages. In yet other embodiments, the mobile information gateway device 130 can be used to provide treatment of illnesses. For example, the augmented reality provided by the mobile information gateway device 130 can be used to present images or allow the patient to visualize situations for the treatments of their phobias or psychological problems. In other words, particular situations or images that the patient is afraid of can be presented on the mobile information gateway device 130 so that the patient can develop processes and routines to handle those situations of which they are afraid. Then when the patient is exposed to those situations in real life, they have a mechanism to deal with those situations because they had been trained using the mobile information gateway device 130. The mobile information gateway device 130 may also be used to treat as myopia and amblyopia or other conditions that can benefit from the user viewing a display with a wide field of view. Research has shown effectiveness of using video games such as first-person shooting games and Tetris to improve vision.[2]

[2]See https://www.mcgill.ca/channels/news/lazy-eye-disorder-promising-therapeutic-approach-226011

Figure 17:
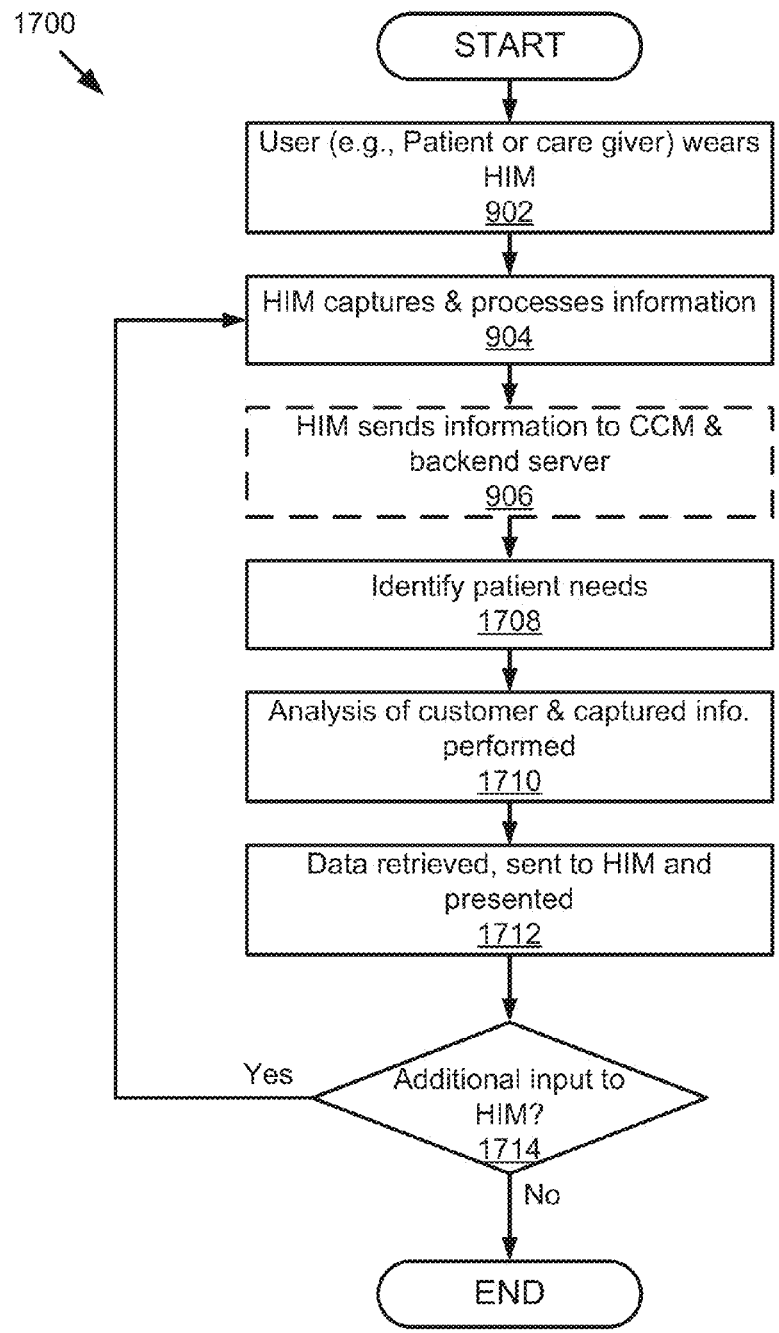
FIG. 17 is a flow chart of one embodiment of a method for asymmetrical use of the mobile information gateway by a patient or a patient's caregiver.

Further, the medical information gateway device 130 may be used by the patient alone or a caregiver to the patient in some embodiments. A method 1700 for such use by a patient or caregiver is shown in FIG. 17 and will be described below. The method 1700 begins with three steps 902, 904 and 906 as has been described above with reference to FIG. 9. Specifically, the method 1700 captures 902 information with a human interface module 102; processes the captured information to determine 904 an identity of a user of the human interface module 102; and authenticates 906 the identity of the user. The method 1700 continues by identifying 1708 the patient's needs by processing the information captured in block 904. The method 1700 also performs 1710 analysis of the captured information based on the identity of the user as well as authentication of the user. The method 1700 then retrieves 1712 data and sends the data to the human interface module 102 for presentation to the user. In some instances, additional information needs to be captured by the human interface module 102. The method 1700 determines whether there is additional input to the human interface module 102 or additional input from the human interface module 102 is needed. If either condition is true, the method 1700 returns to block 904 to capture additional information and proceed through blocks 906, 1708, 1710 and 1712. On the other hand, if both conditions are false, no additional input is needed and the method 1700 is complete and ends. It should be understood that the blocks of identifying 1708, analyzing 1710 and retrieving 1712 may take a variety of different forms a few examples of which are described below.

In a first example, the patient is wearing the mobile information gateway device 130 and it is used to access the medical records of the patient. In this example, the mobile information gateway device 130 determines at least one accessible medical record based upon the identity of the user and retrieves the information and presents it to the user on the human interface module 102. In one embodiment, the information is stored on the computing and communication module 104 and the human interface module 102 merely retrieves the medical record. In another embodiment, the information is stored at the backend service server 108 and the mobile information gateway device 130 retrieves the information from the backend service server 108. In a similar example, the user of the mobile information gateway device 130 is a caregiver for a patient. In such an example, the patient must be identified by processing the captured information. Then the mobile information gateway device 130 determines whether there are any medical records that can be accessed based on both the identity of the caregiver and the identity of the patient. If so, the mobile information gateway device 130 retrieves one or more medical records and presents those medical records on the display of the human interface module 102. Since the caregiver is using the mobile information gateway device 130, the caregiver either uses the information herself or provides that information to the patient.

In a second example, the patient is wearing the mobile information gateway device 130 and it is used for communication with medical personnel at a remote location. In the second example, the medical personnel are available using a second remote device. The remote device may be a second medical information gateway device 130 or it may be another computing device such as a laptop computer, desktop computer, a tablet computer or a smart phone. In addition to the steps (or in place of some of them) described above with reference to FIG. 17, the mobile information gateway device 130 establishes a communication link with the second device available to medical personnel. The mobile information gateway device 130 of the patient collects/captures information and sends that information to the second device. In response, the medical personnel review the information received on the second device then input and sends medical or instructional information to the mobile information gateway device 130. The mobile information gateway device receives the medical or instructional information and presents it on the human interface module 102. This use of the mobile information gateway device 130 is particularly advantageous because the patient can remain in their home and consult with their physician or other medical personnel using the mobile information gateway device 130. The mobile information gateway device 130 captures and sends information to the medical personnel. That information can be images, audio, video, vital signs, etc. The interaction with the medical personnel can be live and interactive. In some embodiments the interaction is similar to an audio or video conference. In other embodiments, the medical personnel can merely type or input instructions and they are treated as text and displayed to the patient using the mobile information gateway device 130. Thus, the patient receives a medical consultation similar to what the patient would receive if the patient were in a clinic or hospital in person. In adaptations of this embodiment, the second device includes machine learning, neural network, an expert system or other technology that is able to process the inputs and provide system a diagnosis and proposed treatment in response to the information captured by the mobile information gateway device 130.

In a third example similar to the second example, the patient is wearing the mobile information gateway device 130 and information is provided on the human interface module 102 to teach or advise the patient how to treat himself. For example, the information captured in block 904 is processed in block 1708 to determine a medical condition of the user. The medical condition can be a new injury or it can be a disease with manifestations that are detectable by the mobile information gateway device 130. Additionally, the patient's past history with the disease may also be retrieved using the mobile information gateway device 130 and then used in the analysis of block 1710. Once the medical condition has been identified, the analysis 1710 identifies a procedure or information to address the medical condition. The procedure or information is then retrieved by the mobile information gateway device 130 and that information is provided to the human interface module 102 for presentation to the user. For example, instructions on how to replace a dressing on a wound can be presented on the human interface module 102. The presentation of these instructions can be synchronized with the actions of the patient as captured by the information gateway device 130. In particular, the process may begin by presenting instructions on the human interface module 102 for the patient to remove any existing bandages. The mobile information gateway device 130 can capture the patient's actions and determined from image analysis when the old bandages have been removed. Once the old bandages have been removed, the mobile information gateway device 130 can provide instructions to apply antibiotic ointment. Again, the mobile information gateway device 130 will capture the patient's actions and can determine when they have finished applying ointment to the wound. Finally, the mobile information gateway device 130 can provide step-by-step instructions on how to apply a new bandage to the wound. If the bandage is being applied improperly, the mobile information gateway device 130 can adapt the information presented and instruct the patient to undo part of the bandage or re-bandage parts that need correction. This is merely one example and it should be understood how other instructions and procedures can be presented in a similar manner using the mobile information gateway device to the patient. For example, similar instructions may be provided as to how to bandage a sprained ankle for stabilization. Additional information can be captured and used by the mobile information gateway device 130, as represented by the loop from block 1714 back to block 904. The actions of the user in performing the suggested procedure or treatment may be captured by the mobile information gateway device 130. These actions can then be analyzed and compared in block 1710 to the identified ideal procedure that was sent to the user. If the user is performing the procedure correctly, no further action is it necessary. However, if the actions for performing procedure are beyond an acceptable tolerance, corrective instructions for performing the identified ideal procedure can be sent to the human interface module. In some embodiments, these corrective instructions can be sent to the human interface module 102 in real time so that the performance of the procedure can be adjusted as needed to ensure that is implemented correctly.

In a fourth example, the patient is wearing the mobile information gateway device 130 and it can be used to monitor the condition of a patient or to monitor the progression (or regression) of a condition. In this example, the patient is either continuously wearing the mobile information gateway device 130 or repeatedly wears the mobile information gateway device 130 at multiple times of sufficient duration to perform the monitoring. For example, the patient may wear the mobile information gateway device 130 as has been described above, process the captured information, and determine a medical condition. The captured information, the identity of the user, and other metadata may be stored by the mobile information gateway device 130. This information may be stored at the computing and communication module 104 or the backend service server 108 or both. After a predetermined amount of time, the mobile information gateway device 130 can capture additional information about the status of the user, including the identified medical condition, and store the information. By repeating this process over and over, the mobile information gateway device 130 can be used to monitor the patient's condition. The information captured can also be used to determine whether the condition of the patient is improving or worsening. In some cases, monitoring can be performed merely to get a baseline of a patient's condition. For example, the mobile information gateway 130 could be used to obtain baseline measurements over a longer period of time for the blood pressure and pulse of the patient.

In other cases, the mobile information gateway device 130 can be used to determine the progression of a particular medical condition, provide information back to the patient about the advancement or withdraw of that condition, and automatically generate and send messages to medical personnel indicating an emergency situation, recommend treatment or present other information or take other action. For example, assume a patient has skin cancer and the disease is evidenced by cancerous growths that are black or brown in color. While some growths may be benign, sometimes the skin cells mutate and lead to skin cells that multiply rapidly and form malignant tumors. The mobile information gateway device 130 can be used by the patient to capture images of areas of their skin, for example on his arm that may have such cancerous growths on a weekly, daily or even hourly basis. The mobile information gateway device 130 can be used on any repeating basis to capture additional images of the same areas with those growths. The mobile information gateway device 130 can compare the currently captured information to previously captured information to determine a difference in the size of the growths (or more generally to determine differences in the medical condition). Depending on the differences, additional information can be provided via the mobile information gateway device 130. For example, a message may be provided recommending that the patient see their physician, a treatment recommended, a medicine recommend, a procedure recommend, etc. In some embodiments, the mobile information gateway device 130 can create an overlay image that shows the difference in the size of the growth. The mobile information gateway device 130 can also be used to provide augmented information such as calibration as to the size of the growth, whether the growth are the same as were previously present ones, metrics on percentage growth or percentage reduction, progression on growth and healing, etc. It should be understood that the imaging capability of the mobile information gateway device 130 is merely one example. The mobile information gateway device 130 also includes other types of spectral imaging, audio recording, and may be connected to other patient monitoring devices. The audio capture capability of the mobile information gateway device 130 could be used to monitor a cough frequency of the patient or the breathing pattern of the patient (e.g., for sleep apnea). Moreover, the mobile information gateway device 130 could establish communication with one or more patient monitoring devices. Information received from coupled patient monitoring devices could be processed and analyzed as well as stored at the back and services server 108. In some embodiments, the mobile information gateway 130 may also send this information so that it may be part of a medical record presented to a physician such as by transferring the information to the backend service server 108 or directly to the information system of a medical professional. It should be understood that the mobile information gateway device 130 advantageously has the capability to capture a number of different types of information and thereby may be able to monitor and track any number of medical conditions.

In a fifth example, the patient is wearing the mobile information gateway device 130 and it can be used to assist with the proper use of medications. For example, the information captured and processed in block 904 can include many of the activities undertaken by the patient. For example, the mobile information gateway device 130 may record when the patient eats, sleeps, drinks, rests, exercises etc. Additionally, additional analysis of the captured information may determine what is actually being eaten, what is drank, etc. Thus, the image capture capabilities of the mobile information gateway device 103 can be used to capture pills, injections, etc. before the patient administers them. In many cases, different medications have different sizes, colors, shapes, markings, etc. If the patient captures an image of a pill or medication before it is taken, the mobile information gateway device 130 can capture an image of the pill, process that image to determine possible types of medication that it may be, and confirmed that the medication is for the patient. For example, the medication may be for another person that shares the household with the patient. Thus the processing of the captured image can identify the type of medication. Similarly, an image of the packaging of the medication could be captured to determine relevant information about the medication such as whom the prescription is for, the prescribed dose, the prescribed times for administration, any drug interaction issues, and whether other conditions must be present for administration of medication. Once the type has been determined, the mobile information gateway device 130 can determine whether that medication has been prescribed for the patient. Since the mobile information gateway device 130 is captured much of the patient's activities, it can also determine by processing the captured information whether the conditions for taking the medication have been satisfied. For example, some medications cannot or should not be taken with alcohol while other medications should be taken with food. Still other medications must be taken at certain times of the day. Since the mobile information gateway device 130 captures the other activities of the patient, it can determine and analyze based on other information captured, whether the conditions for taking the medication have been satisfied. In some embodiments, the mobile information gateway device 130 sends a warning message that can be presented on the human interface module if either the type of medication is not prescribed for the patient or one or more conditions for taking the medication are not satisfied.

In a sixth example, a care giver is wearing the mobile information gateway device 130 and it is used to capture information about the patient. For example, a caregiver may wear the mobile information gateway device 130 and capture information about an elderly patient. Similarly, a parent or nanny may wear the mobile information gateway device 130 and capture information about children. Additionally, a therapist (e.g., a speech therapist or audiologist) could wear the mobile information gateway device 130 and use it to display audio or video from prior meetings and assess the progress of the patient. Similarly, an occupational therapist can use the mobile information gateway device 130 to display a child's history while engaging with the child. In any of these cases, the mobile information gateway device 130 captures information and that information is processed to determine a medical condition. Information about the medical condition is retrieved by the mobile information gateway device 130 and presented on the human interface module 102. In the example of the parent or nanny wearing the mobile information gateway device 130, this is advantageous because information that is not suitable for the patient, a child, can be presented using the mobile information gateway device 130 to the parent only. For example, the mobile information gateway device 130 may be used to capture skin rashes on a child. Other measurements such as temperature of the skin may be made and a child's condition can be assessed and monitored over time. The mobile information gateway device 130 can also be used to provide instructions to the parent as to the proper treatment for the rash. In another example, images of the child can be captured to identify insect bite marks such as from ticks. Images of the child's skin can be captured and monitored for changes in their characteristics. In some embodiments, the images of the child can be captured and the locations of the rashes or other conditions on the skin can be identified and a location provided to the parent or nanny wearing the mobile information gateway device 130. In some embodiments, another person may be wearing a second mobile information gateway device 130. In such cases, the information can be sent to both mobile information gateway devices 130 so that both parents may see the information about the medical condition as well as the prescribed treatment. In a similar scenario, particular information may be selectively provided two different mobile information gateway devices 130 such as one being used by a patient versus another being used by a physician.

In a seventh example, the mobile information gateway device 130 can be used to monitor the condition of the patient, and make recommendations or send reminders. For example, if the mobile information gateway device 130 is continuously worn by the patient or even worn on a regular basis, the mobile information gateway device 130 can measure basic vital signs, generate a reminder to perform a medical activity or physical therapy, and present reminders on the human interface module 102. For example, the mobile information gateway device 130 may remind a patient to take a medication, exercise, perform physical therapy, diet before procedure, etc. Furthermore, the nature and frequency of the reminders may be customized based on user preferences that the patient enters using the mobile information gateway device 130.

It should be understood that the above descriptions for the use of the mobile information gateway system 100 in the financial services sector and the healthcare sector, are merely examples, and that there are various other applications for the mobile information gateway system 100 such as but not limited to repair services for printers, copiers and other electronic equipment; diagnosis, triage and instructions for auto repair; instructions for cooking; etc. In some embodiments, the mobile information gateway device 130 can be used to identify the part in a scene (and overlay highlighting so the part is easy to identify) as well as provide instructions as what to do with that part ("Step 1:: turn this on," "Step 2: pull this out," etc.).

Additionally, the mobile information gateway system 100 may be used by first responders such as the police, the fire department and paramedics. The first responders may be wearing a mobile information gateway device 130 that provides information about the situation to which they responding and any critical changes in the circumstances. By wearing a mobile information gateway device 130 information such as a floor plan for building or office (e.g. available from County records), map information, information about and communication with other first responders can be provided to each individual user that is part of the response team. Similarly, a method for first responders to use the mobile information gateway device 130 includes: capturing information with the mobile information gateway device 130; processing the information captured by the mobile information gateway device to detect an emergency condition; analyzing the information captured by the mobile information gateway device to identify an emergency response; retrieving instructional information corresponding the emergency response; and providing the instructional information on the mobile information gateway device. In this process, the emergency condition may be detected by processing video or audio captured by the mobile information gateway device 130 using scene or image analysis to detect fire, accidents, crimes, etc. The information captured by the mobile information gateway device 130 is also analyzed to identify the appropriate emergency response. In some examples, the video captured by the mobile information gateway device 130 may be processed and analyzed by the back and service server 108. The emergency condition may be a more general emergency condition affecting a number of individuals such as fire, accidents or crimes or the emergency condition may be a more specific emergency condition affecting only one particular individual, for example, a specific injury to a human being and the instruction information is first aid instructions corresponding to the specific injury. For example, a scene might be analyzed to identify an injury to a particular person in the scene. Depending on the emergency response, different instructional information is provided to the mobile information gateway device 130. For example, the instructional information may be a list of step-by-step instructions for addressing the emergency condition. As noted above, in one embodiment, the mobile information gateway device 130 is self-contained and includes the human interface module 102 and the computing and communications module 104. The computing and communications module 104 advantageously stores first aid information accessible and presentable by the human interface module 102. In response to the human interface module 102 detecting a particular emergency condition (injury) and identifying the appropriate response, the human interface module 102 retrieves information about the identified appropriate response from the computing and communication module 104. The retrieved information is then presented by the human interface module 102. In some embodiments, the mobile information gateway device 130 may also be coupled for communication and control of other safety devices. Thus, when the mobile information gateway device 130 detects an emergency condition, the mobile information gateway device 130 can also analyze the captured information to determine whether the other safety device should be deployed. If so, the mobile information gateway device 130 can send a signal to activate the other safety devices. For example, the mobile information gateway device 130 may be coupled to control a fire suppression system or control the locking or unlocking of doors. If the mobile information gateway device detects the emergency condition and it is a fire, the mobile information gateway device 130 can activate the fire purse suppression system, or unlocked doors to allow people to exit the rooms that make be ablaze. The mobile information gateway device 130 could be coupled to a plurality of different types of safety devices and deploy the appropriate safety device depending on detection of an emergency condition and the identification of the type of emergency condition. In some embodiments, the mobile information gateway device 130 may be configured to automatically generate and send an emergency message that identifies the type of emergency to an emergency dispatch center when the emergency condition is detected. Similar to the documentation case noted above, the mobile information gateway device 130 may also be configured to record as much audio and video information as possible one emergency is detected. To the extent that the mobile information gateway device 130 also has other sensors, though sensors may be activated and the signals recorded.

A mobile information gateway and methods of use have been described above. In the above description, for purposes of explanation, numerous specific details are set forth in order to provide a thorough understanding of the specification. It will be apparent, however, to one skilled in the art that the invention can be practiced without these specific details. In other instances, structures and devices are shown in block diagram form in order to avoid obscuring the description. For example, the present invention is described in one embodiment below primarily with reference to user interfaces and particular hardware. However, the present invention applies to any type of computing system that can receive data and commands, and present information as part of a mobile device.

Reference in the specification to "one embodiment" or "an embodiment" means that a particular feature, structure, or characteristic described in connection with the embodiment is included in at least one embodiment of the description. The appearances of the phrase "in one embodiment" in various places in the specification are not necessarily all referring to the same embodiment.

Some portions of the detailed descriptions described above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present specification also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The specification can take the form of an entirely hardware embodiment, an entirely software embodiment or an embodiment containing both hardware and software elements. In one embodiment, the specification is implemented in software, which includes but is not limited to firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the embodiments of the present embodiment of invention has been presented for the purposes of illustration and description. It is not intended to be exhaustive or to limit the present embodiment of invention to the precise form disclosed. Many modifications and variations are possible in light of the above teaching. It is intended that the scope of the present embodiment of invention be limited not by this detailed description, but rather by the claims of this application. As will be understood by those familiar with the art, the present embodiment of invention may be embodied in other specific forms without departing from the spirit or essential characteristics thereof. Likewise, the particular naming and division of the modules, routines, features, attributes, methodologies and other aspects are not mandatory or significant, and the mechanisms that implement the present embodiment of invention or its features may have different names, divisions and/or formats. Furthermore, as will be apparent to one of ordinary skill in the relevant art, the modules, routines, features, attributes, methodologies and other aspects of the present embodiment of invention can be implemented as software, hardware, firmware or any combination of the three. Also, wherever a component, an example of which is a module, of the present embodiment of invention is implemented as software, the component can be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming. Additionally, the present embodiment of invention is in no way limited to implementation in any specific programming language, or for any specific operating system or environment. Accordingly, the specification of the present embodiment of invention is intended to be illustrative, but not limiting, of the scope of the present embodiment of invention, which is set forth in the following claims.

What is claimed is:

1. A method of using a mobile information gateway for medical personnel, the method comprising:
   capturing information with a first mobile information gateway device, the first mobile information gateway device being wearable by a first user;
   processing the captured information to determine an identity of the first user;
   processing the captured information to determine an identity of a patient;
   processing the captured information to identify a body part of the patient in a physical space;
   mapping a position of the body part of the patient in the physical space to a field of view of the first mobile information gateway device;
   processing, with the first mobile information gateway device, the captured information to authenticate the identity of the first user;
   processing, with the first mobile information gateway device, the captured information to authenticate the identity of the patient;
   determining, with the first mobile information gateway device, that information of the patient can be accessed by the first user based on the identity of the patient and the identity of the first user;
   processing the authenticated identity of the first user and the authenticated identity of the patient to retrieve information of the patient that the identified first user can view, the retrieved information including information about a prior stage of a medical condition of the patient;
   overlaying the information about the prior stage of the medical condition of the patient over the body part of the patient on a transparent display based on the mapped position to show a change in the medical condition of the patient from the body part of the patient that can be seen through and the information about the prior stage; and
   presenting the retrieved information of the patient, with the first mobile information gateway device, in a virtual plane so the retrieved information appears overlaid on the body part of the patient.

2. The method of claim 1 wherein the processing the captured information to authenticate the first user and the patient includes performing facial recognition or iris recognition.

3. The method of claim 1 wherein the retrieved information of the patient includes a vital sign of the patient and wherein presenting the retrieved information includes presenting a dashboard including the vital sign.

4. The method of claim 1 comprising:
   capturing additional information with the first mobile information gateway device;
   analyzing the additional information to determine a vital sign; and
   wherein the retrieved information of the patient includes the vital sign.

5. The method of claim 1 wherein the field of view includes a view of a service area having a plurality of patients, and processing the captured information to determine the identity of the patient and authenticate the patient comprises:
   receiving a patient identity;
   analyzing the captured information to identify the patient; and
   wherein the retrieved information of the patient overlaid on the field of view is an indicator to specify the patient.

6. The method of claim 1 wherein the field of view includes a view of a service area having a plurality of patients, and processing the captured information to determine the identity of the patient comprises:
   processing the captured information to determine the medical condition associated with each of the plurality of patients;
   determining a severity of each medical condition using the captured information;
   ranking the plurality of patients based on the severity of the associated medical condition; and
   selecting as the patient one of the plurality of patients having a highest rank of severity.

7. The method of claim 6 comprising:
   establishing communication between the first mobile information gateway device and a patient monitoring device;
   receiving by the first mobile information gateway device signals from the patient monitoring device; and
   using the signals from the patient monitoring device for determining the severity of each medical condition.

8. The method of claim 1 comprising:
   capturing additional information about the patient with the first mobile information gateway device;
   analyzing the additional information to determine the medical condition of the patient;
   retrieving treatment information for the medical condition; and
   providing the treatment information to the first mobile information gateway device.

9. The method of claim 1
   wherein capturing the information with the first mobile information gateway comprises capturing the information about prior stages of the medical condition of the patient.

10. The method of claim 9, comprising:
    establishing communication between the first mobile information gateway device and a patient monitoring device;
    receiving by the first mobile information gateway device a signal of patient condition from the patient monitoring device; and
    wherein the retrieved information of the patient includes the received signal of patient condition from the patient monitoring device including one or more from the group of blood pressure, blood flow, blood glucose, heart rate, temperature, electrocardiography, pulse oximetry, capnography, respiratory rate and intracranial pressure.

11. The method of claim 1 further comprising:
    capturing additional information with a second mobile information gateway device;
    processing the captured additional information with the second mobile information gateway device to determine the identity of the patient wearing the second mobile information gateway;
    performing another authentication, using the second mobile information gateway device, of the identity of the patient using the additional information captured with the second mobile information gateway device; and presenting the retrieved information of the patient overlaid on a second field of view by the second mobile information gateway device.

12. The method of claim 11 wherein:
presenting the retrieved information of the patient by the first mobile information gateway device includes providing a first set of data on a private display of the first mobile information gateway device; and
presenting the retrieved information to the patient overlaid on the second field of view by the second mobile information gateway device includes providing a second set of data on a private display of the second mobile information gateway device.

13. The method of claim 11 wherein:
presenting the retrieved information of the patient, with the first mobile information gateway device, in the virtual plane so the retrieved information appears overlaid on the body part of the patient in the field of view of the first mobile information gateway device includes providing a three dimensional image of data from a first perspective of the first user based on a position of the first mobile information gateway device; and
presenting the retrieved information to the patient overlaid on the second field of view by the second mobile information gateway device includes providing the three dimensional image of the data from a second perspective of the patient based on a position of the second mobile information gateway device.

14. The method of claim 11 further comprising establishing a private encrypted communication channel between the first mobile information gateway device and the second mobile information gateway device.

15. A system for providing healthcare services comprising:
a processor, and;
a memory storing instructions that, when executed, cause the system to:
capture information with a first mobile information gateway device, the first mobile information gateway device being wearable by a first user;
process the captured information to determine an identity of a first user;
process the captured information to determine an identity of a patient;
process the captured information to identify a body part of the patient in a physical space;
map a position of the body part of the patient in the physical space to a field of view of the first mobile information gateway device;
process, with the first mobile information gateway device, the captured information to authenticate the identity of the first user;
process, with the first mobile information gateway device, the captured information to authenticate the identity of the patient;
determine, with the first mobile information gateway device, that information of the patient can be accessed by the first user based on the identity of the patient and the identity of the first user;
process the authenticated identity of the first user and the authenticated identity of the patient to retrieve information of the patient that the identified first user can view, the retrieved information including information about a prior stage of a medical condition of the patient;
overlay the information about the prior stage of the medical condition of the patient over the body part of the patient on a transparent display based on the mapped position to show a change in the medical condition of the patient from the body part of the patient that can be seen through and the information about the prior stage; and
present the retrieved information of the patient, with the first mobile information gateway device, in a virtual plane so the retrieved information appears overlaid on the body part of the patient.

16. The system of claim 15 wherein the field of view includes a view of a service area having a plurality of patients and the memory also stores instructions that, when executed, cause the system to:
process the captured information to determine the medical condition associated with each of the plurality of patients;
determine a severity of each medical condition using the captured information;
rank the plurality of patients based on the severity of the associated medical condition; and
select as the patient one of the plurality of patients having a highest rank of severity.

17. The system of claim 15 wherein the memory also stores instructions that, when executed, cause the system to:
capture additional information about the patient with the first mobile information gateway device;
analyze the additional information to determine the medical condition of the patient;
retrieve treatment information for the medical condition; and
provide the treatment information to the first mobile information gateway device.

18. The system of claim 15 wherein
capturing the information with the first mobile information gateway device comprises capturing the information about prior stages of the medical condition of the patient.

19. The system of claim 15 wherein the memory also stores instructions that, when executed, cause the system to:
capture information with a second mobile information gateway device;
wherein processing the captured information to determine the identity of the patient and authenticate the identity of the patient uses the information captured with the second mobile information gateway device; and
present the retrieved information of the patient overlaid on a second field of view by the second mobile information gateway device.

20. A computer program product comprising a non-transitory computer usable medium including a computer readable program, wherein the computer readable program when executed on a computer causes the computer to perform:
capturing information with a first mobile information gateway device, the first mobile information gateway device being wearable by a first user;
processing the captured information to determine an identity of a first user;
processing the captured information to determine an identity of a patient;
processing the captured information to identify a body part of the patient in a physical space;
mapping a position of the body part of the patient in the physical space to a field of view of the first mobile information gateway device;

processing, with the first mobile information gateway device, the captured information to authenticate the identity of the first user;

processing, with the first mobile information gateway device, the captured information to authenticate the identity of the patient;

determining, with the first mobile information gateway device, that information of the patient can be accessed by the first user based on the identity of the patient and the identity of the first user;

processing the authenticated identity of the first user and the authenticated identity of the patient to retrieve information of the patient that the identified first user can view, the retrieved information including information about a prior stage of a medical condition of the patient;

overlaying the information about the prior stage of the medical condition of the patient over the body part of the patient on a transparent display based on the mapped position to show a change in the medical condition of the patient from the body part of the patient that can be seen through and the information about the prior stage; and presenting the retrieved information of the patient, with the first mobile information gateway device, in a virtual plane so the retrieved information appears overlaid on the body part of the patient.

* * * * *

UNITED STATES PATENT AND TRADEMARK OFFICE
CERTIFICATE OF CORRECTION

| | |
|---|---|
| PATENT NO. | : 10,095,833 B2 |
| APPLICATION NO. | : 14/161601 |
| DATED | : October 9, 2018 |
| INVENTOR(S) | : Nikhil Balram et al. |

Page 1 of 1

It is certified that error appears in the above-identified patent and that said Letters Patent is hereby corrected as shown below:

On the Title Page

Item (57), In the Abstract, Line 15, please replace "and resenting the retrieved information of the patient" with – and presenting the retrieved information of the patient –

Signed and Sealed this
Tenth Day of March, 2020

Andrei Iancu
*Director of the United States Patent and Trademark Office*